United States Patent [19]
Jachowicz et al.

[11] Patent Number: 5,452,233
[45] Date of Patent: Sep. 19, 1995

[54] STREAMING POTENTIAL SYSTEM AND METHOD

[75] Inventors: Janusz Jachowicz, Bethel; Suzan M. Maxey, Bridgeport; Carl Williams, Stratford, all of Conn.

[73] Assignee: Clairol, Inc., New York, N.Y.

[21] Appl. No.: 350,244

[22] Filed: Dec. 6, 1994

Related U.S. Application Data

[63] Continuation of Ser. No. 864,451, Apr. 6, 1992, abandoned.

[51] Int. Cl.$^6$ ............................................. B01J 8/00
[52] U.S. Cl. ............................ 364/499; 364/509; 364/510
[58] Field of Search .............. 364/499, 509, 510; 324/71.1, 453; 137/10, 624.11; 436/518; 624/11; 73/53.04

[56] References Cited

U.S. PATENT DOCUMENTS

| | | | |
|---|---|---|---|
| 4,274,937 | 6/1981 | Findl et al. | 204/411 |
| 4,535,285 | 8/1985 | Evans et al. | 324/71.1 |
| 5,051,922 | 9/1991 | Toral et al. | 364/510 |
| 5,091,863 | 2/1992 | Hungerford et al. | 364/510 |

*Primary Examiner*—Ellis B. Ramirez
*Assistant Examiner*—Thomas Peeso
*Attorney, Agent, or Firm*—M. S. Simon

[57] ABSTRACT

A system and method for measuring streaming potential, conductivity and permeability of a porous sample, such as a plug of fibrous material, in which a test electrolytic solution, such as a neutral dilute salt solution, is flowed through a flow cell containing the sample. The test solution, and a treatment solution whose effect on the sample is to be measured, are flowed through the flow cell as a series of liquid spurts. The system includes a plurality of solenoid valves which are controlled by a computer in accordance with a software program.

21 Claims, 102 Drawing Sheets

STREAMING POTENTIAL SYSTEM AND METHOD

This application is a continuation of U.S. application Ser. No. 07/864,451, filed Apr. 6, 1992, now abandoned.

FIELD OF THE INVENTION

The present invention relates to scientific measurement instrumentation and methods and more particularly to a system and method to determine streaming potential, conductivity, permeability, zeta potential and the analysis of the sorption and desorption of ions on a permeable body such as a fiber plug.

RELATED ART

One type of electrokinetic measurement is the measurement of the streaming potential. An electrolytic solution is flowed through a permeable body, for example, a capillary, porous solid or a plug of fiber such as hair or fabric. The streaming of the liquid through the permeable body produces an electrokinetic force (current or potential) which may be measured. For example, an electrometer measures the electrical potential across the plug caused by the flow of liquid.

The streaming potential provides a measurement which may be used for the evaluation of zeta potentials at solid-liquid interfaces. The zeta potential $\zeta$ a may be simply defined (without corrections) as follows:

$$\zeta = \frac{4\pi n\, k\, E}{PD}$$

where E is the streaming potential, n is the viscosity of the liquid, k is the conductivity of the liquid, P is the applied pressure on the liquid, and D is the dielectric constant of the liquid.

It is seen that if the pressure is kept constant and the same liquid is used for a series of experiments, the zeta potential for that series of experiments is directly proportional to the streaming potential, i.e., the only variable is the streaming potential.

A typical laboratory apparatus to measure the streaming potential uses a plug or pad of porous material having perforated gold or platinum disk electrode plates at the opposite ends of the plug. Compressed air forces liquid contained in a supply reservoir through the plug and into a collection reservoir.

The electrical potential E (voltage), which is the streaming potential, is measured by an electrometer—potentiometer system connected to the two disk electrodes. Zeta potentials are useful in predicting the stabilities of lyophobic sols such as aqueous colloidal suspensions of oil, clay, gold and metal oxides. For these colloidal suspensions, electrostatic repulsion operates between particles of like charge to stabilize the particles against collisions that lead to irreversible coagulation. The particle charge is directly proportional to zeta potential and there is a certain minimum zeta potential (the critical potential) above which a particular type of colloidal sol is stable for an indefinite length of time. Below the critical potential, coagulation occurs in a relatively short time. The streaming potential depends upon the presence of an electrical double layer at a solid-liquid surface. The electrical double layer is made up of ions of one charge type which are fixed to the surface of the solid and an equal number of mobile ions of the opposite charge which are distributed through the neighboring region of the liquid phase. In such a system the movement of liquid over the surface of the solid produces an electric current, because the flow of liquid causes a displacement of the mobile counter ions with respect to the fixed charges on the solid surface. The applied potential necessary to reduce the net flow of electricity to zero is the streaming potential.

An "Electro-Kinetic Analyzer" which may measure streaming potential and streaming current on a plug of fibers using silver/silver chloride electrode disks is available as the "Paar-B1-EKA" from Brookhaven Instruments, Holtsville, N.Y.

The presently commercially available systems for measuring streaming potentials suffer from a number of deficiencies. Generally such systems measure the sample in a static mode in which the sample is manually loaded, unloaded and then reloaded for each step of the procedure. For example, untreated hair fibers are formed into a plug and loaded into a streaming potential flow cell (test cell). A test solution, under one or more different pressures, is flowed through the flow cell and the streaming potential measured. The fibers are then removed from the flow cell, processed with the treatment material, reloaded into the flow cell, and remeasured using a flow of test solution. That type of system often produces streaming potential readings which are not stable over time, i.e., they are time dependent, the experimental data is scattered for the same material and the same conditions, and in general the results are not reproducible. Such lack of reproducible results may arise, in some cases, from forming the pads non-uniformly from one experiment to the next, entrapment of air bubbles in the pad, and electrode polarization. However, even with careful preparation of the pads, the results are not fully satisfactory and reproducible since parameters such as streaming potential, conductivity, and permeability are frequently time-dependent, and can change considerably even during the rinsing of the fibers with the test solution. This may be ascribed to several factors such as the changes in the state of surface hydration, rearrangement of surface layers, and desorption of surfactants, lipids, polymers, etc.

Another physical phenomenon which can be used for the characterization of the fiber surface and the process of adsorption is the flow of solvents through the fiber plugs. Specific surface area and specific volume of fibers can be calculated from the dependence of the flow rate at various porosities of a fiber plug according to, for example, the Kozeny-Carman equation (J. Jachowicz, M. Berthiaume and M. Garcia, Coll. Polym. Sci., 263,847 (1985).

It has also been well established that adsorbed polymer or surfactant layers can have a considerable effect on liquid flow through capillaries, capillary arrays or porous membranes. Both experimental and theoretical studies have been published demonstrating the reduction in flux of solvent when polymer is adsorbed on the wall of a flow channel (Y. Cohen and A. B. Metzner, "Adsorption effects in the flow of polymer solutions through capillaries" Macromolecules, 15(5), 1425 (1982); M. A. Cohen Stuart, F. H. W. H. Waajen, T. Cosgrove, B. Vincent, and T. L. Crowley, "Hydrodynamic thickness of adsorbed polymer layers", Macromolecules, 17(9), 1825 (1984); F. W. Rowland and F. R. Elrich, "Flow rates of polymer solutions through porous disks as a function of solute", I. Method, J. Polym. Sci., Part A-1,4,2033 (1986); F. W. Rowland and F. Elrich, "Flow rates of polymer solutions through porous disks as a function of solute. II. Thickness and structure of adsorbed polymer films", J. Polym. Sci., Part A-1,4,2401 (1966). The measurements of the flow of solvent can be used to estimate the effective thickness of the adsorbed layer δa by using the following relation:

$$\frac{\delta a}{R} = 1 - \left(\frac{Qa}{Q}\right)^{\frac{1}{4}}$$

where Q and Qa are the flow rates before and after adsorption, respectively, and R is the radius of a channel through which the solvent is passed. For a plug of fibers, whose geometry can be treated in approximation as cylinders, the mean hydraulic radius of channels can be calculated form the following equation (W. L. McCabe, J. C. Smith, Unit Operations of Chemical Engineering, McGraw-Hill Book Company, 1976, pg. 148):

$$R_H = \frac{\epsilon}{1-\epsilon} \frac{r}{2}$$

where r is the radius of a cylinder (radius of hair) and $\epsilon$ is porosity defined as a ratio of the volume of voids to the total volume of the plug. Porosity, in fibers, may be changed by compression of the plug. This would change the mean hydraulic radius of channels.

Treatments of fibers, such as, for example, cosmetic compositions, result in deposition of polymers, surfactant, surfactant-surfactant, polymer-polymer, and surfactant-polymer complexes on the fiber surface. The thickness of adsorbed layers is frequently considerable, and it can have a significant effect on the rate of the flow of solvents through the plug. As shown above, measurements of the flow rate can give information about the process of adsorption. In addition to this, the streaming potential of the fiber plug is also dependent on the flow rate of the test solution.

OBJECTIVES AND FEATURES OF THE INVENTION

It is an objective of the present invention to provide a system and method for the measurement of streaming potentials which are accurate over a series of experiments so that the results of those experiments may be compared and which is automatically operated and computer-based to reduce the adverse effects of operator error.

It is a further objective of the present invention to provide such a system and method for analysis of the dynamics of changes in the ionic character of a permeable sample, a typical sample being the fiber surface of a plug of hair, under a controlled flow of aqueous solutions including solutions of salts, surfactants, polymers and nonaqueous solvents, to compare the affinity of various colloids to the fiber surface and thereby to predict the performance of such solutions as cleaning or conditioning agents.

It is a further objective of the present invention to provide a new instrument for performing simultaneous electrokinetic and permeability measurements in fiber plugs. In order to alleviate the sources of irreproducibility related to pad formation, and to obtain additional information about the kinetics of the sorption and desorption processes, streaming potential, conductivity, and permeability, measurements are performed in a dynamic mode (as a function of rinsing time) before and after on-line treatments with various active agents.

It is a further objective of the present invention to provide such a system and method for such analysis of a fiber surface to determine the effect on the surface and bulk properties of the fiber of (i) cationic surfactants, cationic polymers, proteins and low molecular weight organic compounds; (ii) reactive treatments, including hair waving treatment, bleaching and dyeing; and (iii) treatment with multicomponent liquids, such as commercially available hair conditioning shampoos and conditioners.

It is a further objective of the present invention to provide such a system and method to enhance understanding of the dynamics of the interaction of charged colloids with hair, such colloids including shampoos, conditioners and temporary hair dyes.

BRIEF DESCRIPTION OF THE DRAWINGS

Other objectives of the present invention will be apparent from the following detailed description, taken in conjunction with the accompanying drawings.

In the drawings.

SUMMARY OF THE INVENTION

Figure 1:
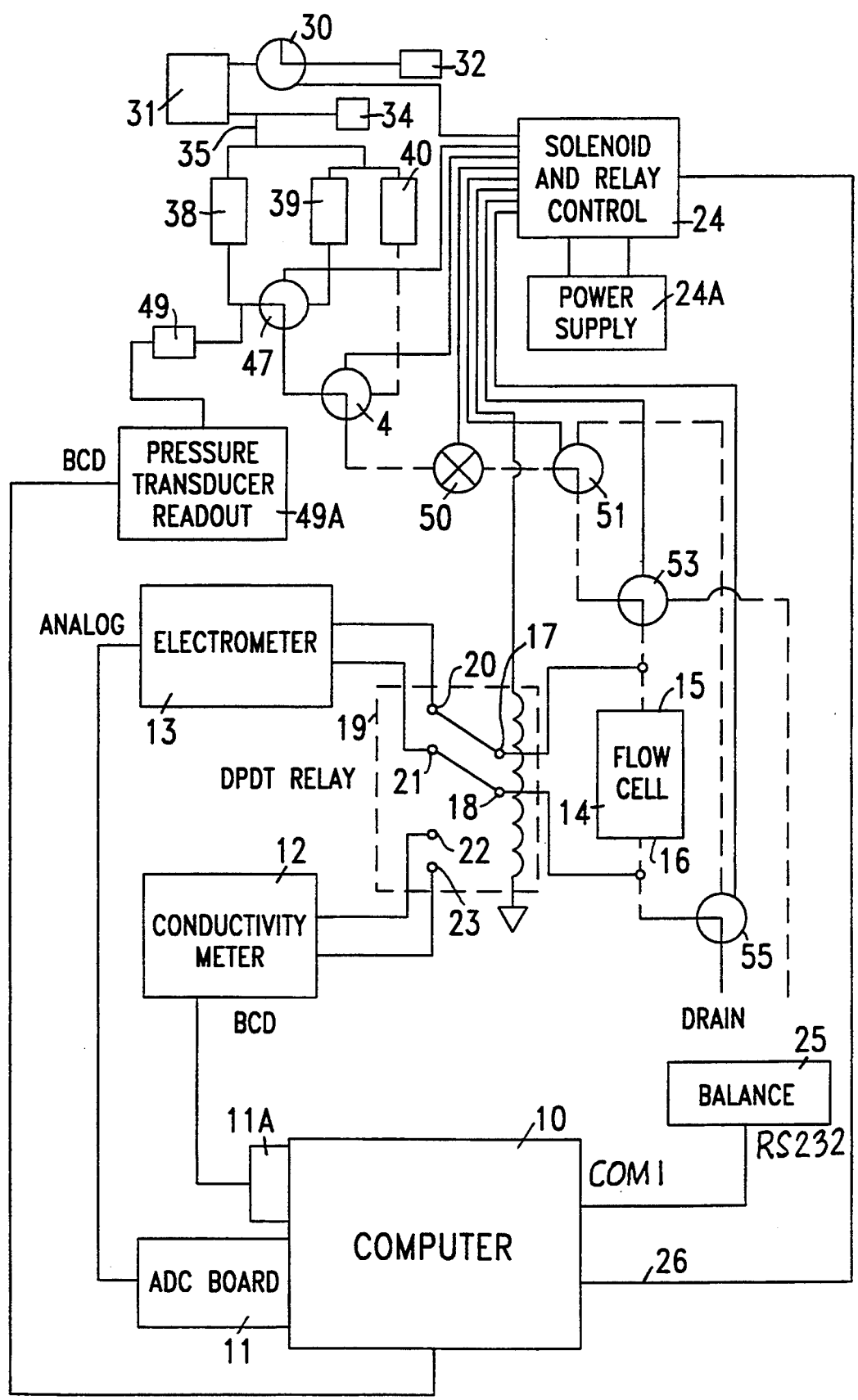
FIG. 1 is a block diagram of a portion of the system of the present invention showing the computer control system.

In accordance with the present invention there is provided a method and system for measuring streaming potentials, conductivity and permeability (flow rate) measurements. The system and method will be described in connection with a plug of human hair fibers as an embodiment; although the system and method may be used in the measurement of other fibers and other porous materials.

The system comprises a series of reservoirs, for example, a reservoir of a test solution (to test the system and the sample) and first and second treatment reservoirs, holding first and second treatment liquids. A source of compressed air is connected by an air line to these reservoirs to maintain a constant pressure on the liquids. The reservoirs are connected, by fluid flow lines, through a set of computer actuated solenoid valves, to the inlet orifice of a flow cell. The outlet orifice of the flow cell is connected to a drain. The system may pump the various liquids, preferably in pulses, through the flow cell in both forward and backward directions.

The flow cell has perforated electrode disks at its opposite ends and a fiber plug is positioned between the electrode disks. The electrode disks are electrically connected to a pair of contacts which are switched by a relay, under digital computer control, from a pair of contacts electrically connected to an electrometer to a second pair of contacts electrically connected to a conductivity meter.

The electrometer and conductivity meter, as well as a pressure transducer read-out meter (to measure the liquid pressure) and the solenoid valves are connected to a digital computer. The digital computer, under software (program) control, operates the valves and collects the data from the various meters. The meters may be digital, but if the meters are analog meters their outputs are converted to digital data by an analog/digital converter board plugged into the computer.

In operation, the user will load the flow cell with a sample of fibers, for example, a plug of human hair. The system will, in a dynamic mode, measure the streaming potential, conductivity and permeability of the sample. The system, under software control, will automatically apply a series of pulses of dilute test solution of a neutral salt through the test cell. The flow and the potential are measured with the on-off pulsed flow to provide a measure of the background noise. Then the test solution is flowed through the test cell in one direction and potential measurements are taken. Then the first treatment solution is flowed through the test cell, in pulses, to provide an on-line treatment of the hair, and streaming potential, conductivity and permeability are measured. The hair may be retreated, on-line, with the same treatment solution or with a second treatment solution, by applying pulses of the retreatment solution through the hair. Then the test solution is again flowed through the flow cell, in pulses, and data is recorded. The entire procedure is computer-controlled and without operator intervention.

DETAILED DESCRIPTION OF THE INVENTION

As shown in FIG. 1, the measurement system of the present invention includes a software program controlled digital computer 10, such as an IBM P/2 PC having an analog-to-digital converter board 11 (ADC board). The computer 10 has a digital input/output board 11A having an output port to control a visual display device such as a video monitor and/or a hard copy printer. The computer 10 is electrically connected to a conductivity meter 12 which provides BCD (Binary Coded Decimal) output and which measures current. The ADC board 11 is electrically connected to electrometer 13 which measures voltage potential and which has an analog output.

A flow cell 14 is a right-sided cylinder and has two disk electrodes 15 and 16, for example, of silver. The electrode disks are perforated to allow liquid to flow through them. The electrode disks 15 and 16 are electrically connected to contacts 17 and 18, respectively, of the DPDT relay 19 (Double Pole Double Throw). The electrometer 13 is electrically connected to the contacts 17 and 18 and 20 and 21 of the relay 19. The control coil of the relay 19 is electrically connected to the solenoid and relay control board 24, which is controlled by the computer 10 through the digital signal line 26. An electronic balance 25 is connected to the RS-232 port of the computer 10. The electronic balance is used to measure the flow rate of the solution through the cell. Alternatively, a flow meter may be used for each flow rate measurement.

Figure 2:
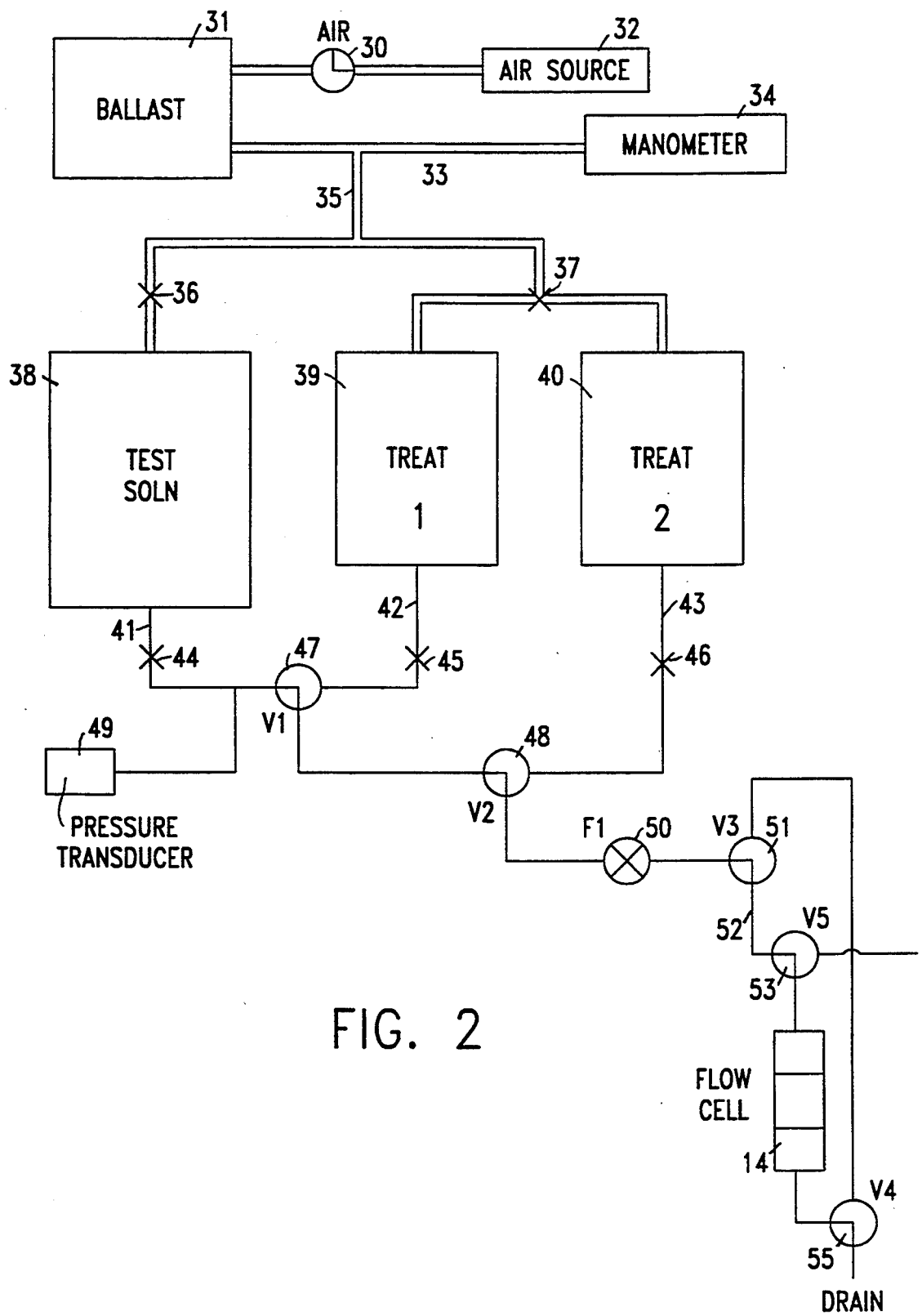
FIG. 2 is a block diagram of a portion of the system of the present invention showing the liquid flow lines.
Figure 3A:
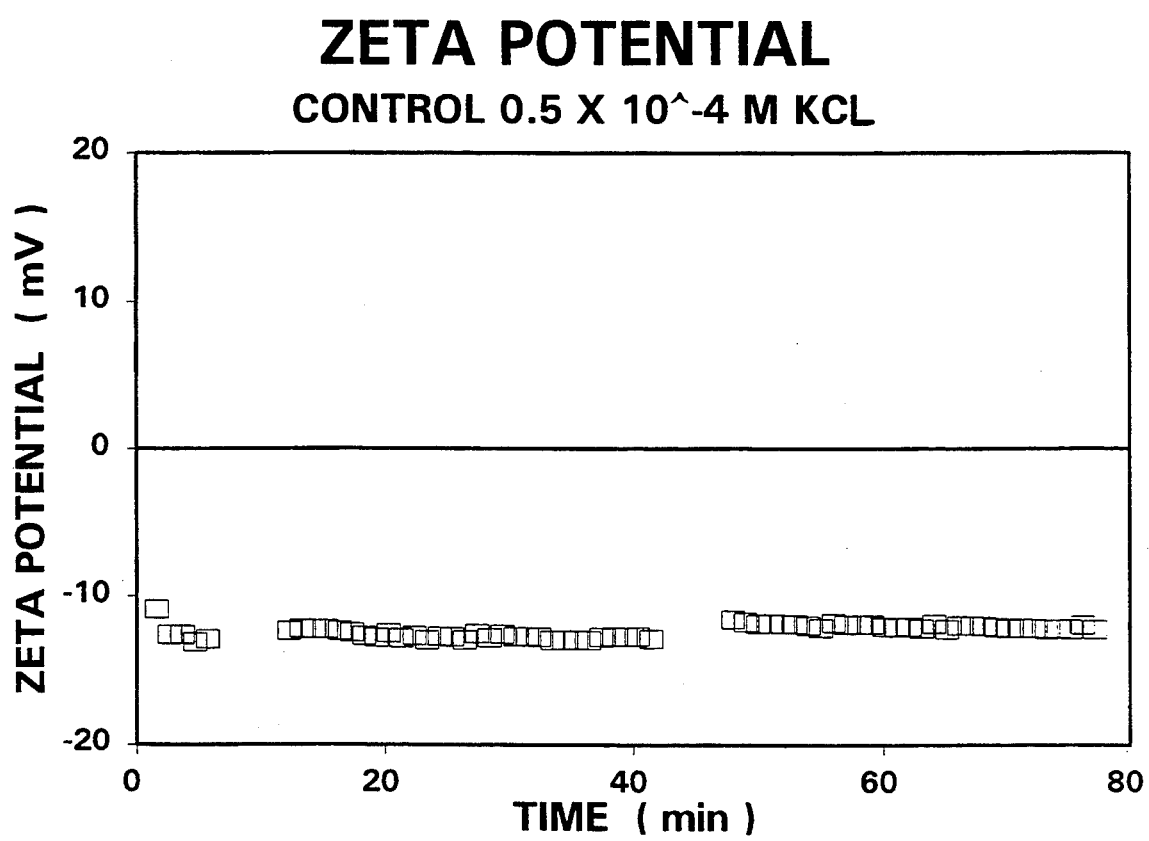
FIGS. 3a–27d are X-Y charts of zeta potential, flow rate, conductivity and streaming potential, respectively, and illustrate the results determined in described Examples 1–11.
Figure 3B:
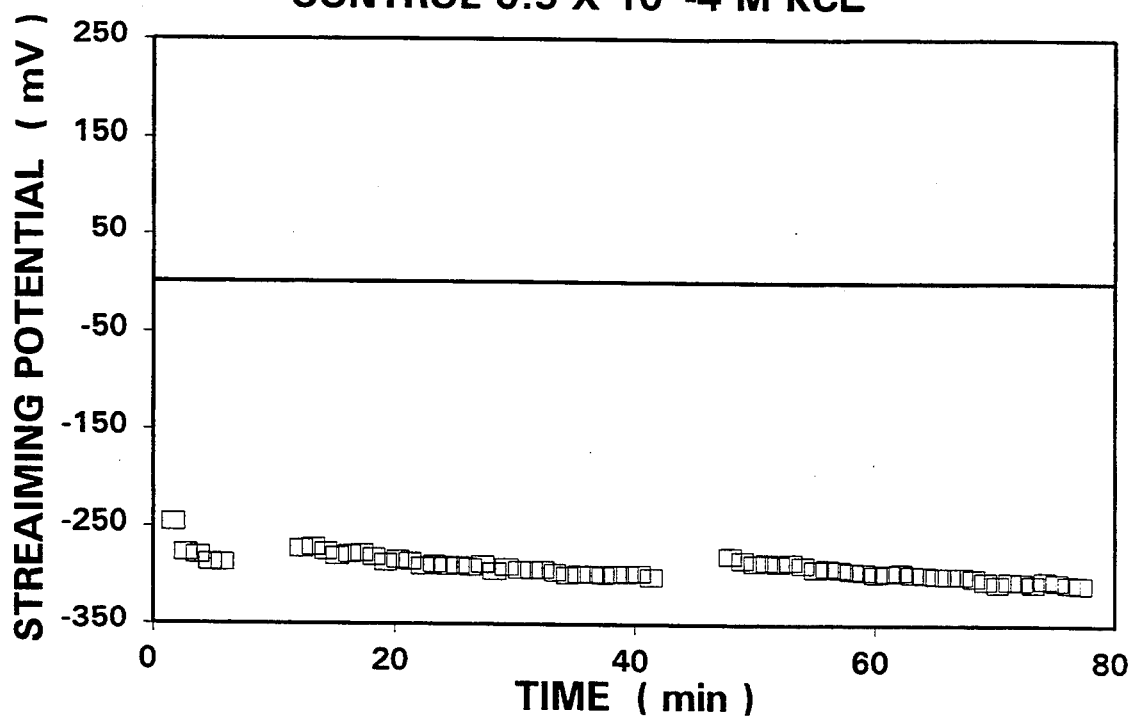
Figure 3C:
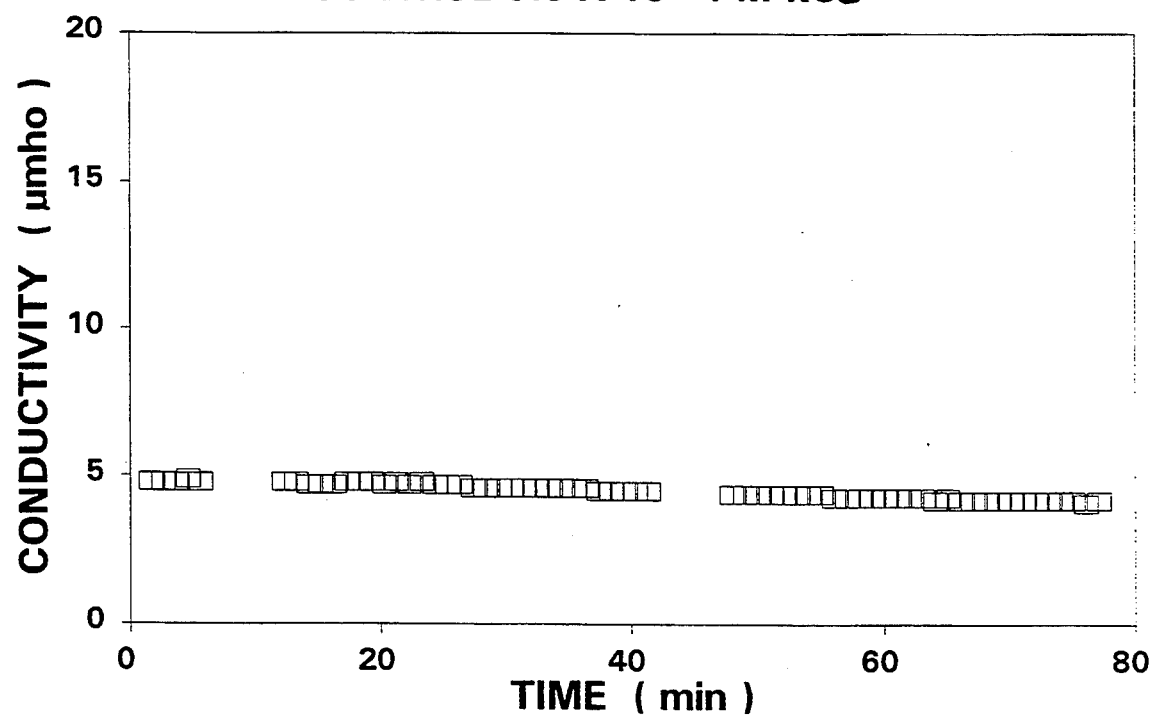
Figure 3D:
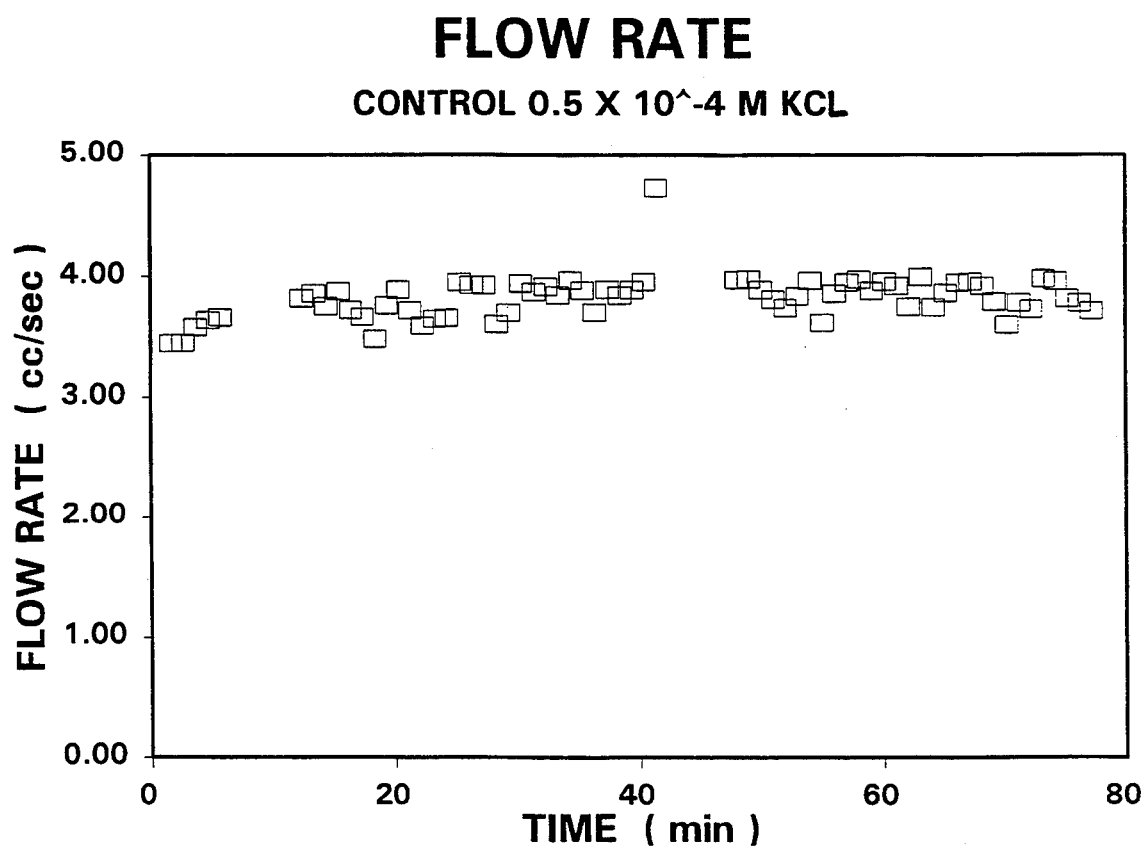
Figure 4A:
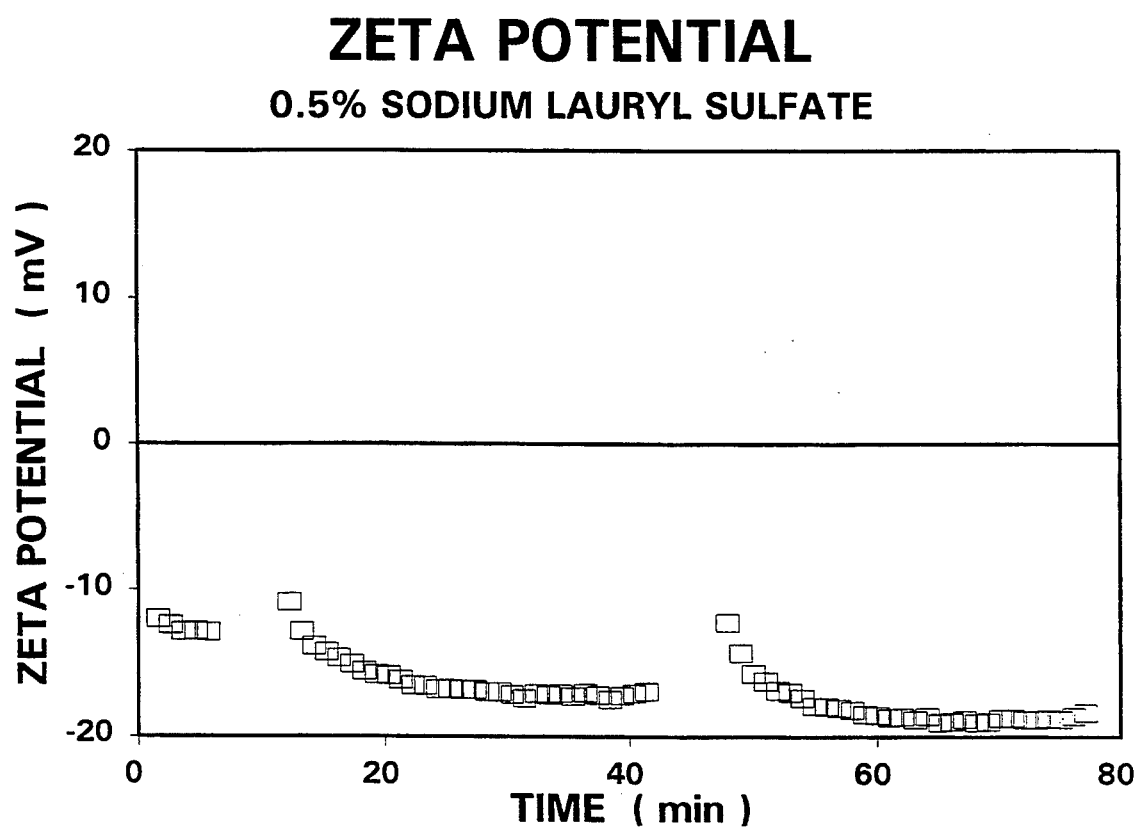
Figure 4B:
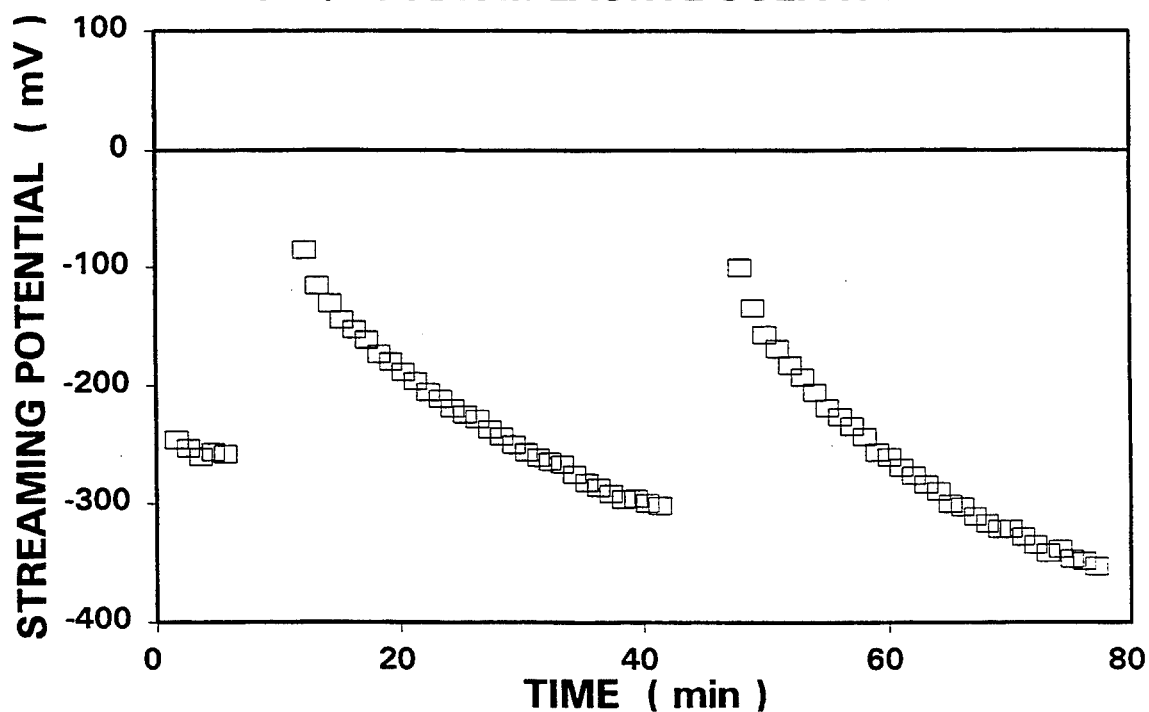
Figure 4C:
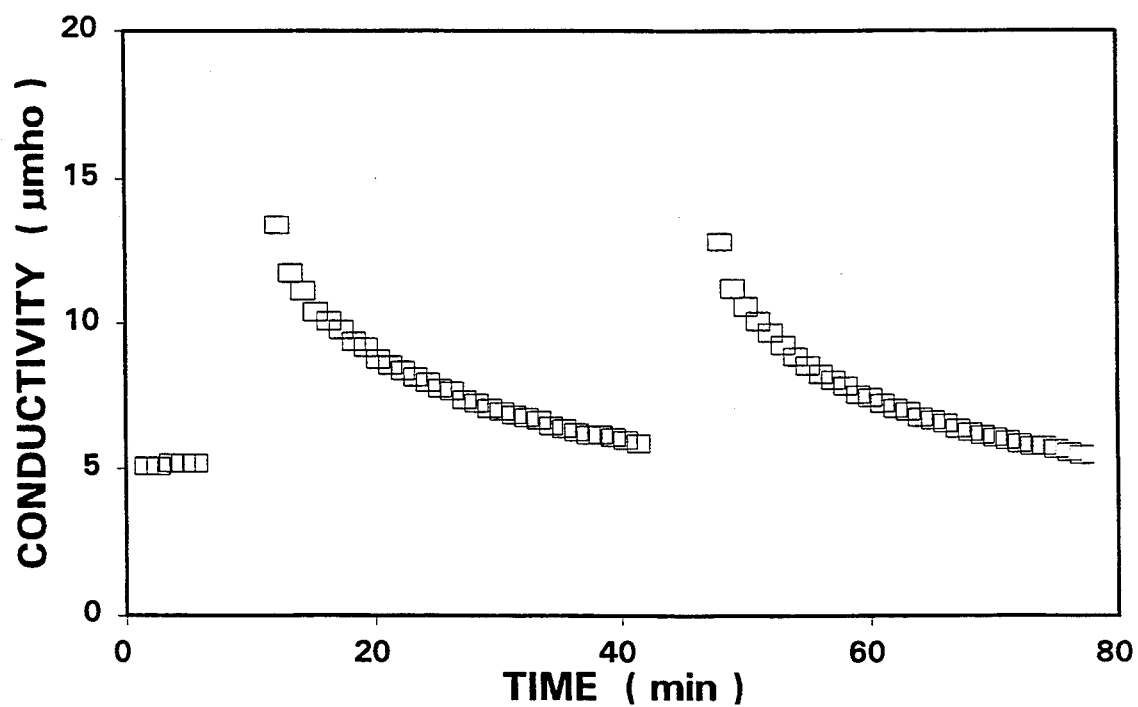
Figure 4D:
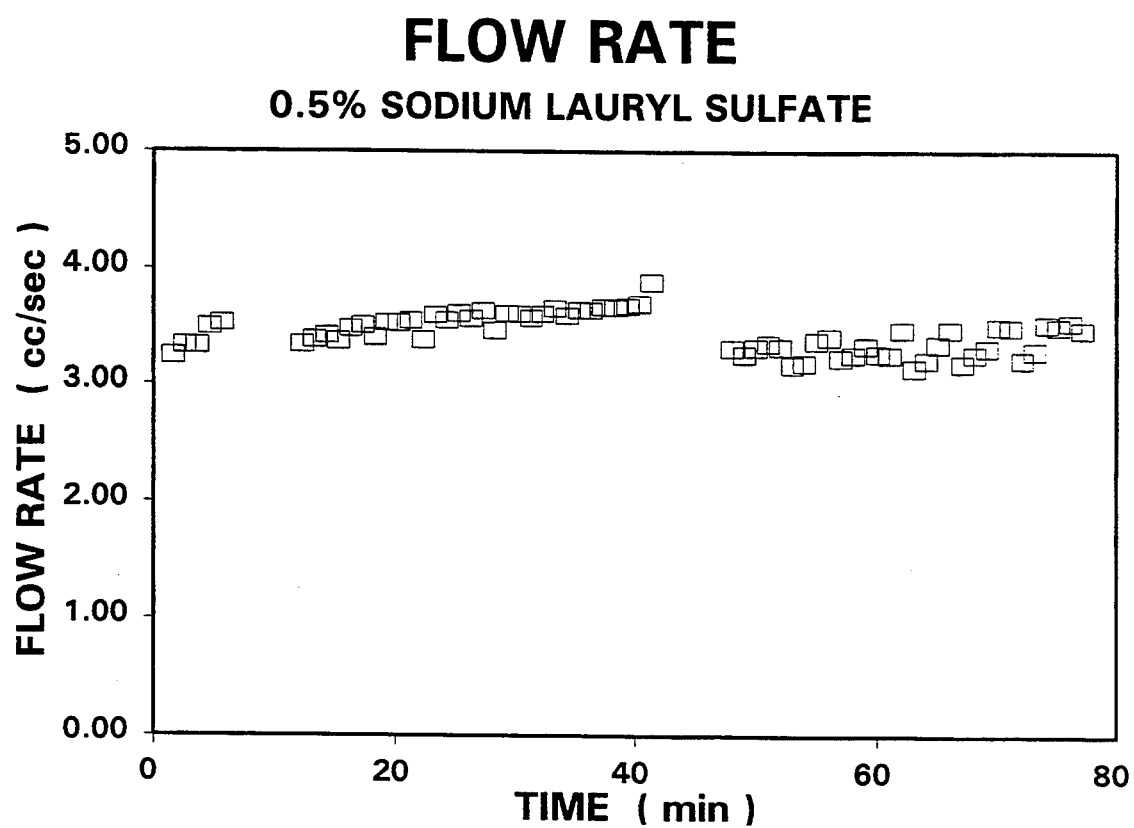
Figure 5A:
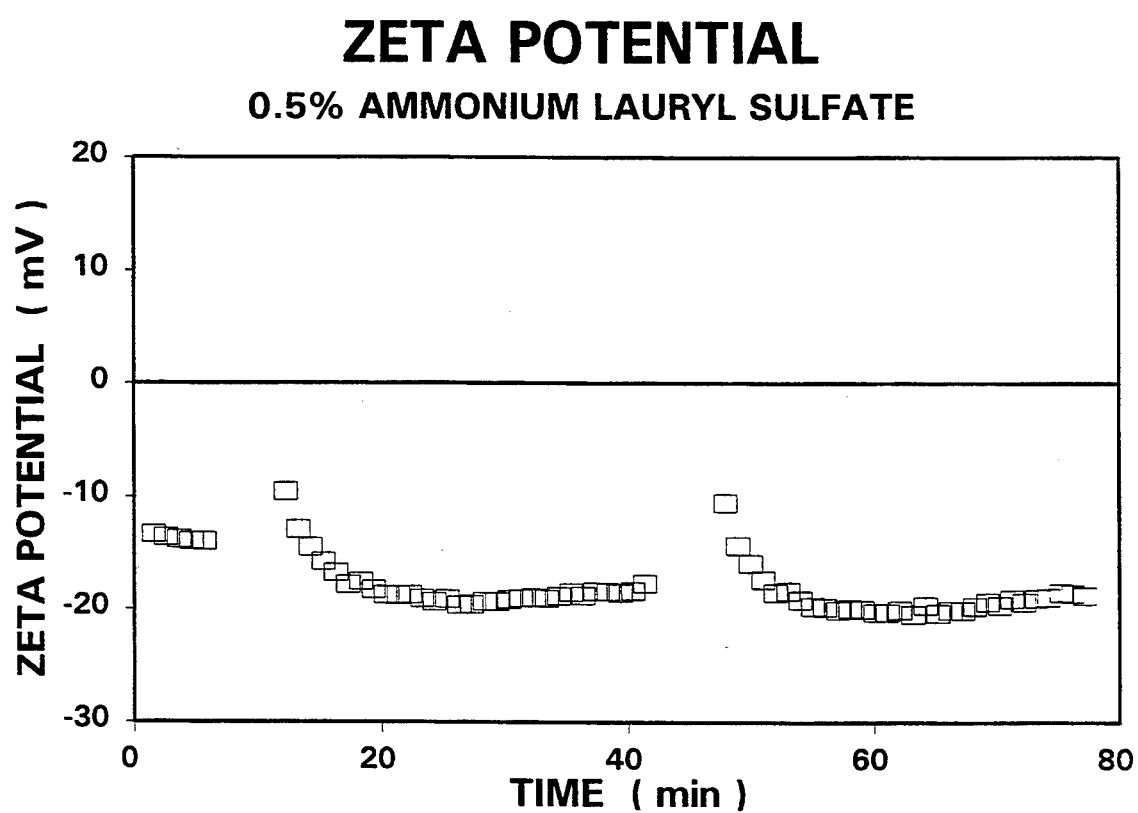
Figure 5B:
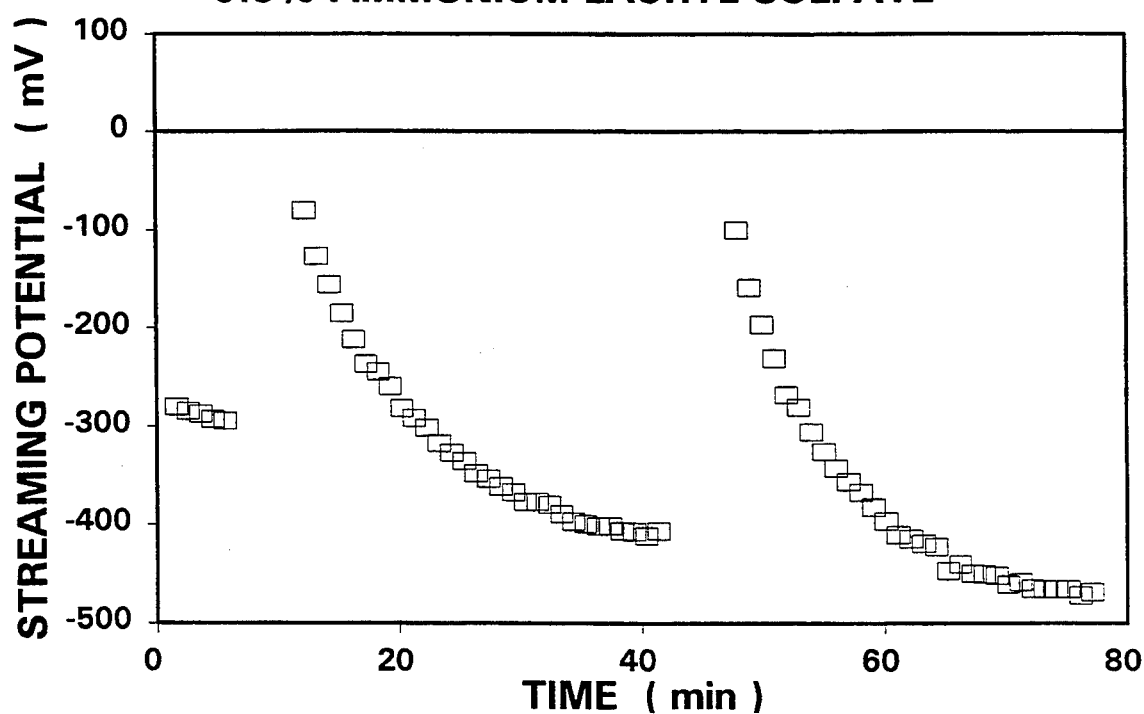
Figure 5C:
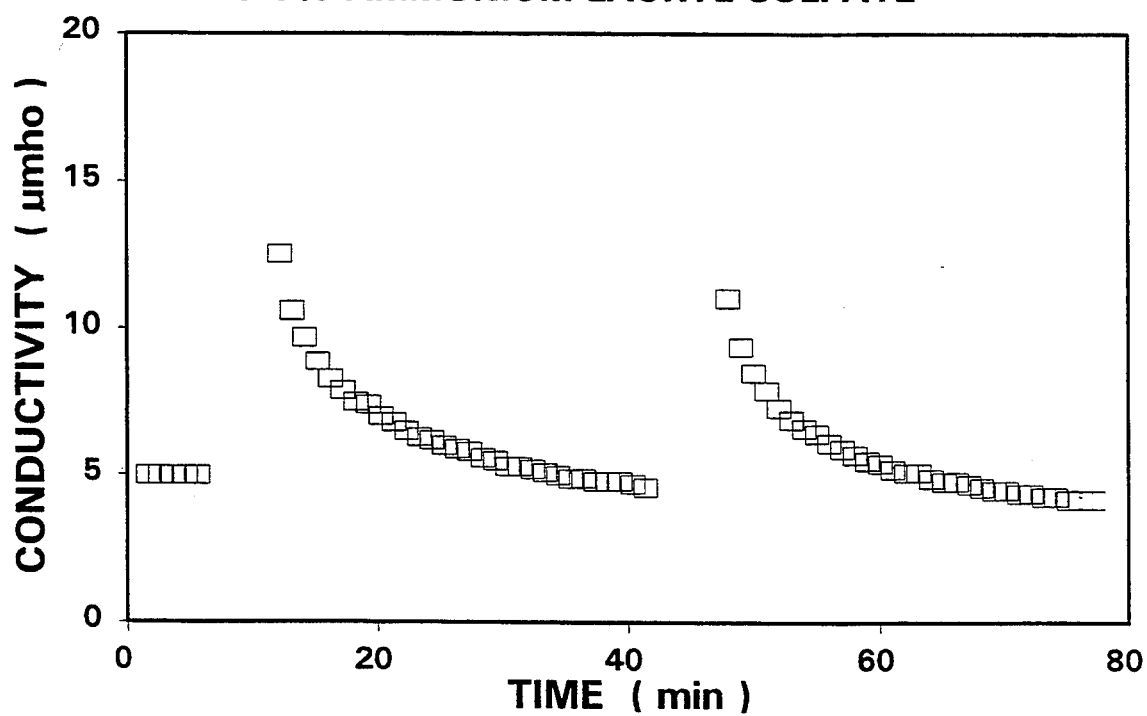
Figure 5D:
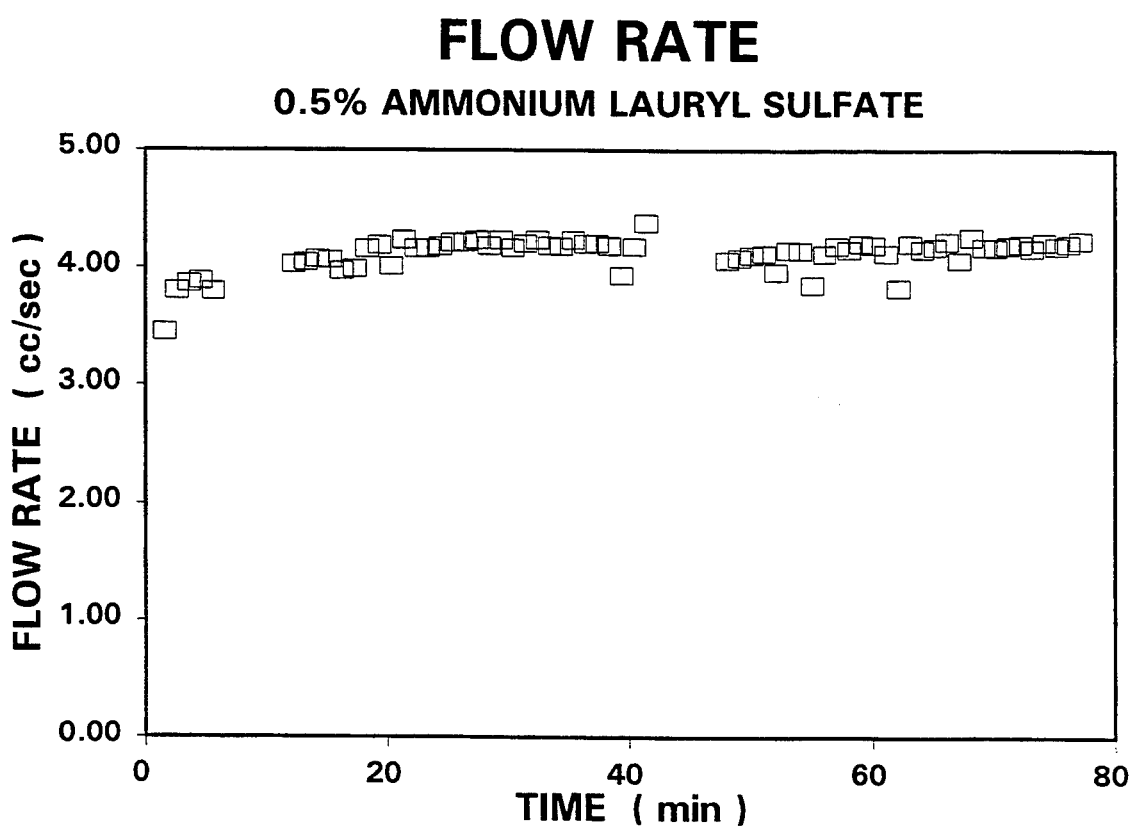
Figure 6A:
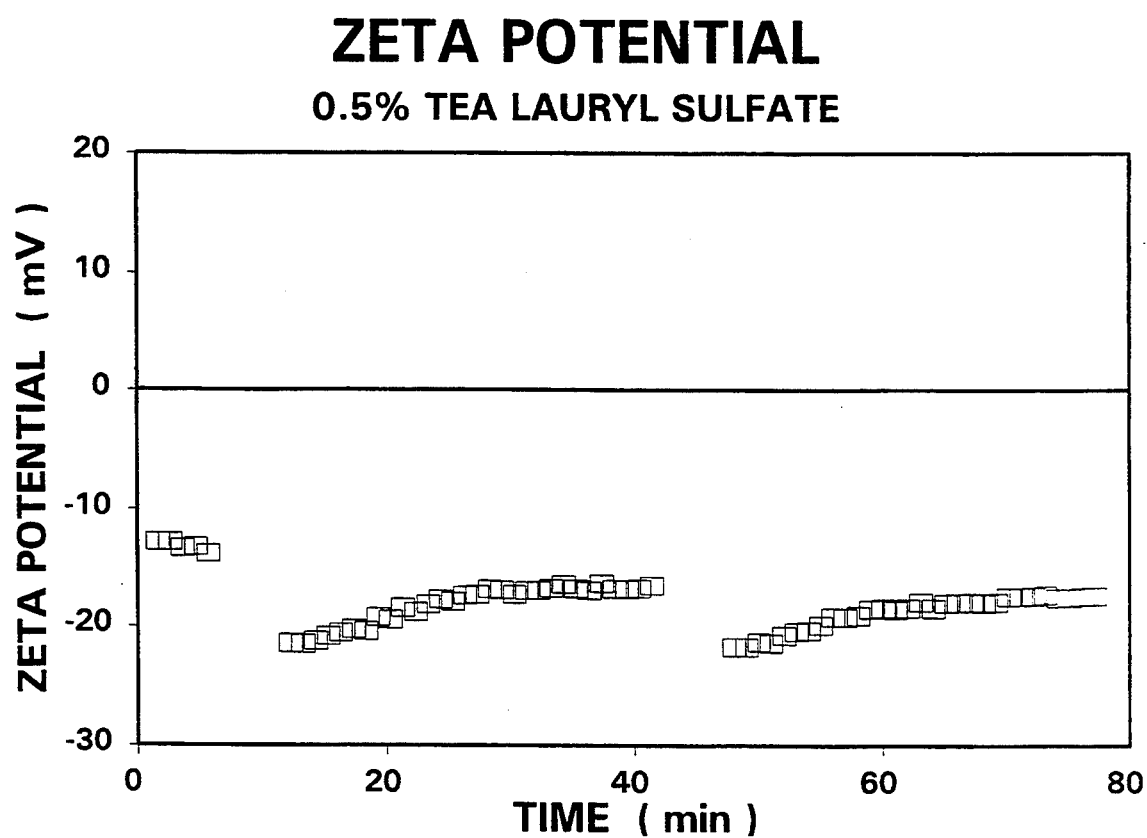
Figure 6B:
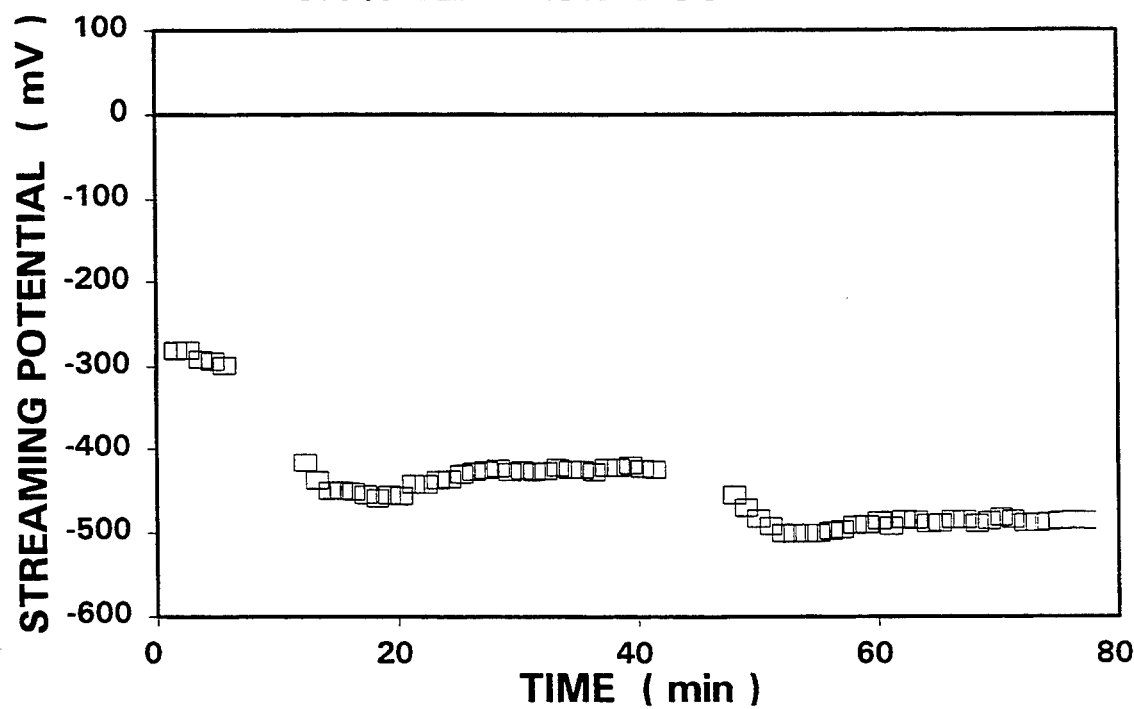
Figure 6C:
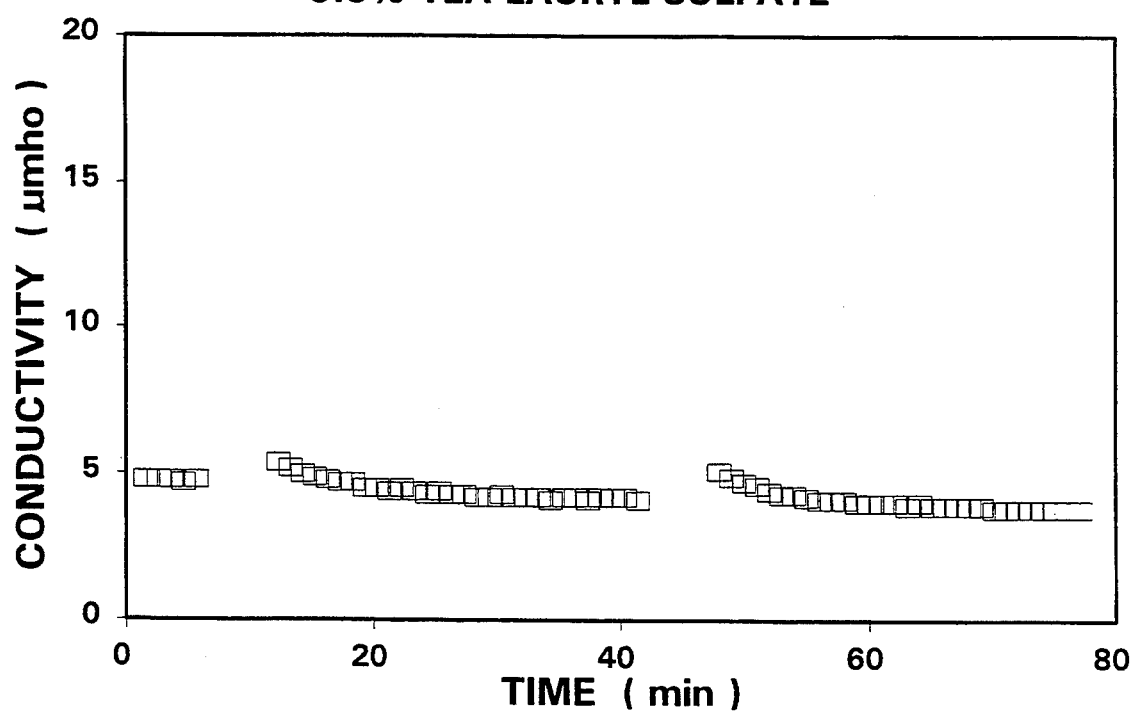
Figure 6D:
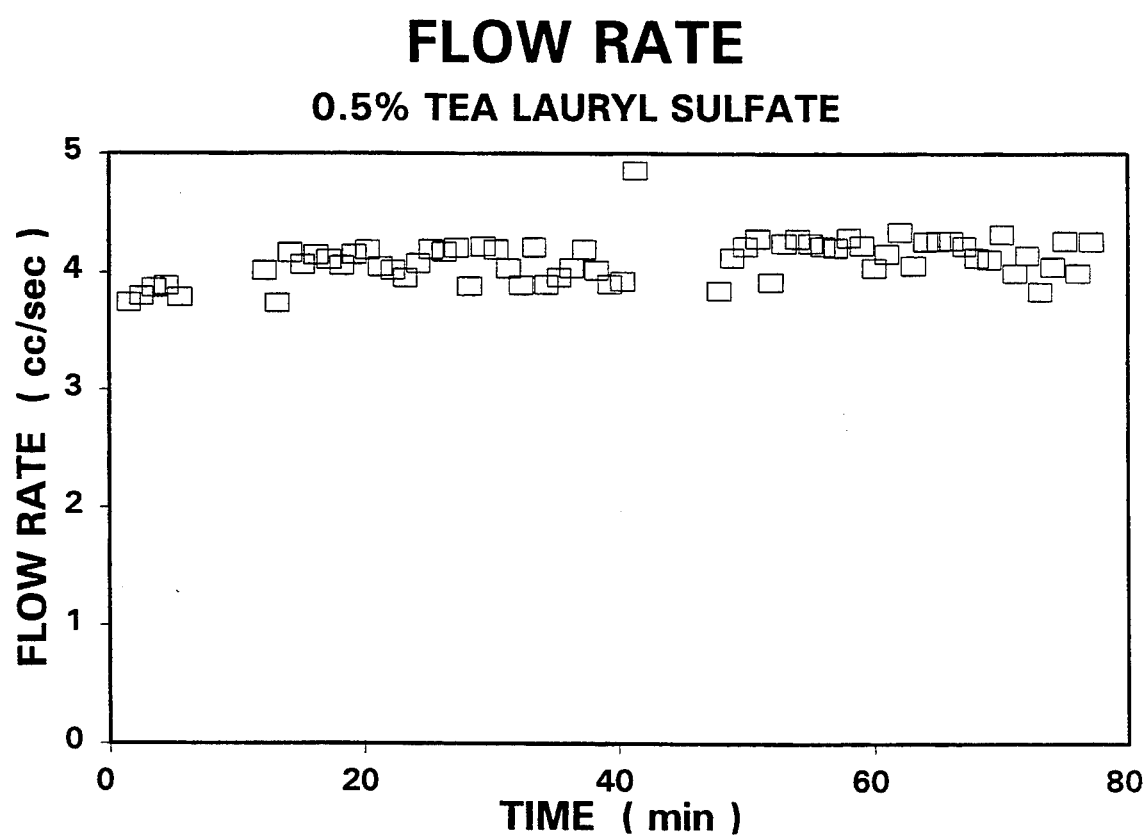
Figure 7A:
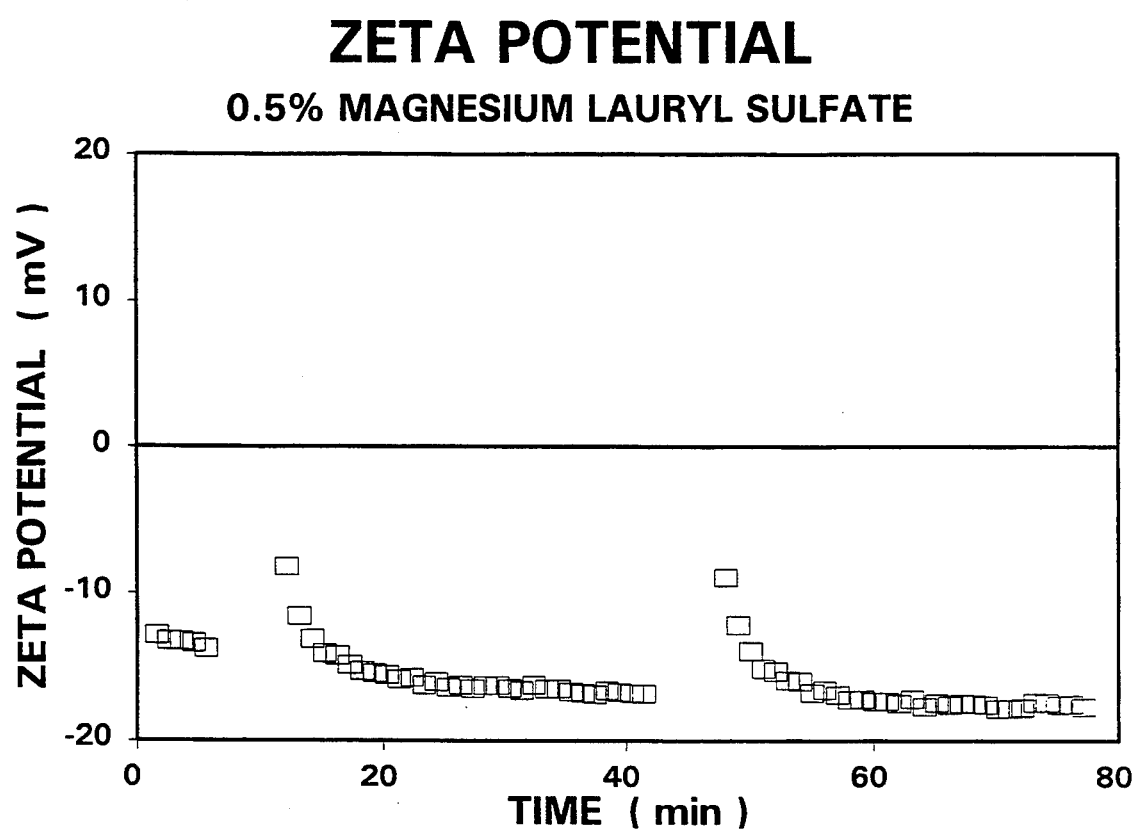
Figure 7B:
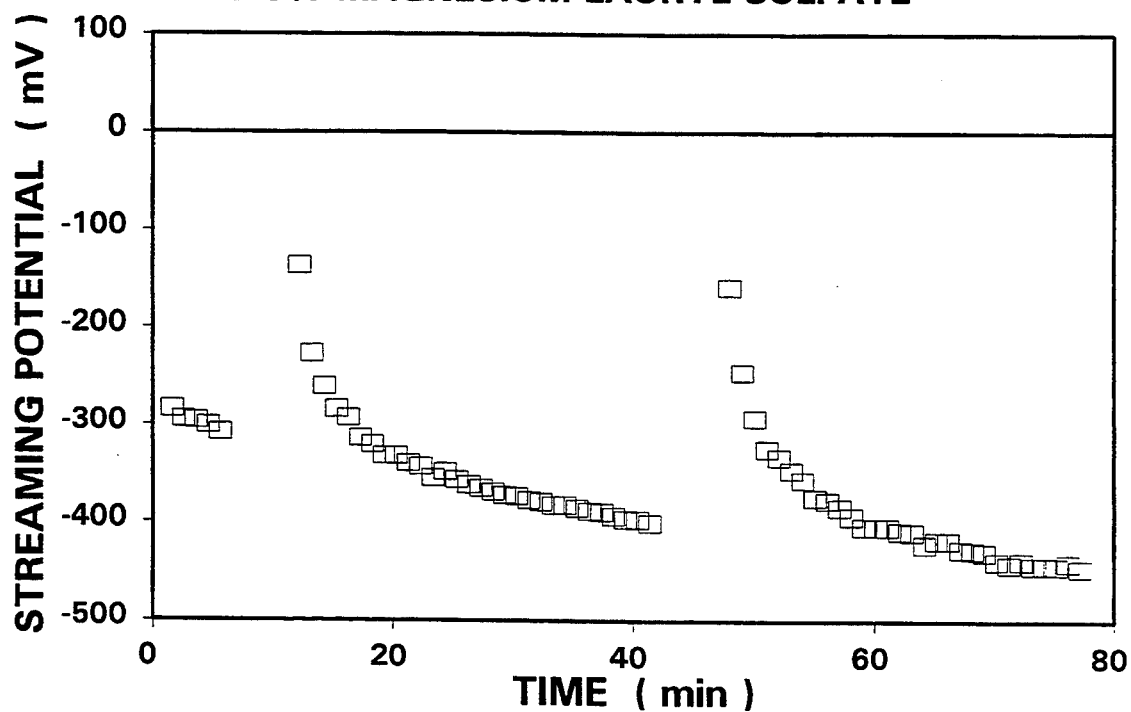
Figure 7C:
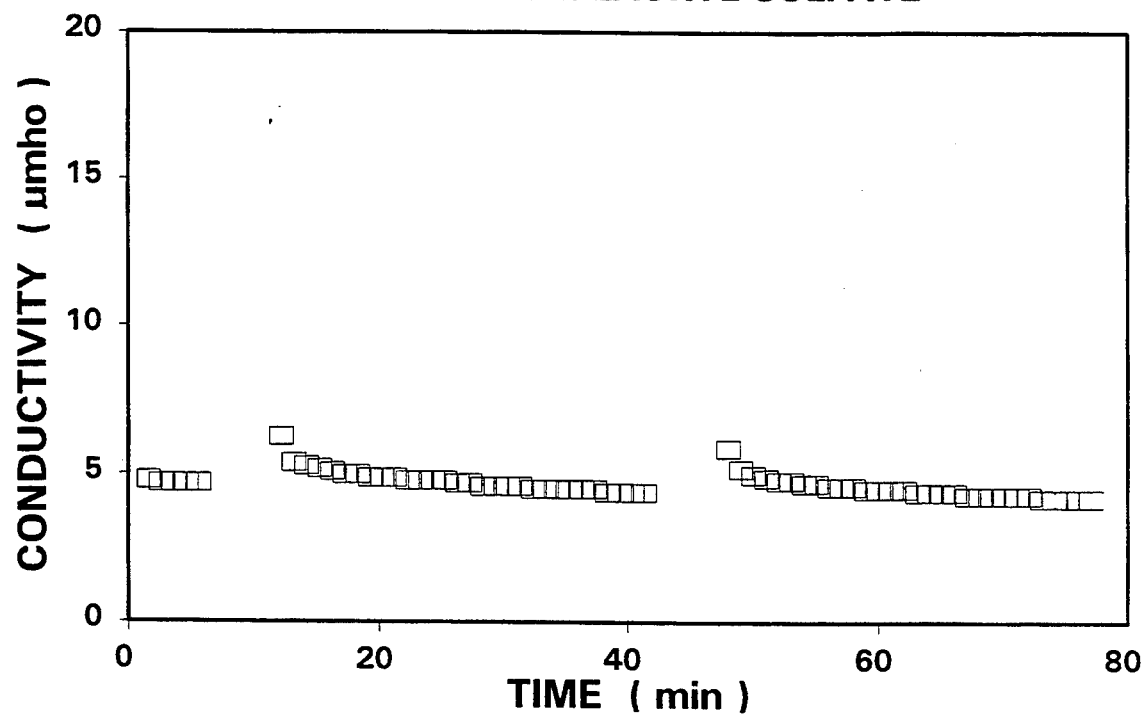
Figure 7D:
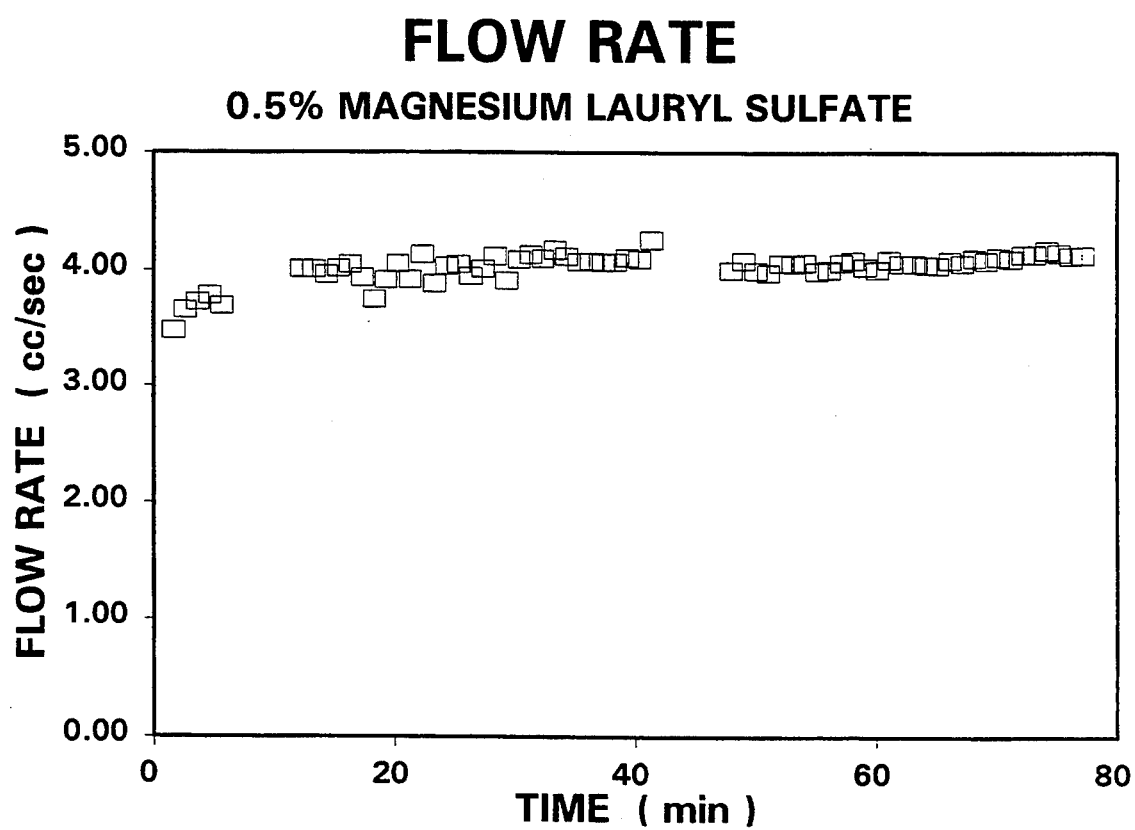
Figure 8A:
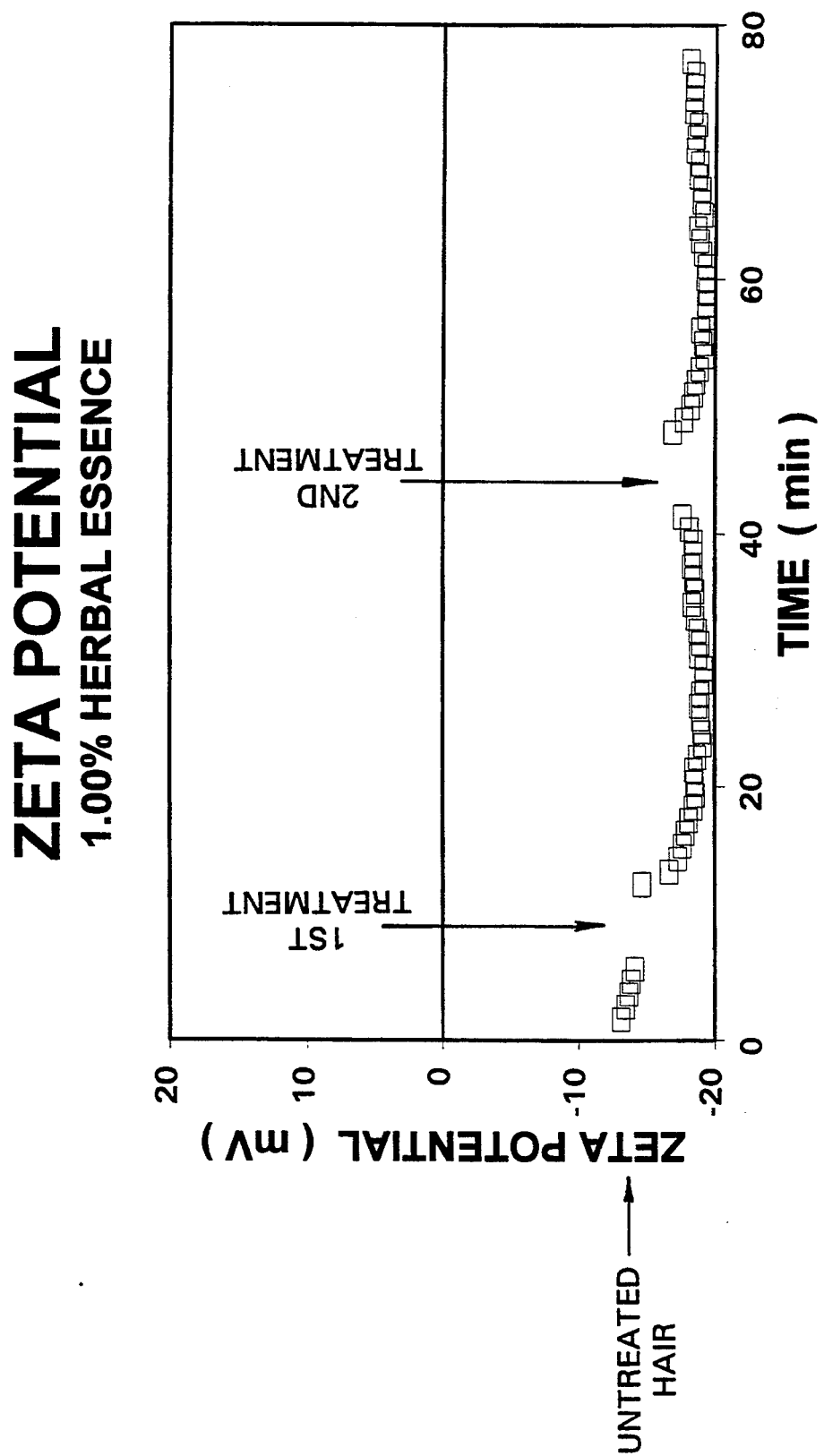
Figure 8B:
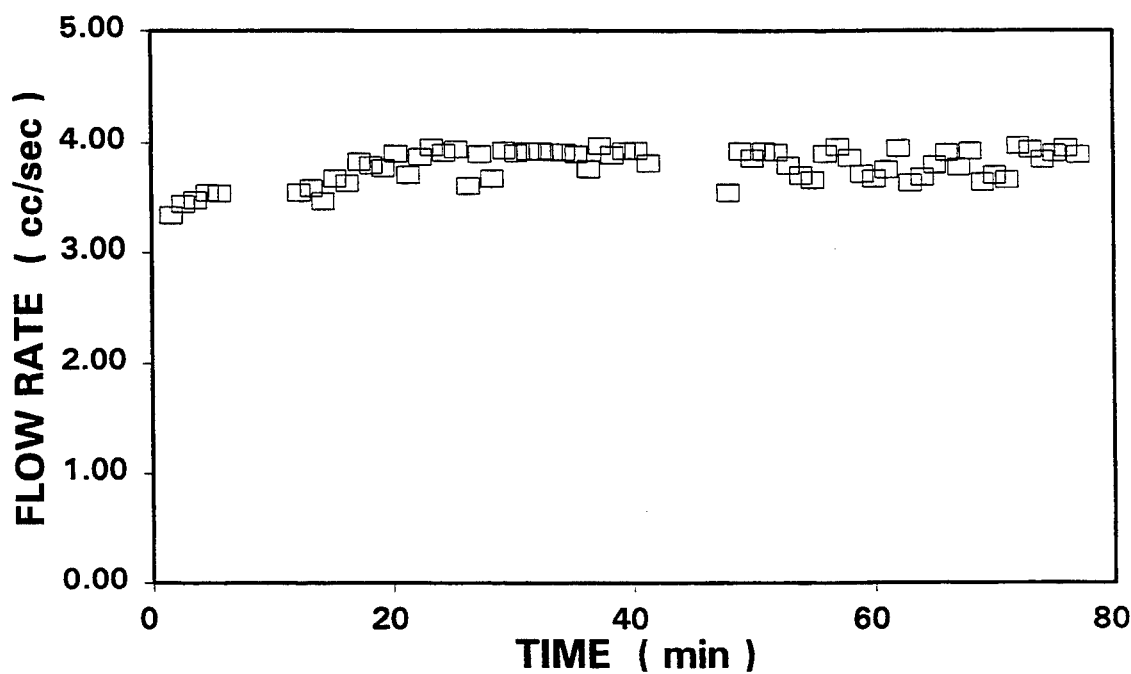
Figure 8C:
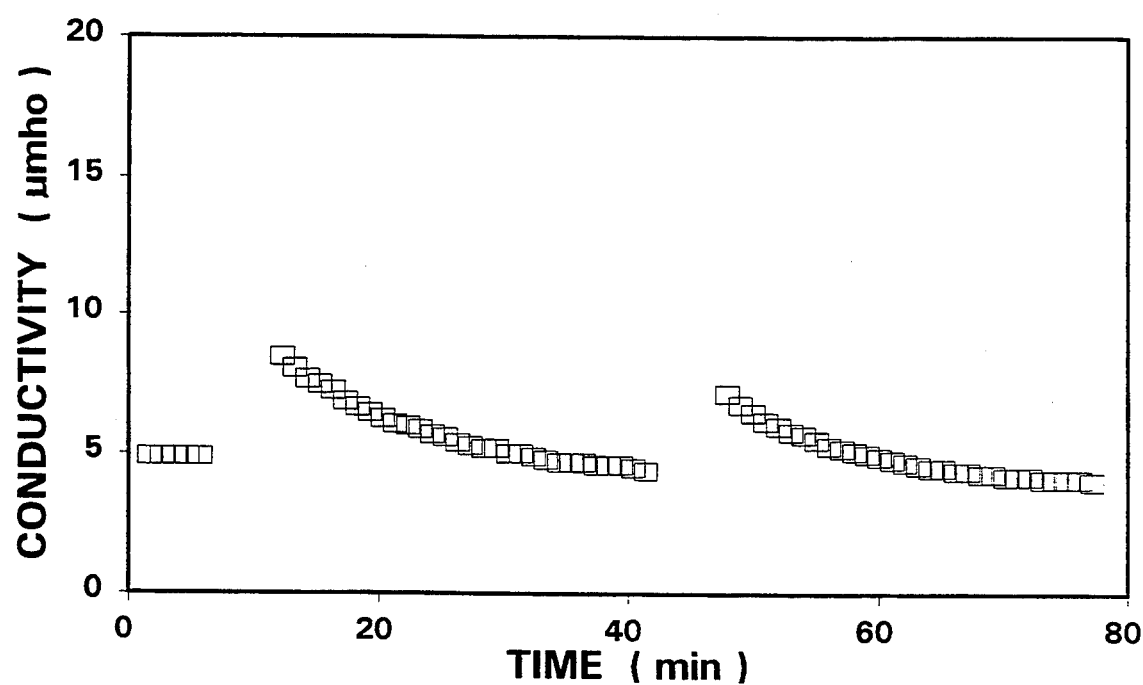
Figure 8D:
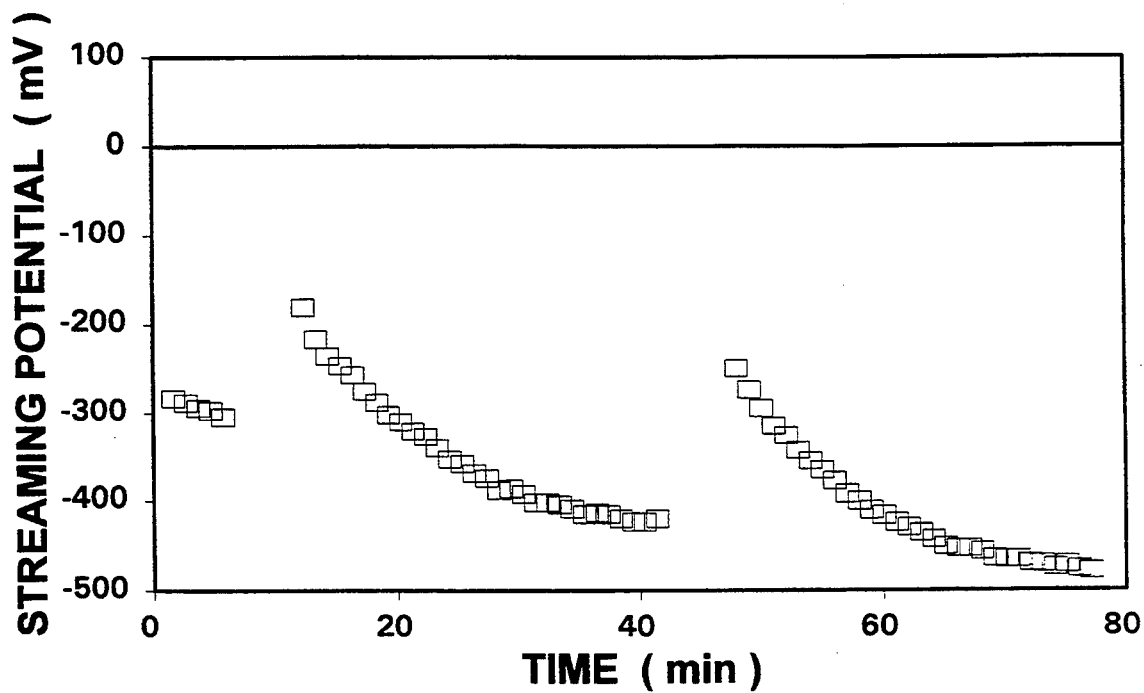
Figure 9A:
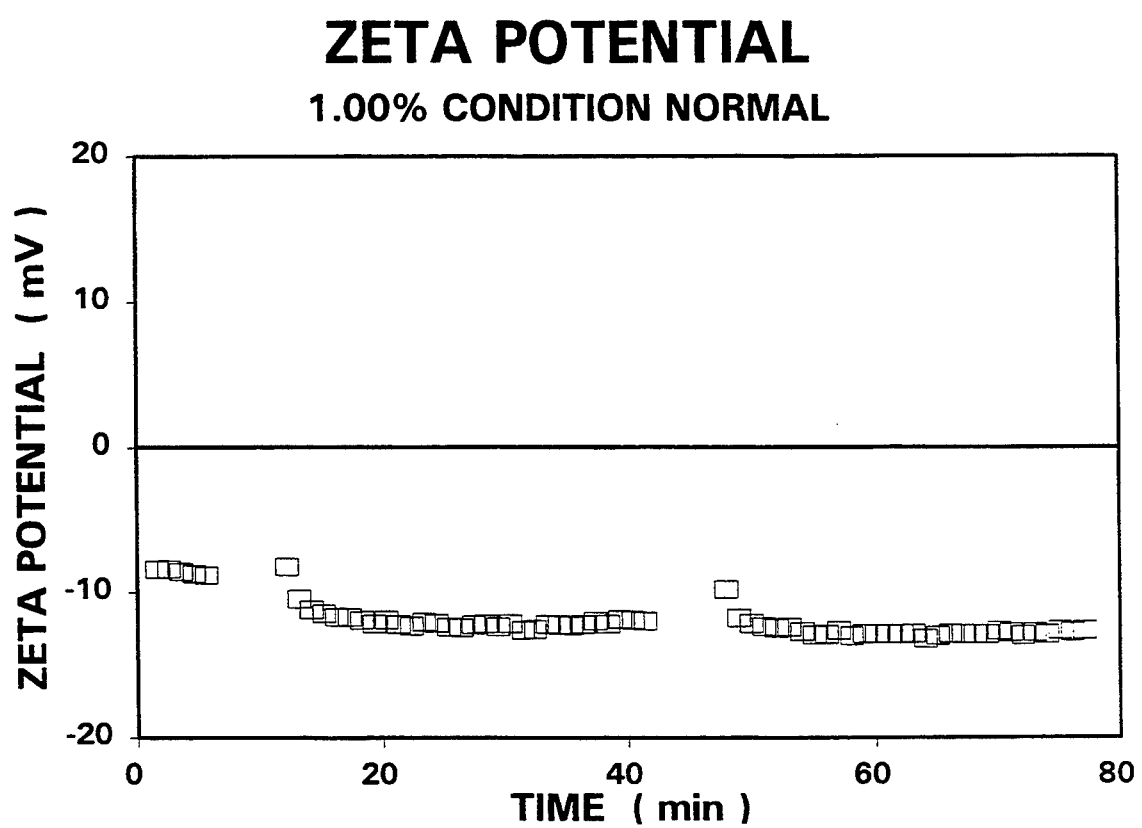
Figure 9B:
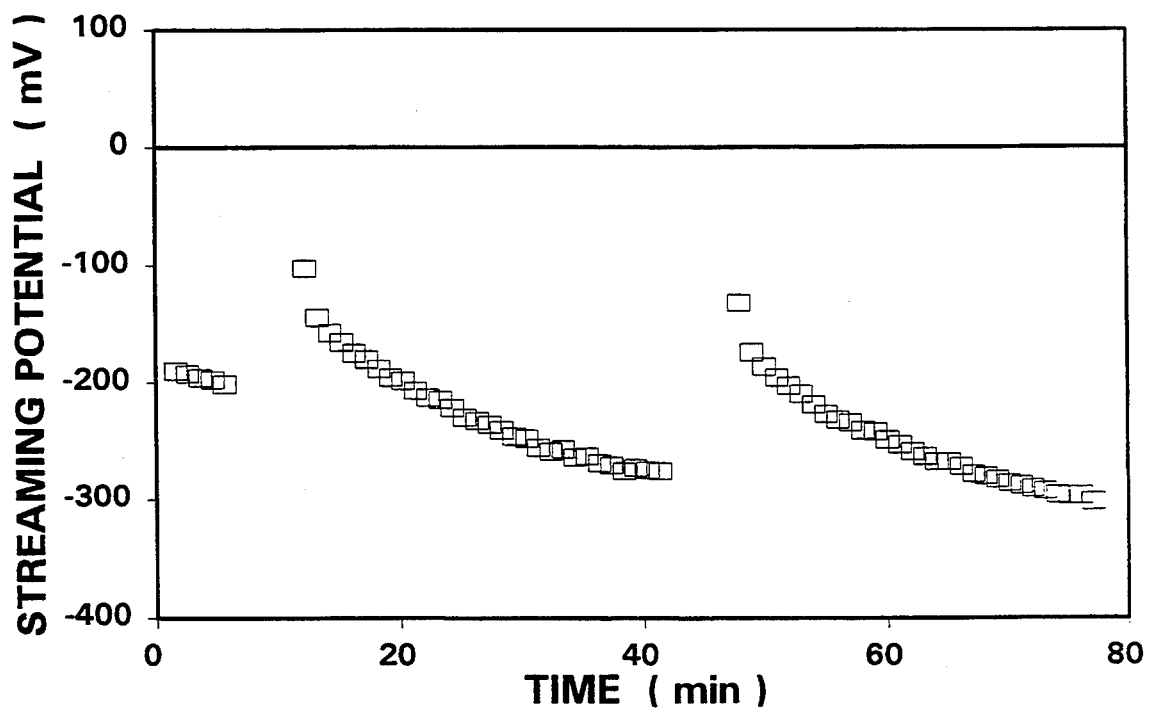
Figure 9C:
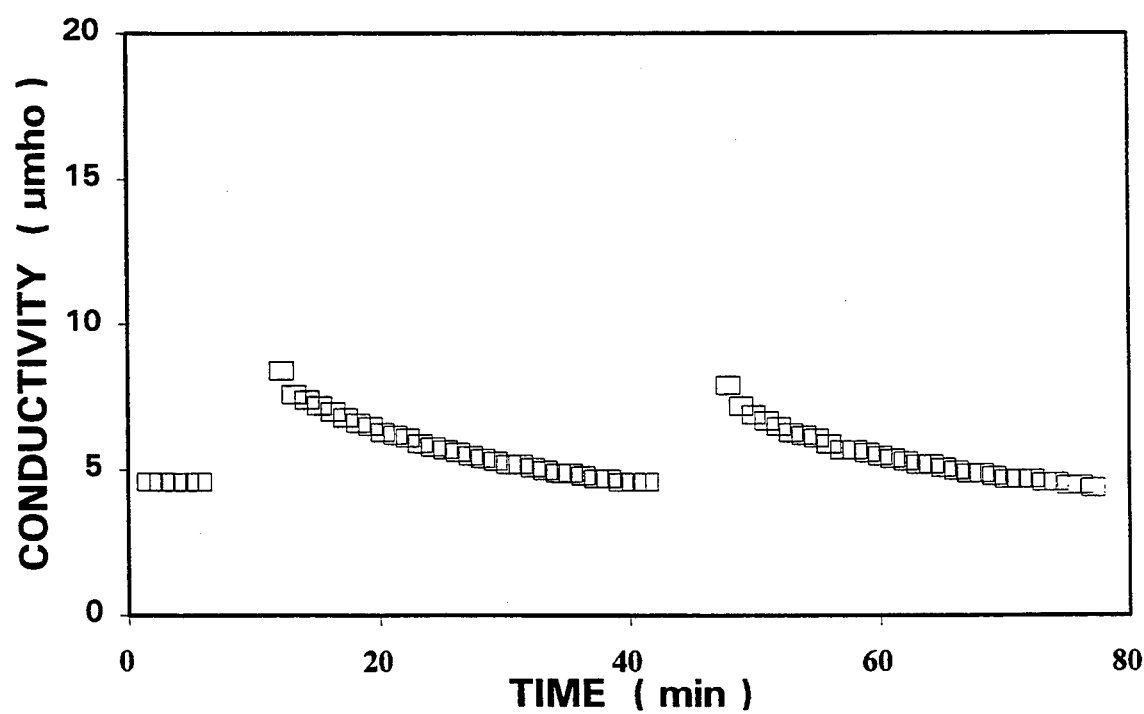
Figure 9D:
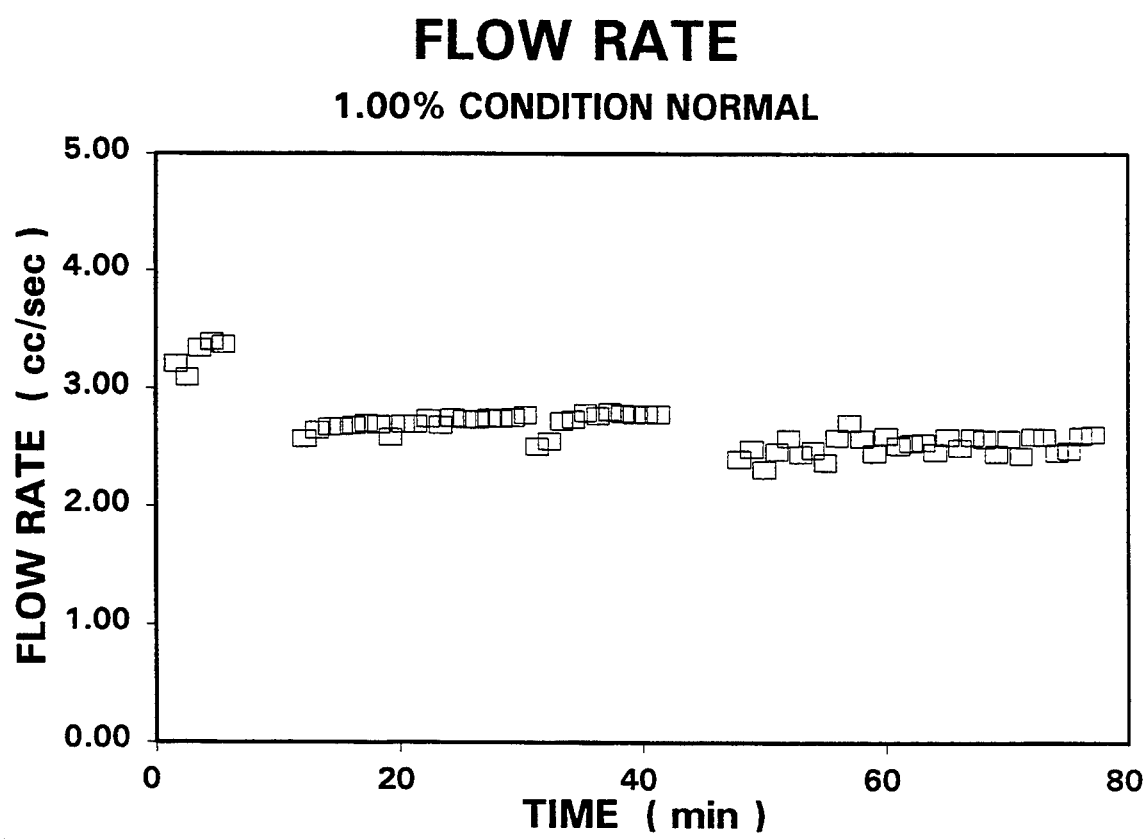
Figure 10A:
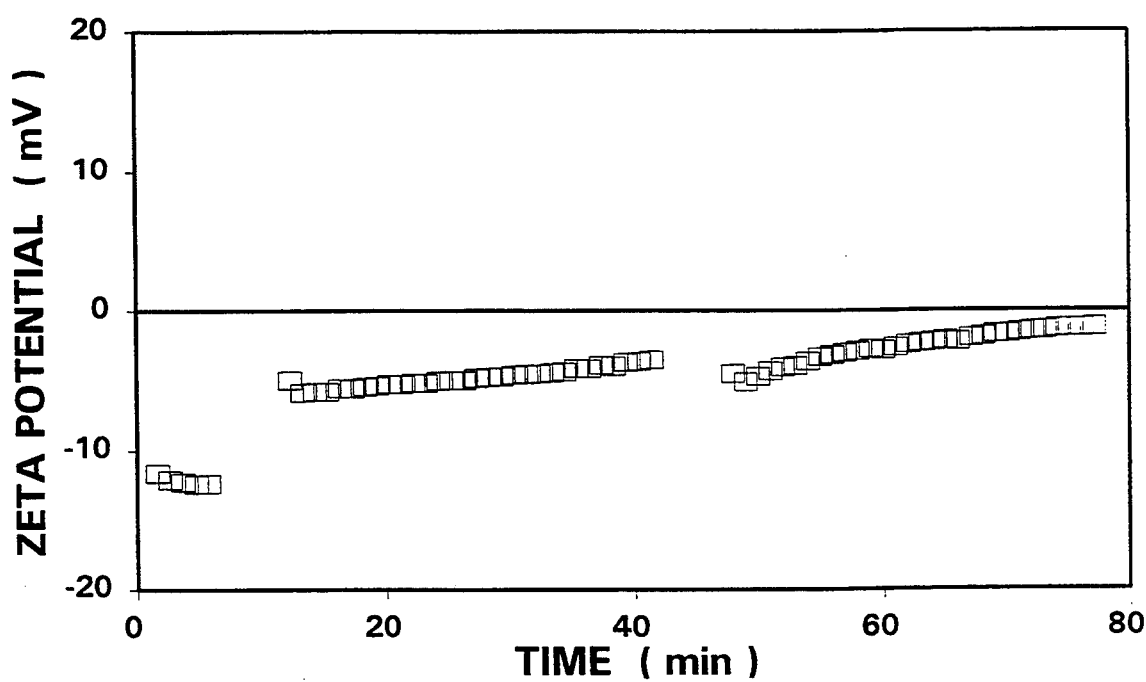
Figure 10B:
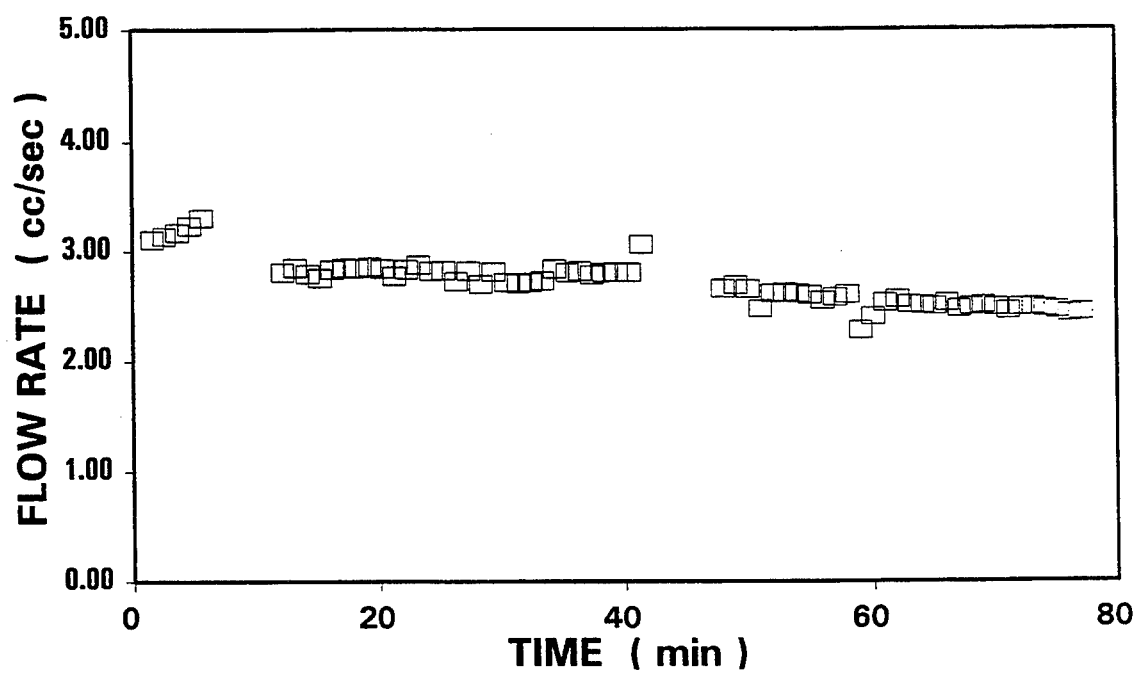
Figure 10C:
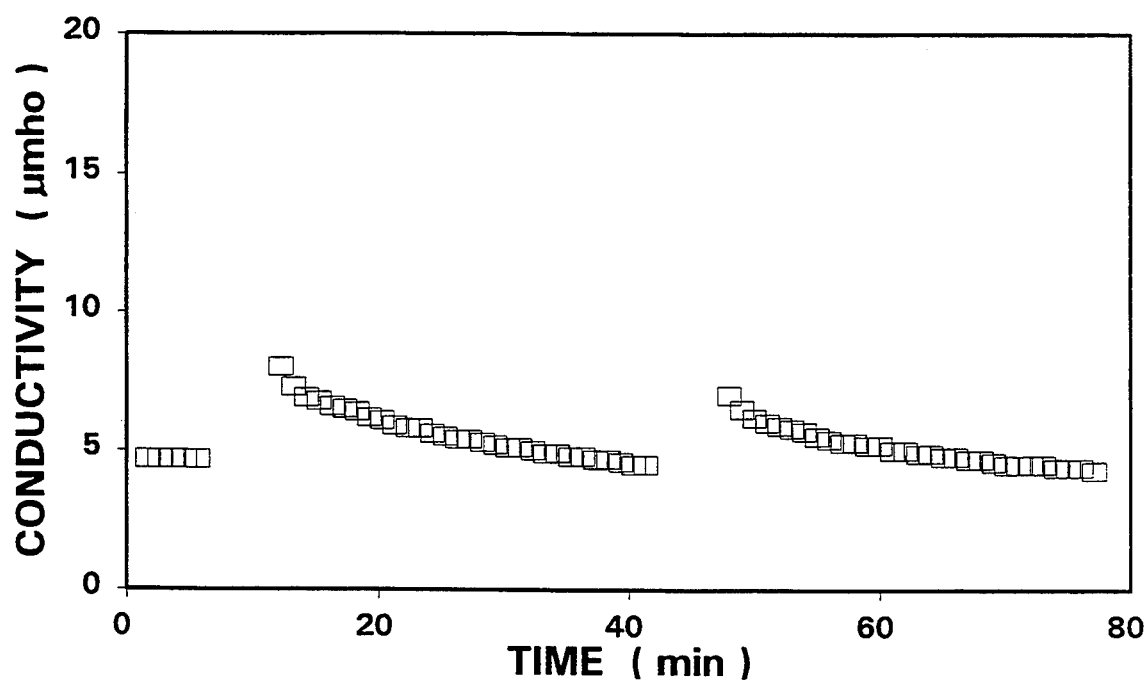
Figure 10D:
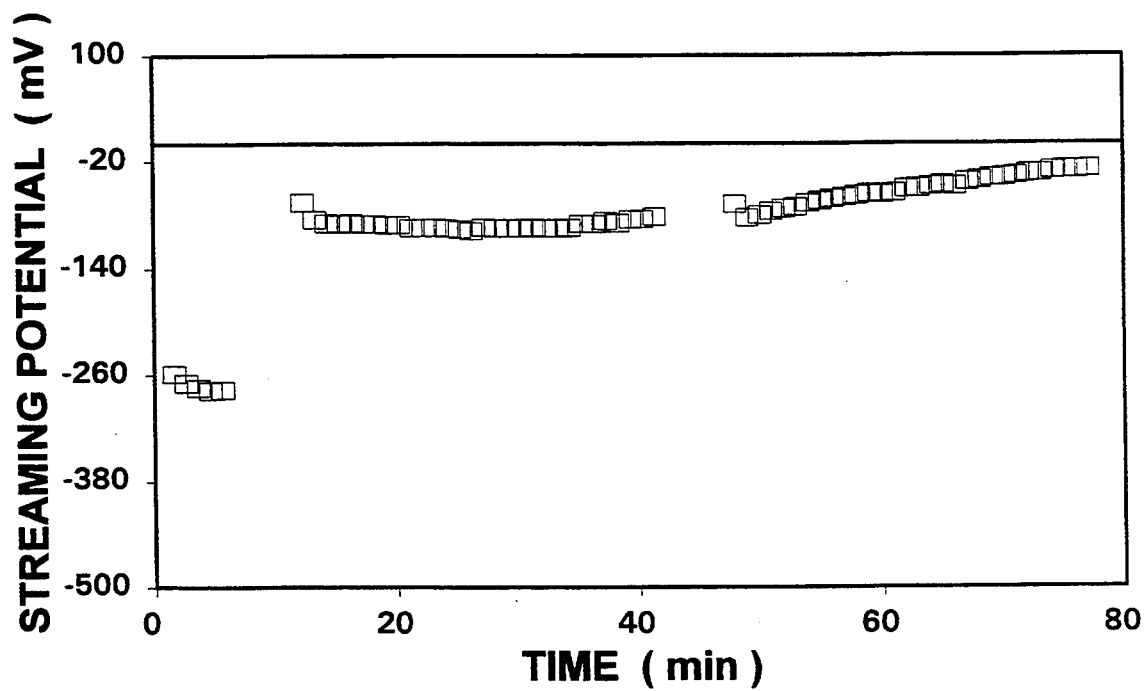
Figure 11A:
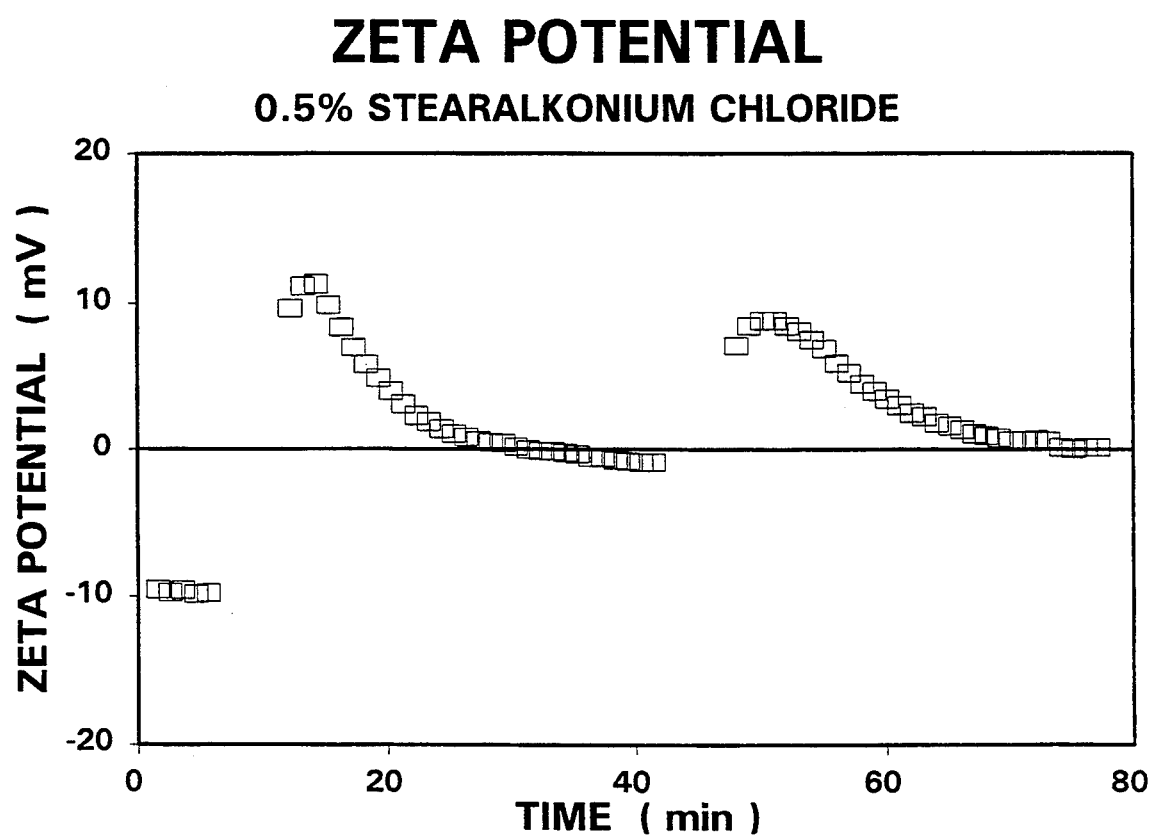
Figure 11B:
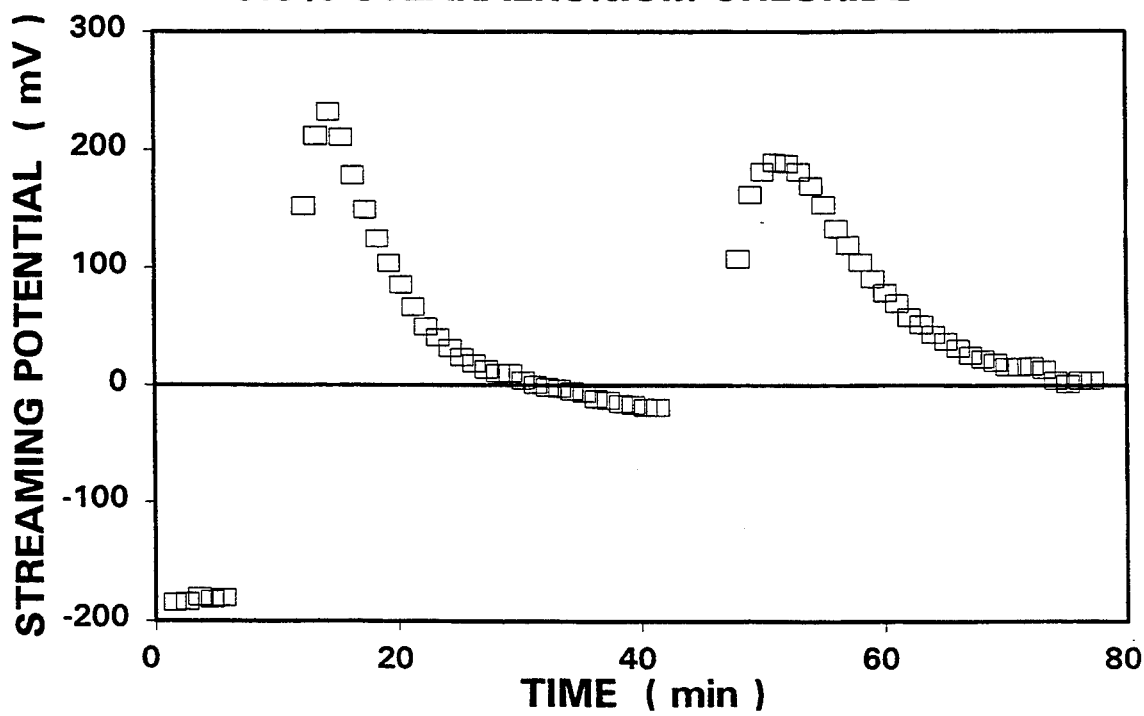
Figure 11C:
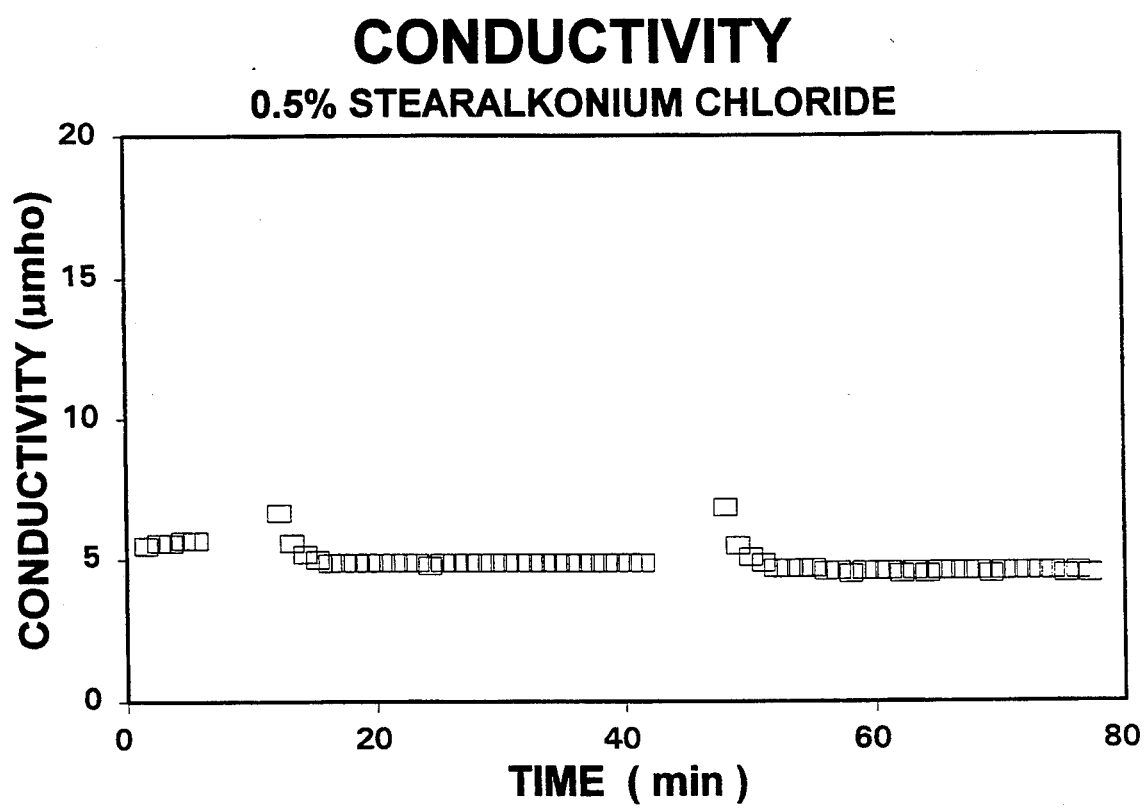
Figure 11D:
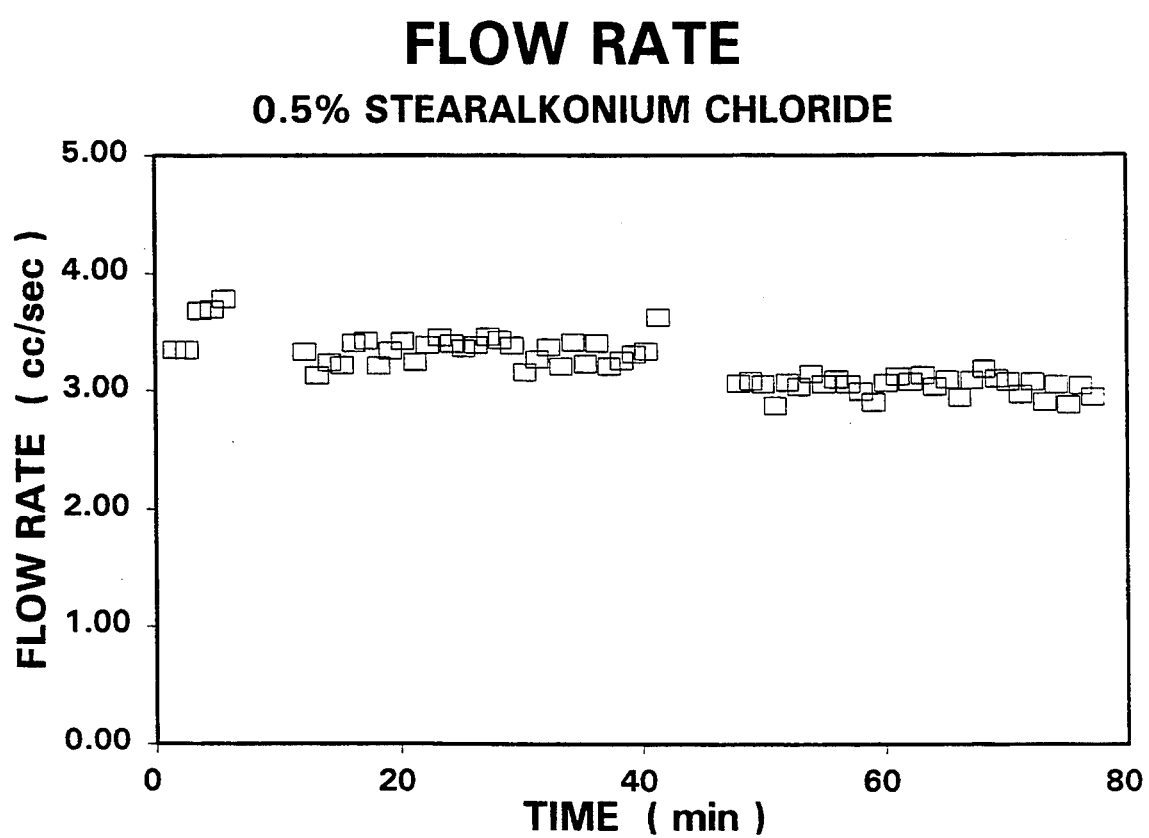
Figure 12A:
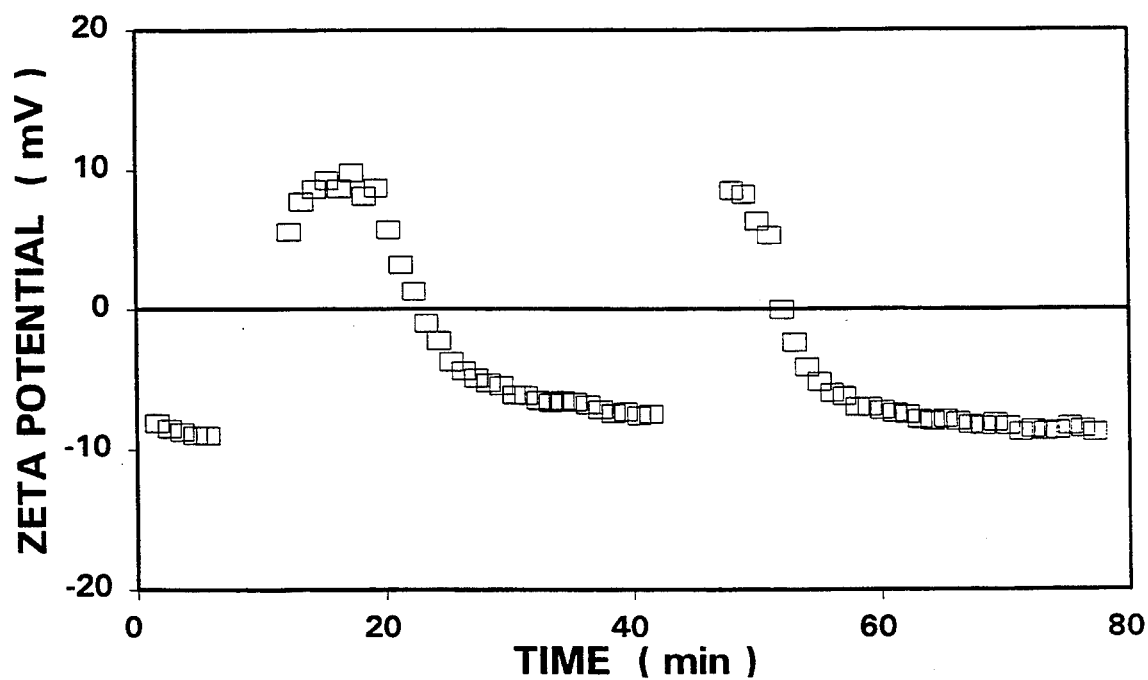
Figure 12B:
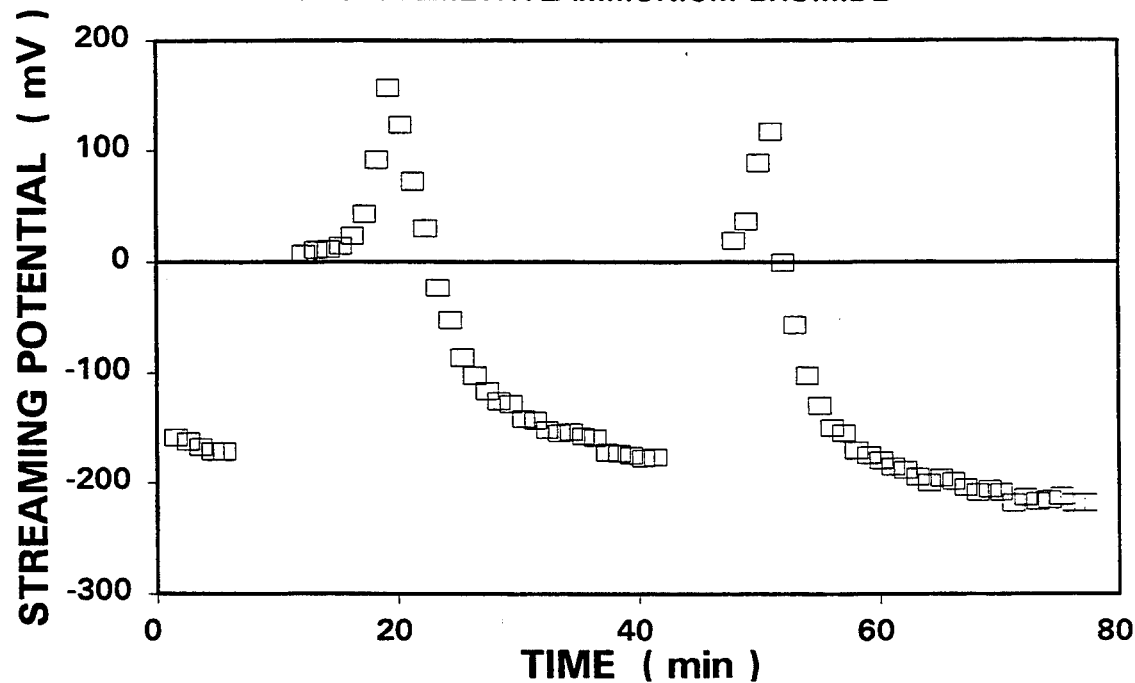
Figure 12C:
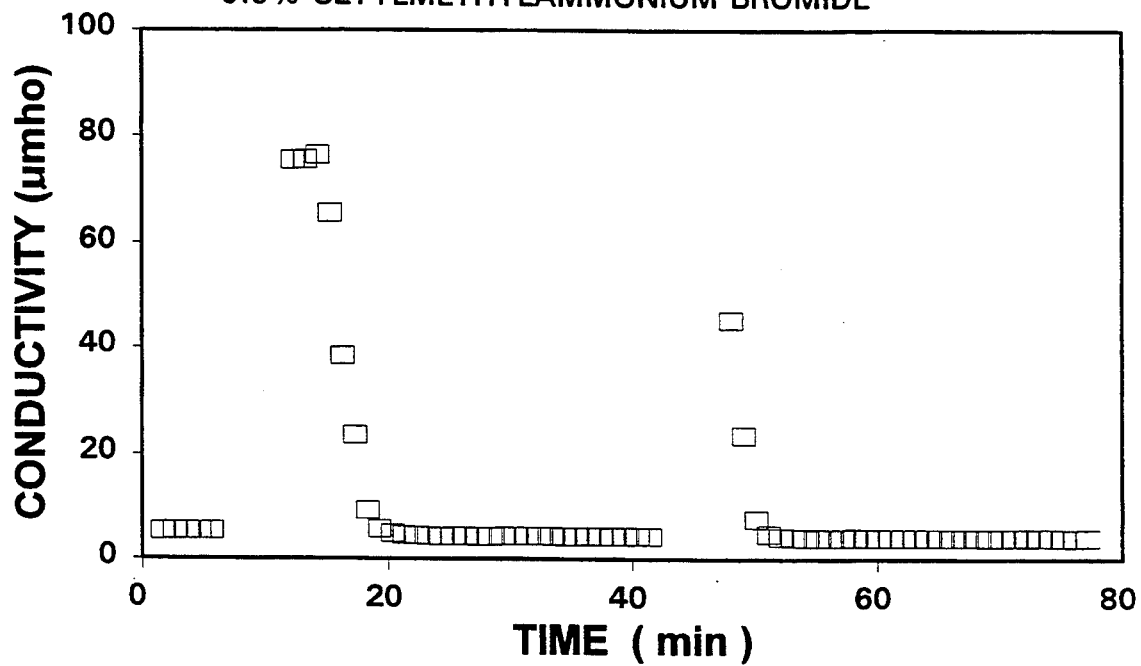
Figure 12D:
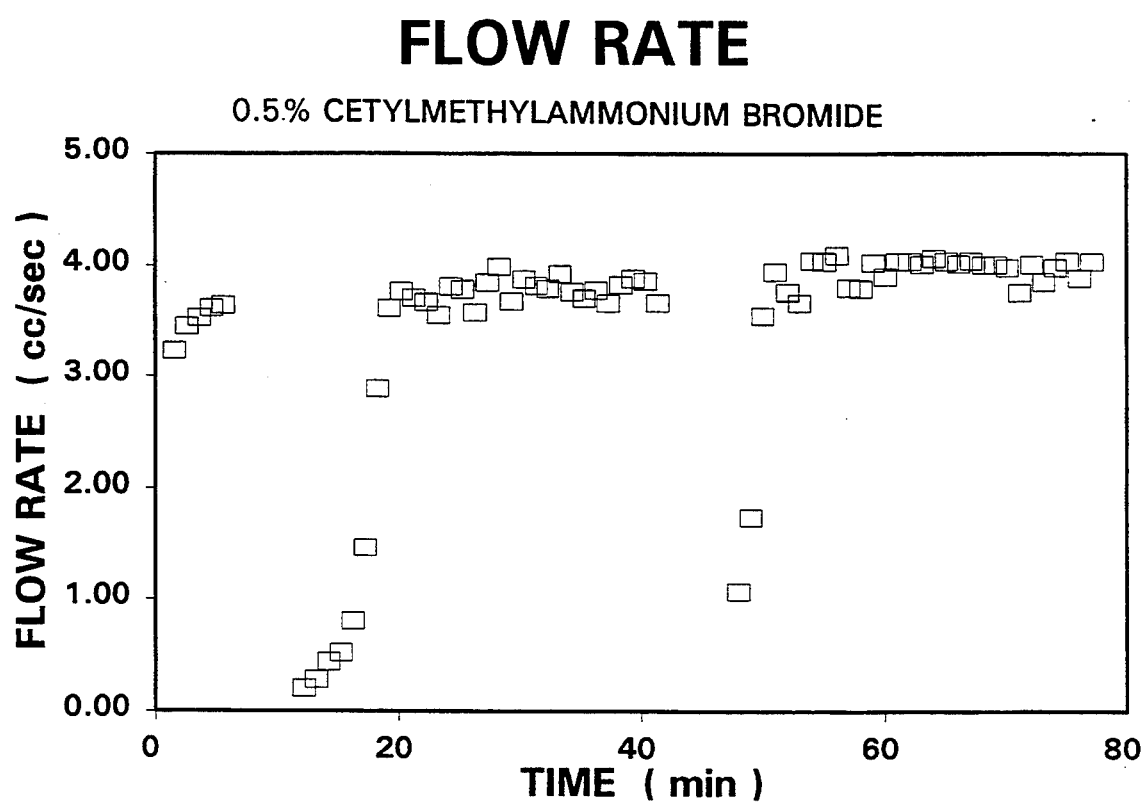
Figure 13A:
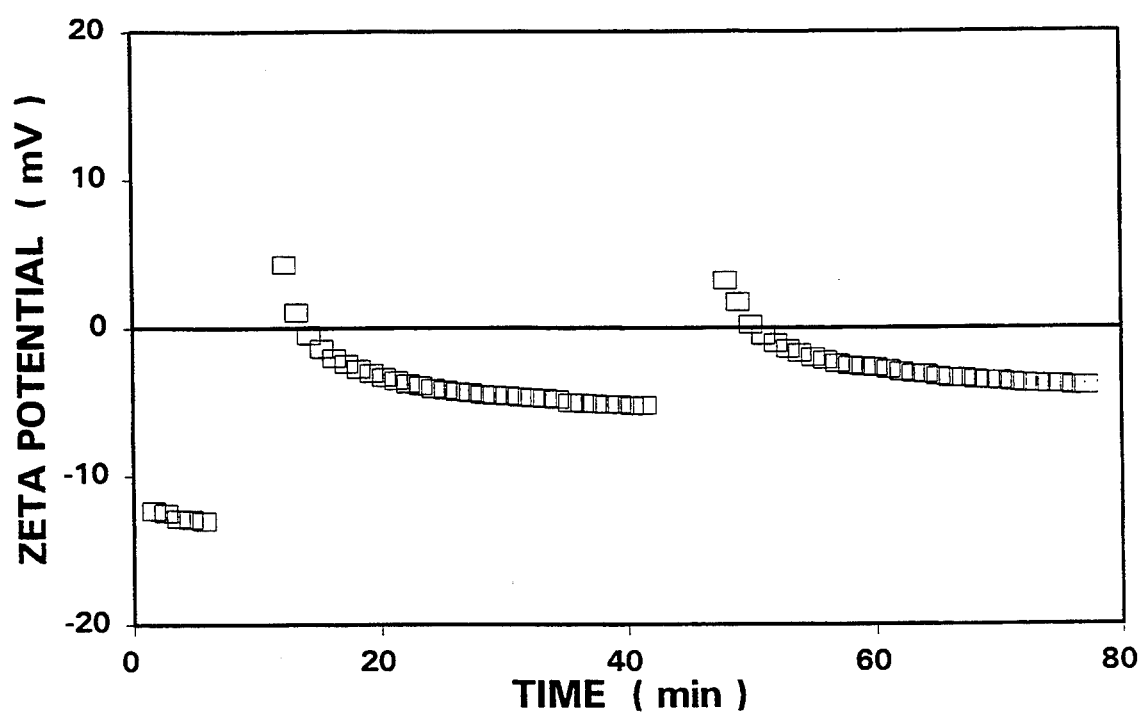
Figure 13B:
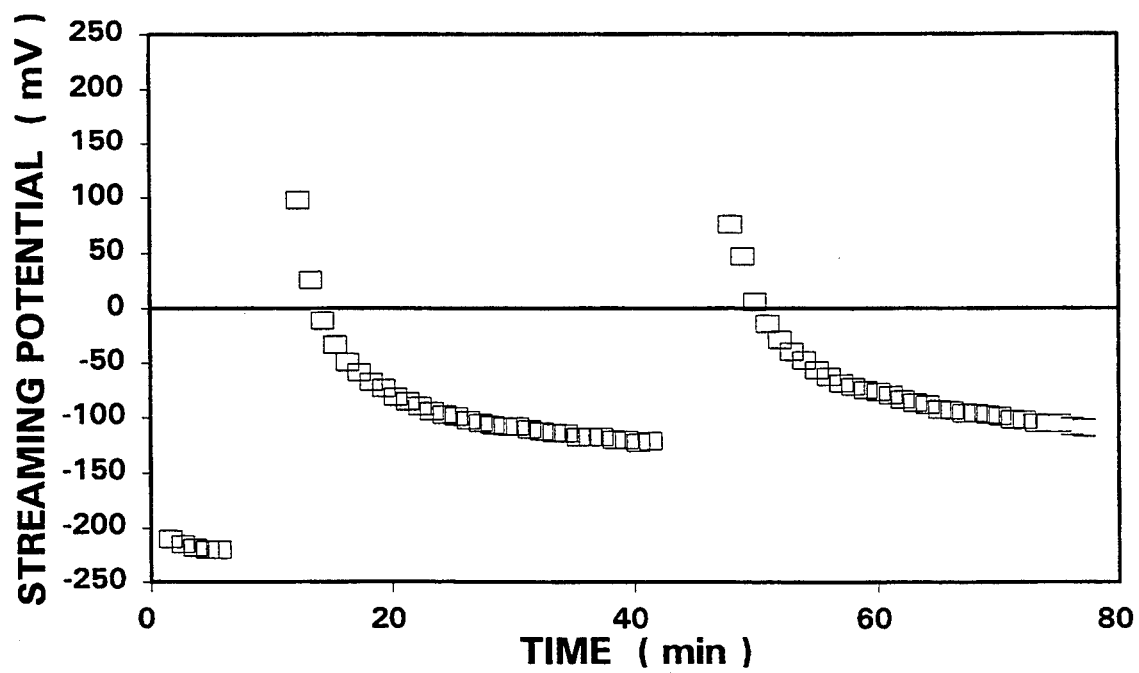
Figure 13C:
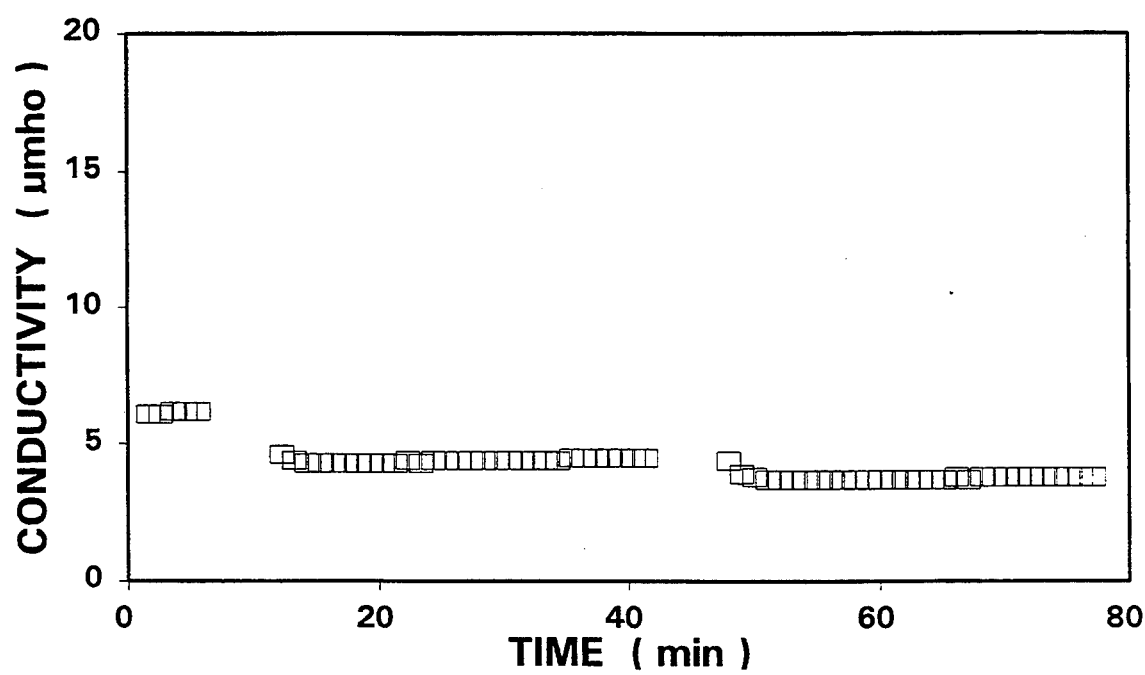
Figure 13D:
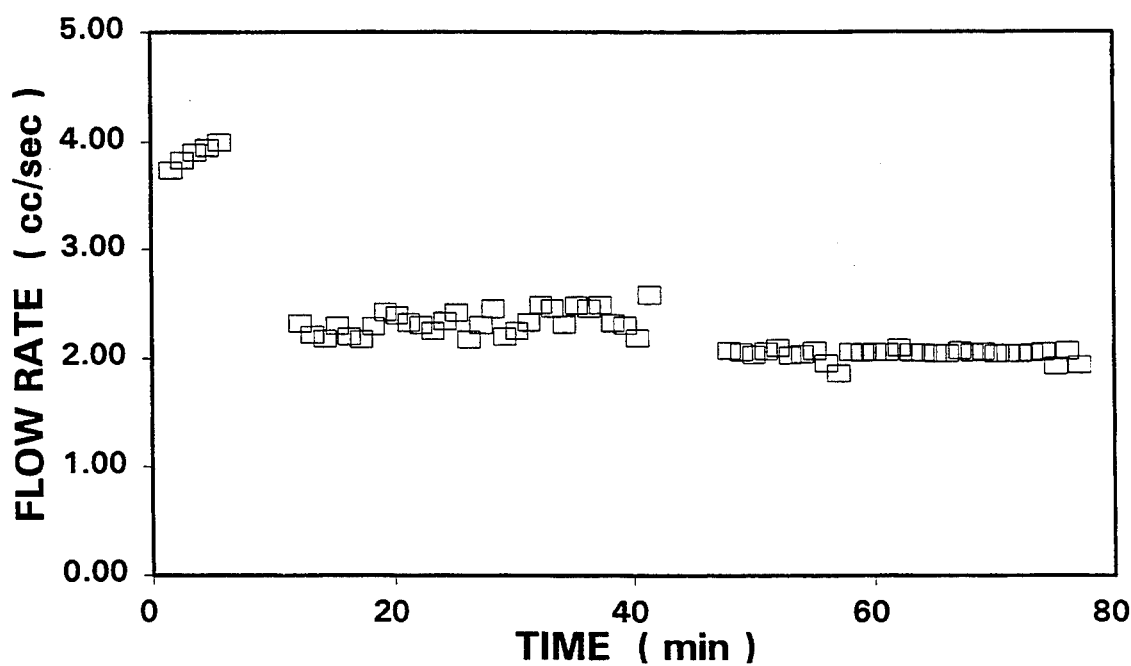
Figure 14A:
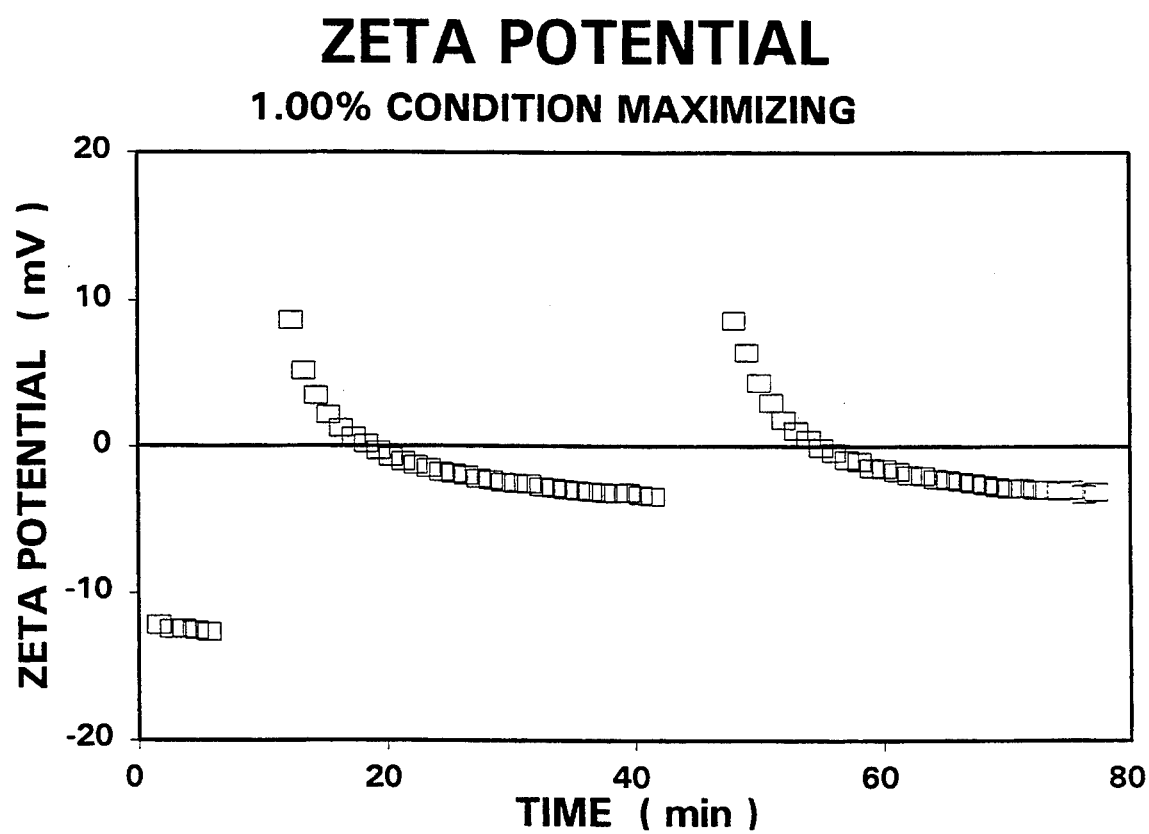
Figure 14B:
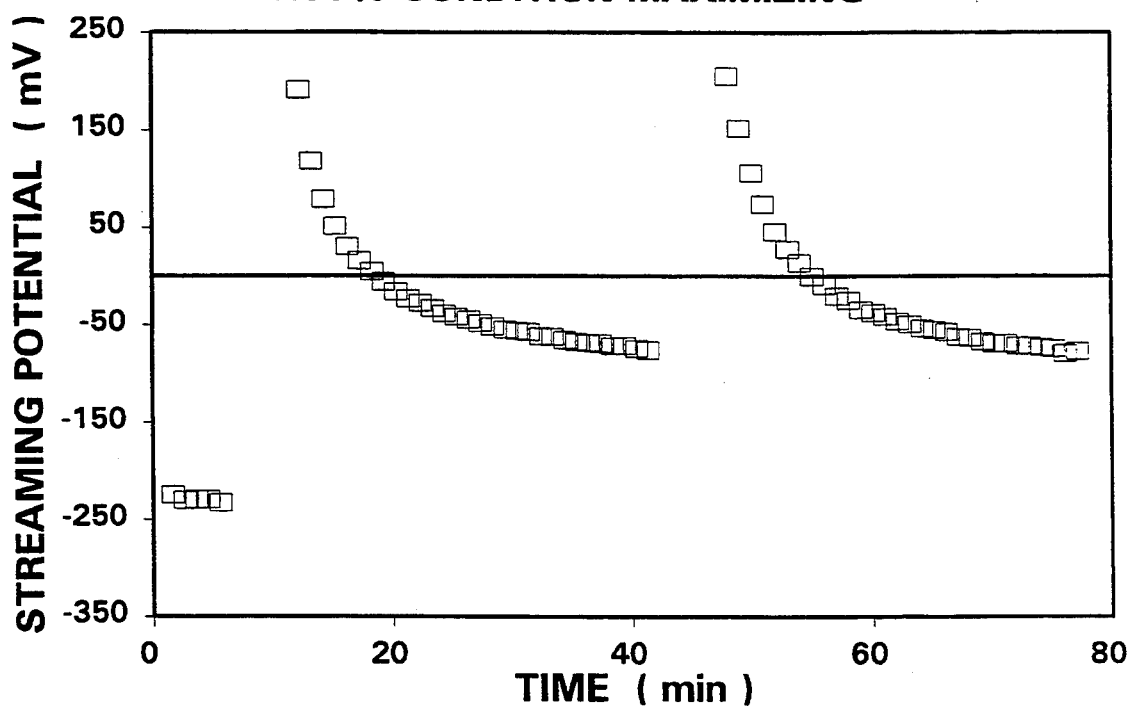
Figure 14C:
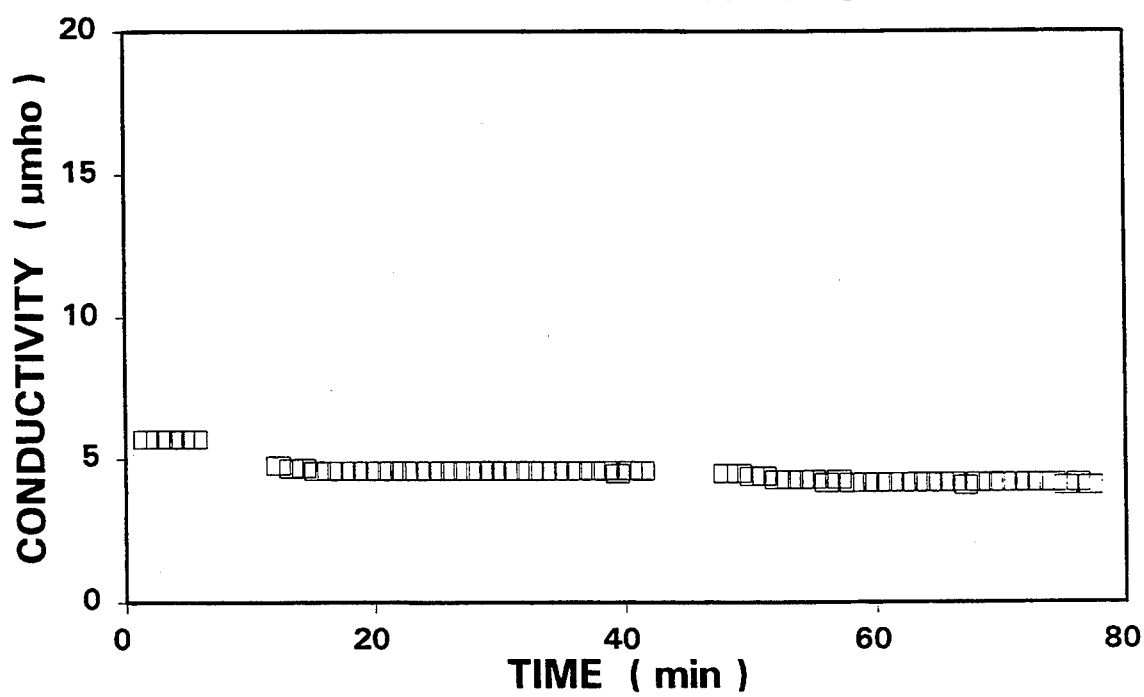
Figure 14D:
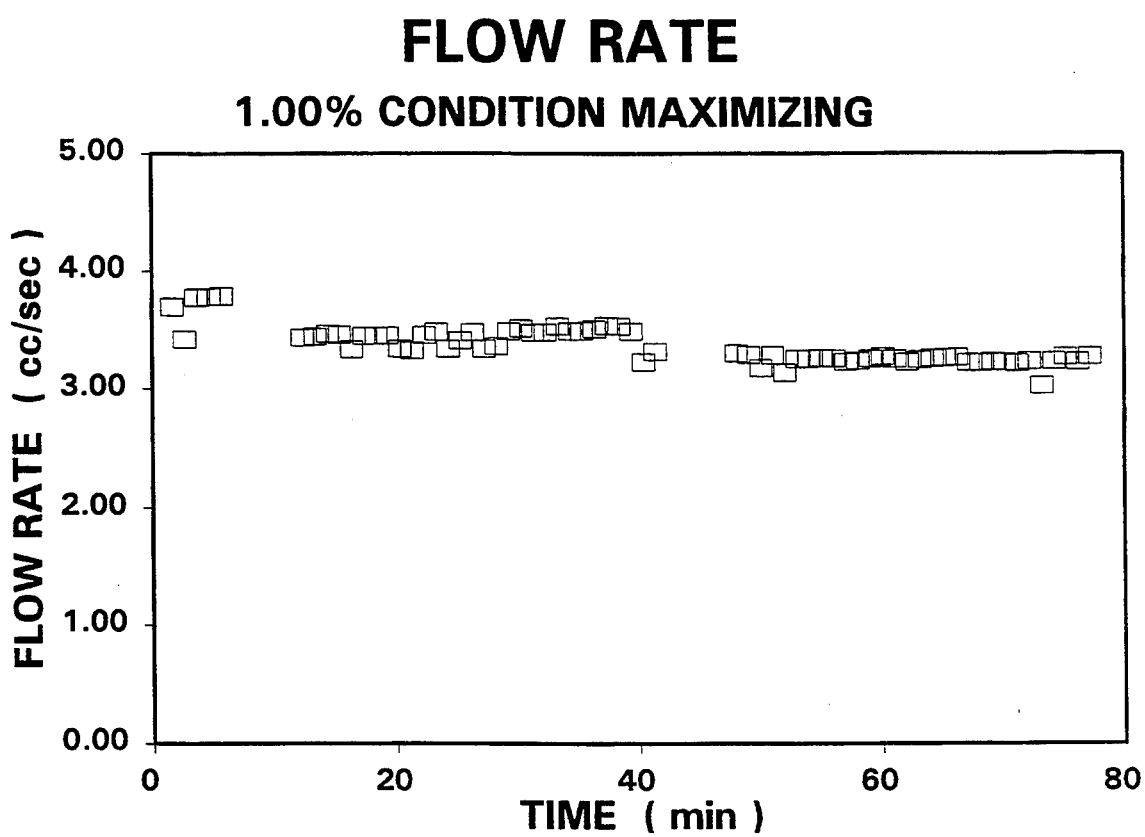
Figure 15A:
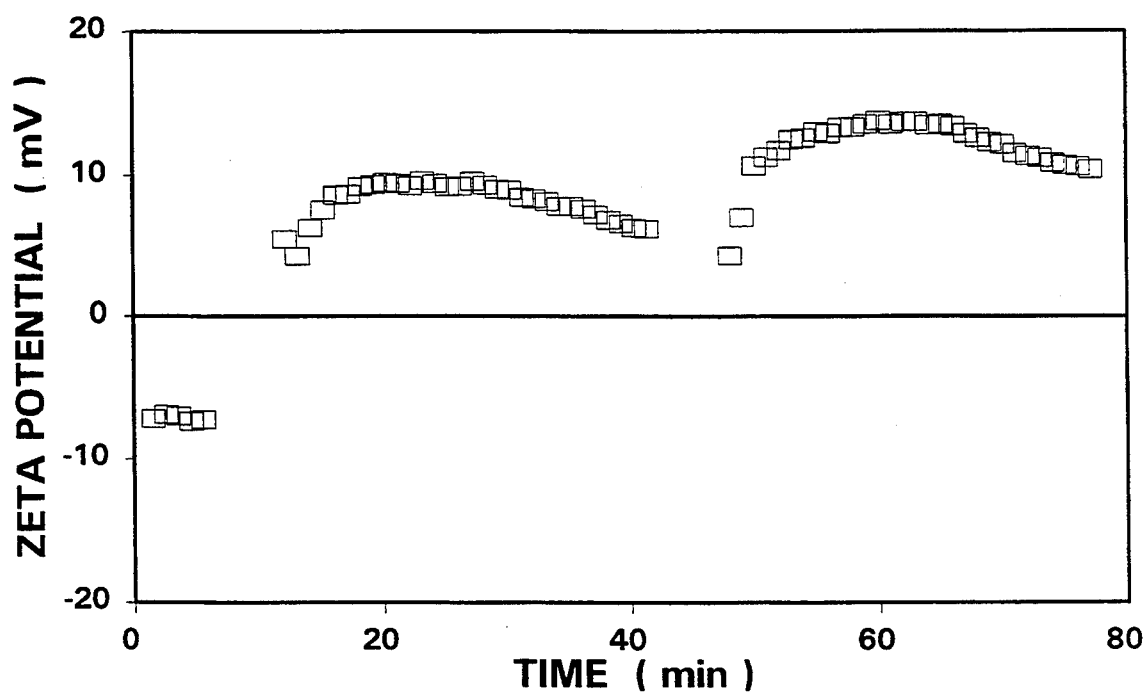
Figure 15B:
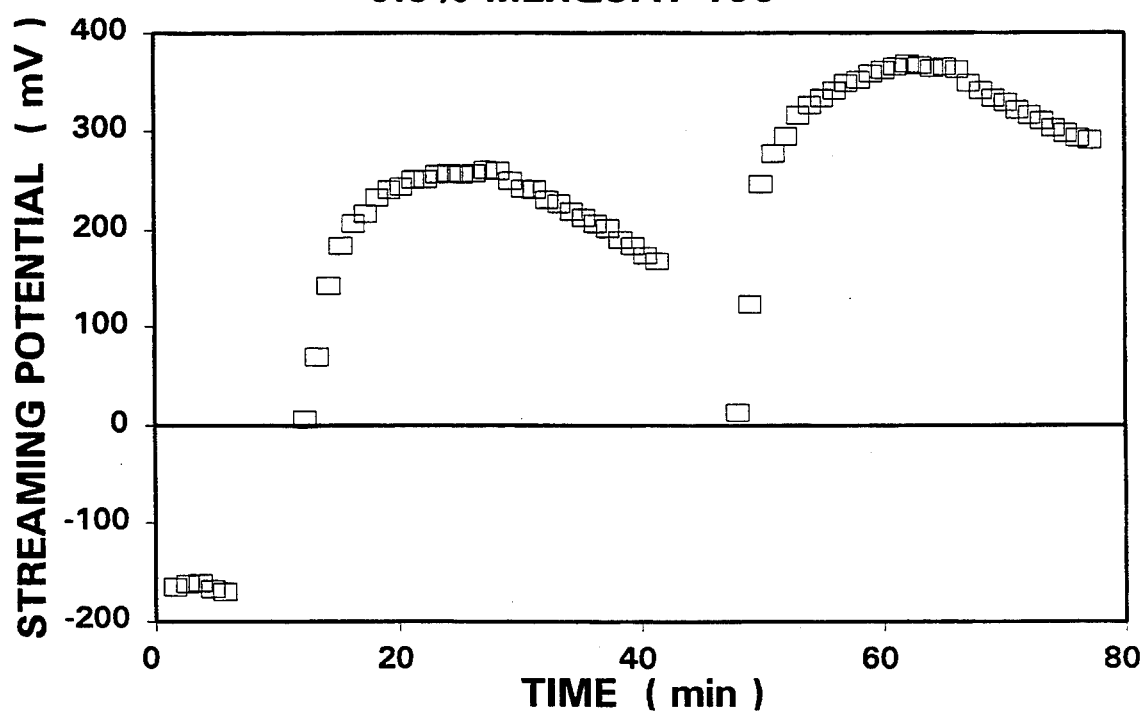
Figure 15C:
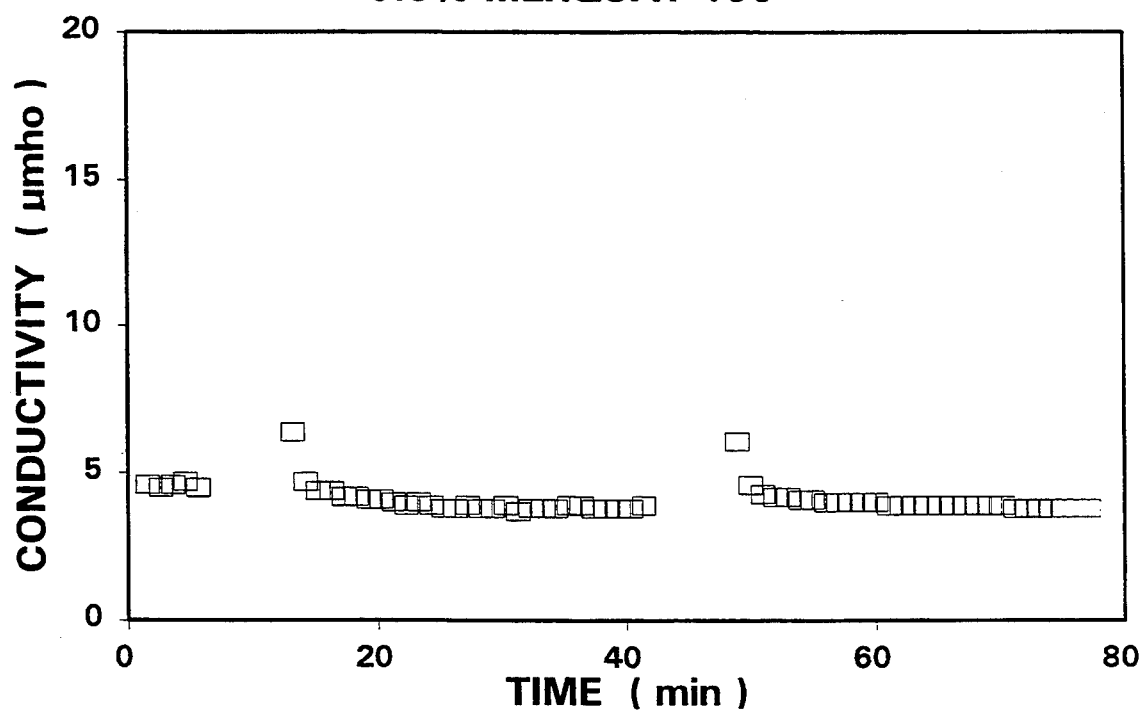
Figure 15D:
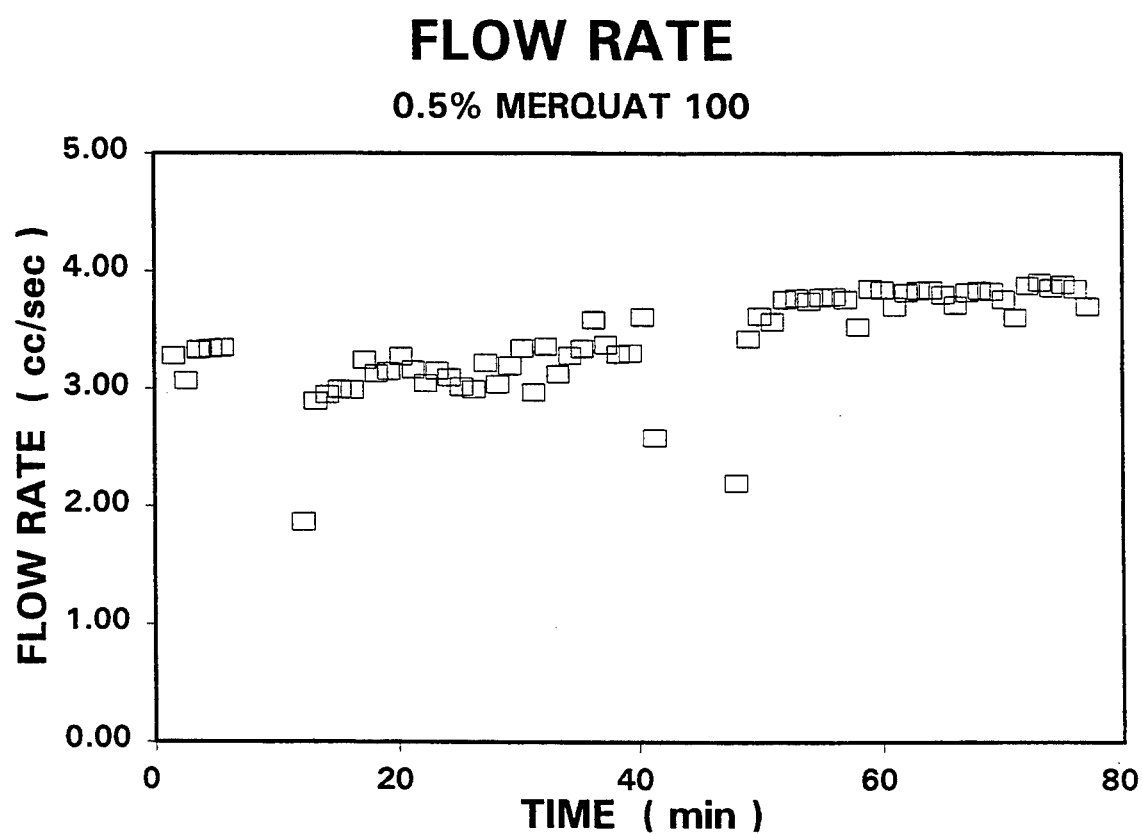
Figure 16A:
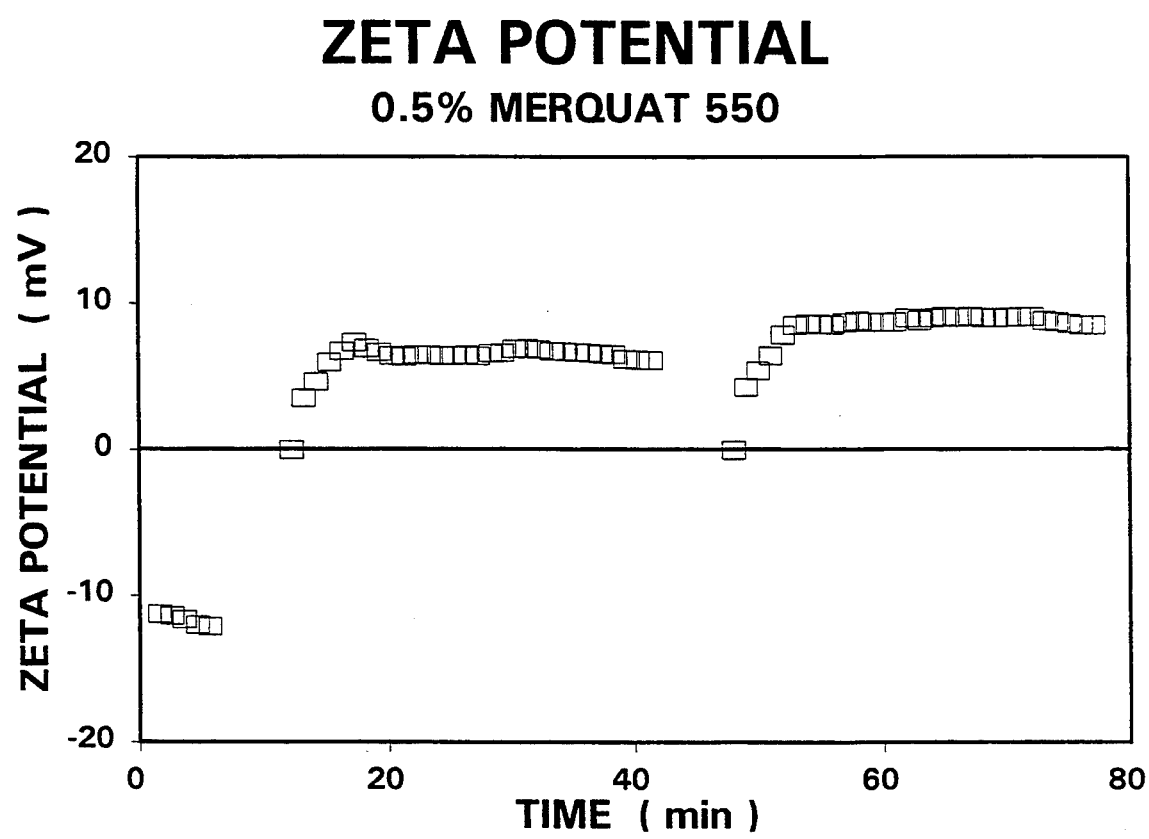
Figure 16B:
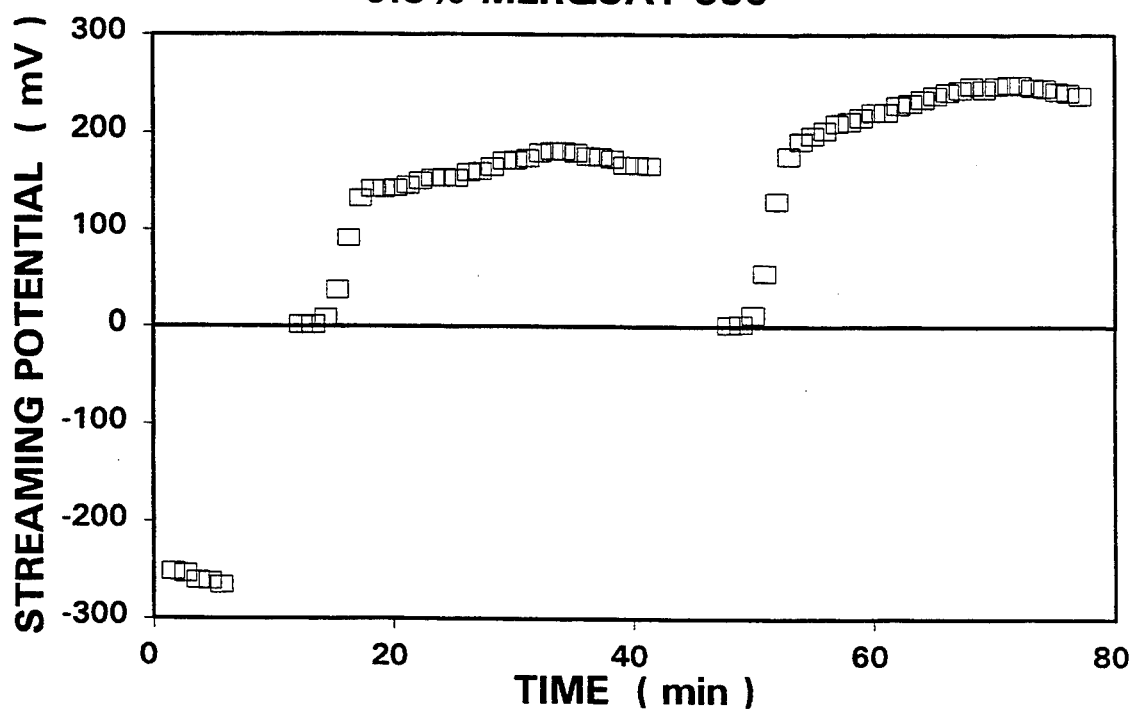
Figure 16C:
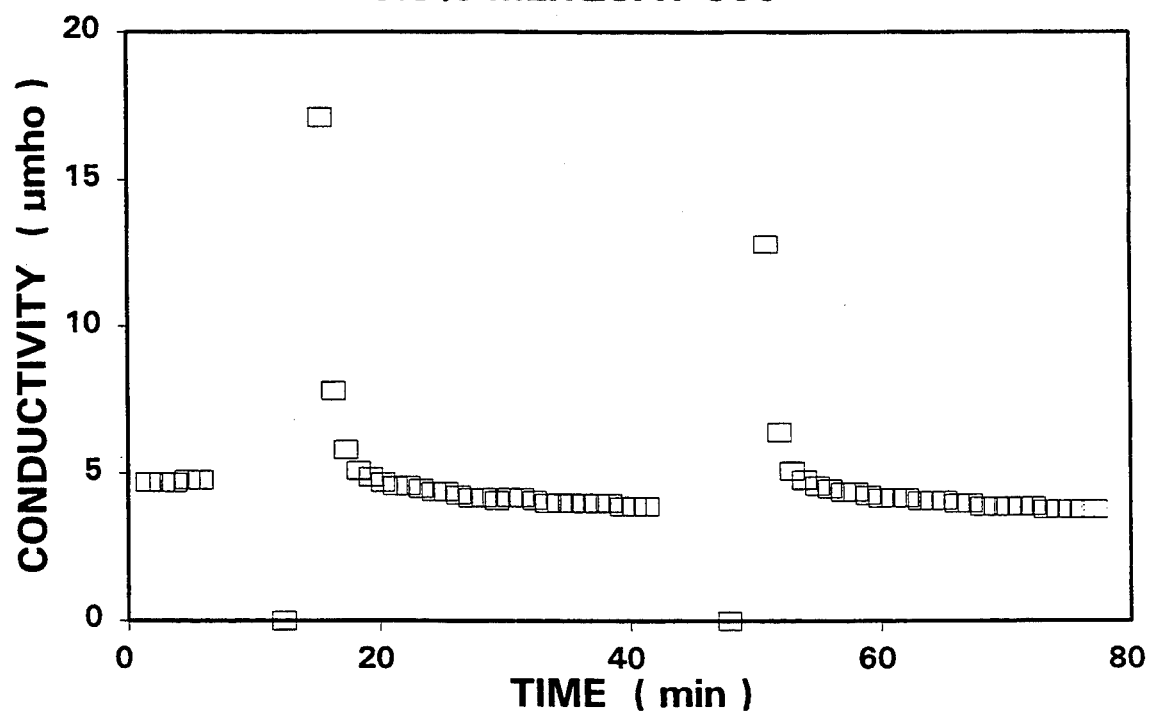
Figure 16D:
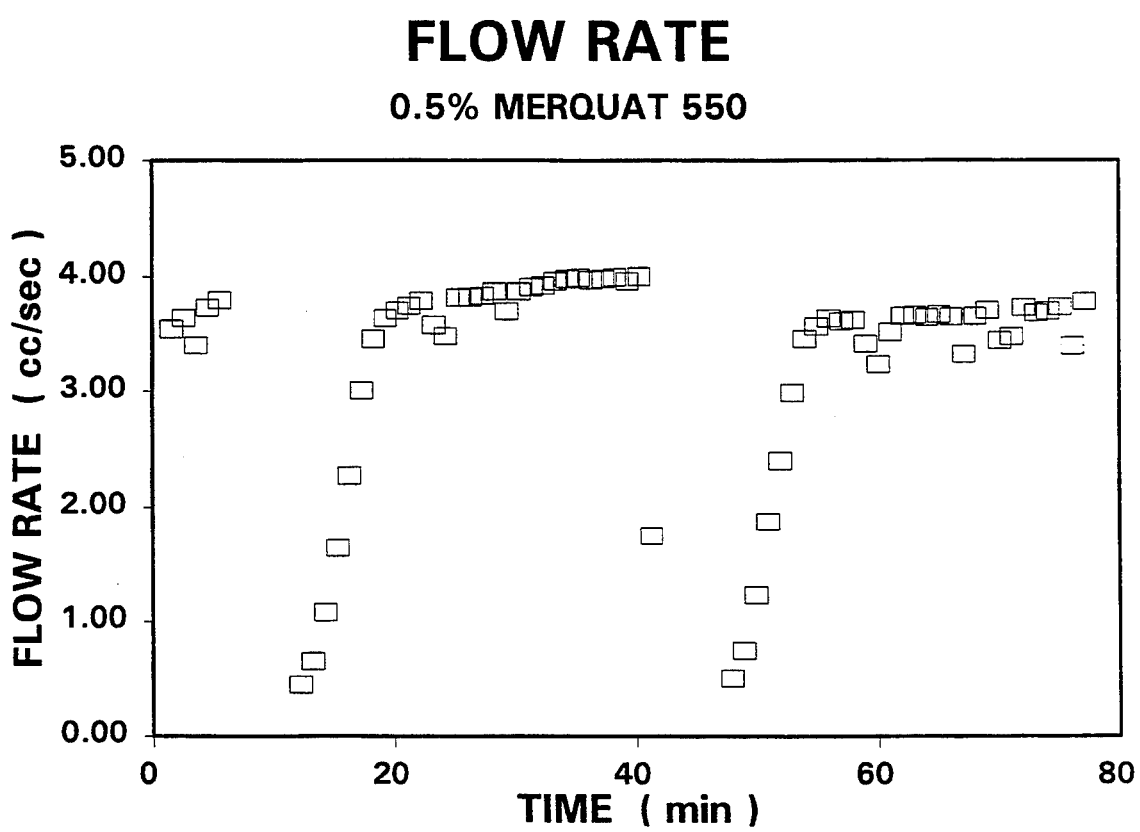
Figure 17A:
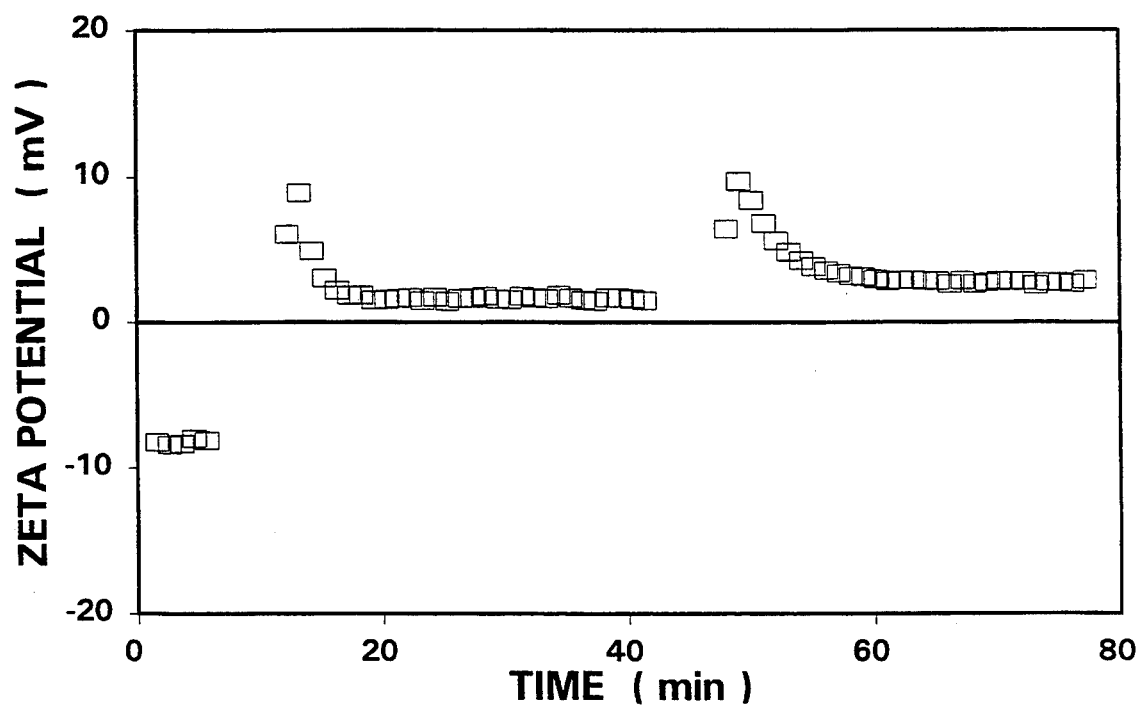
Figure 17B:
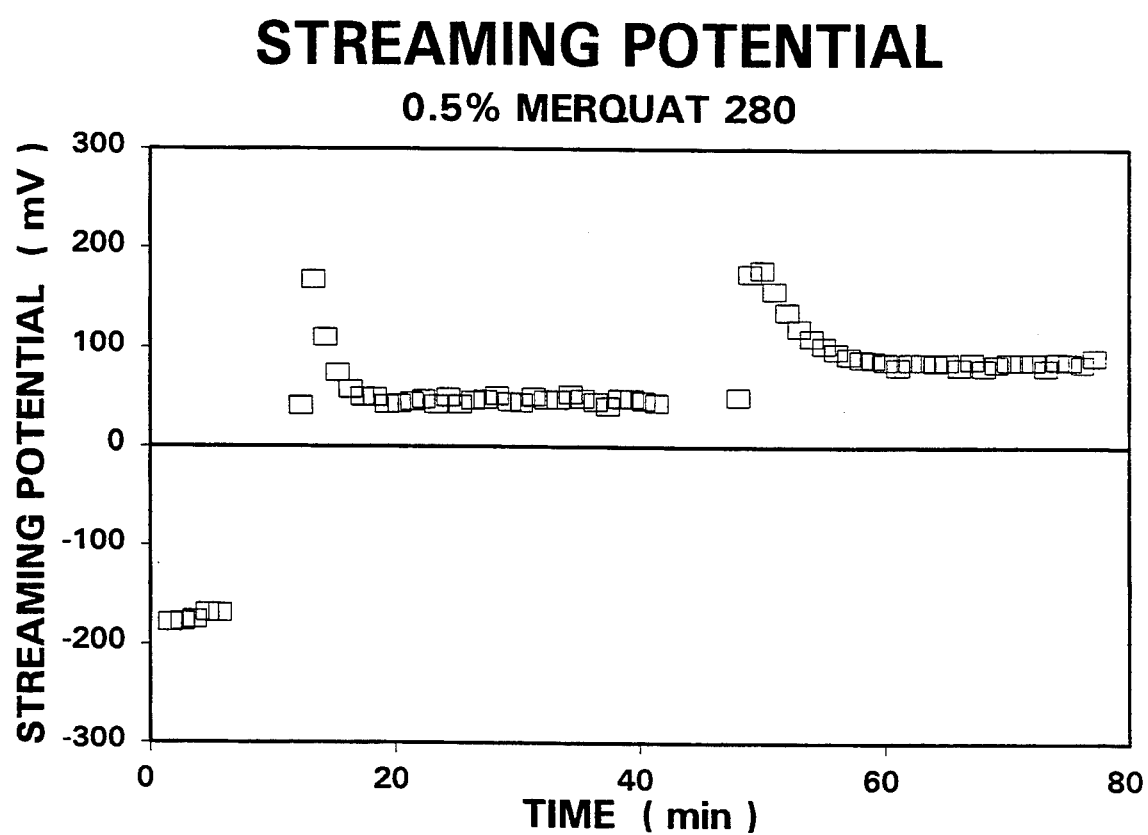
Figure 17C:
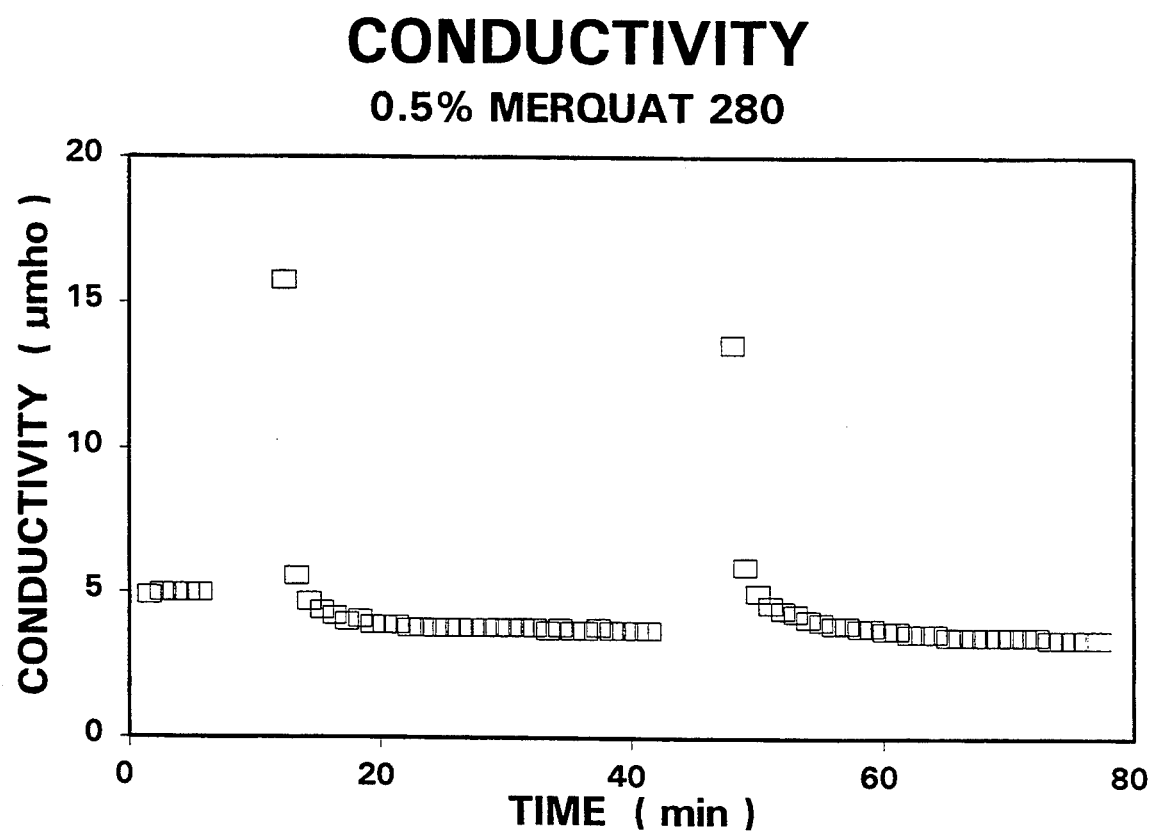
Figure 17D:
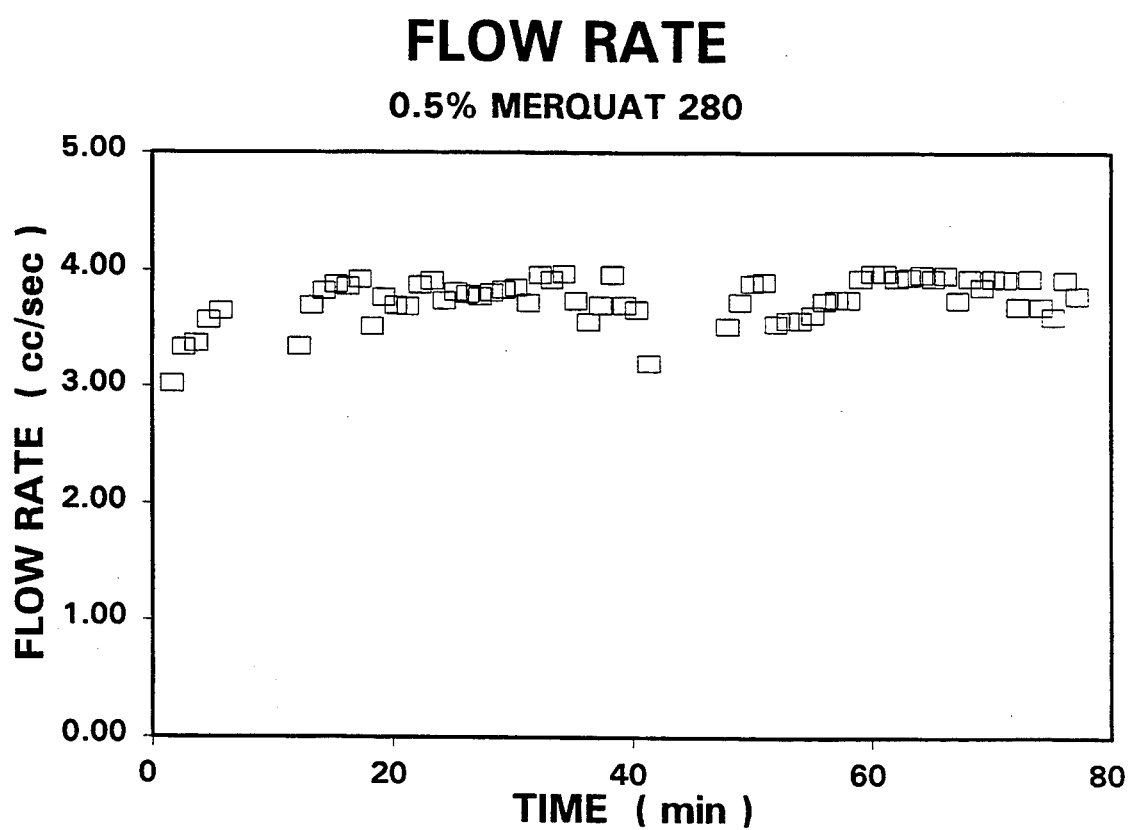
Figure 18A:
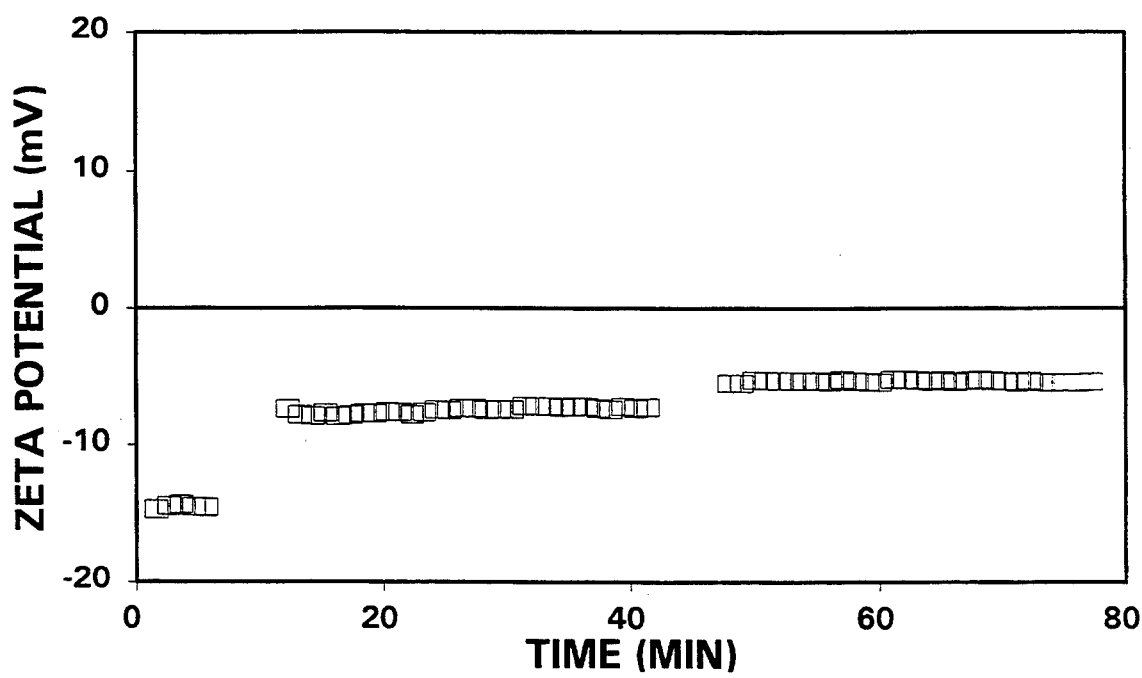
Figure 18B:
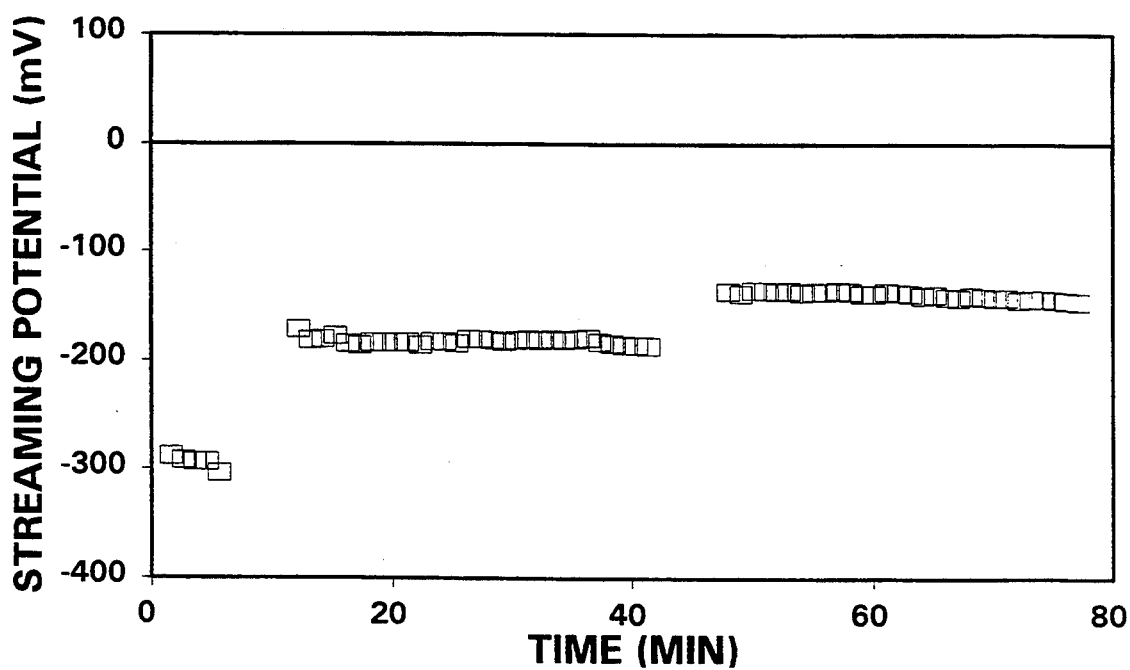
Figure 18C:
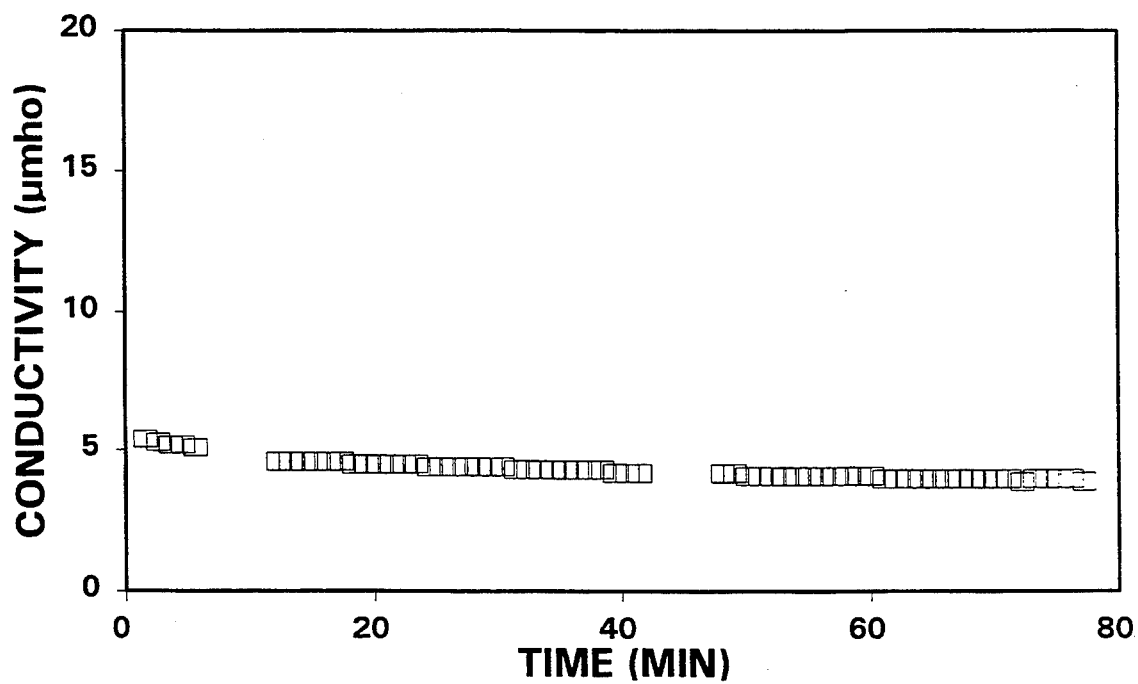
Figure 18D:
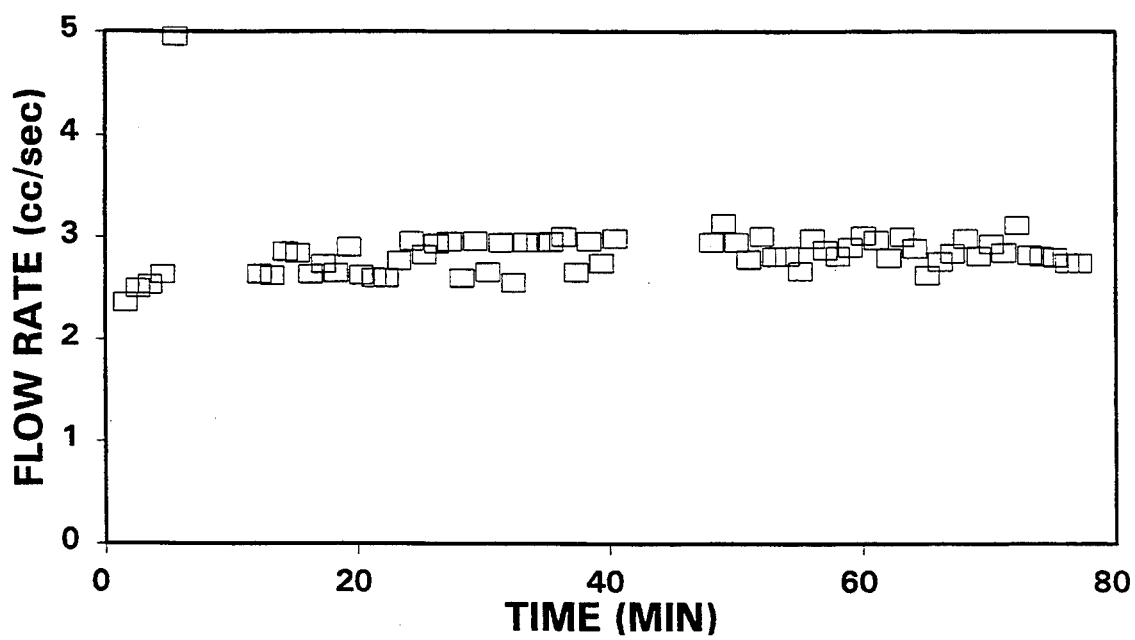
Figure 19A:
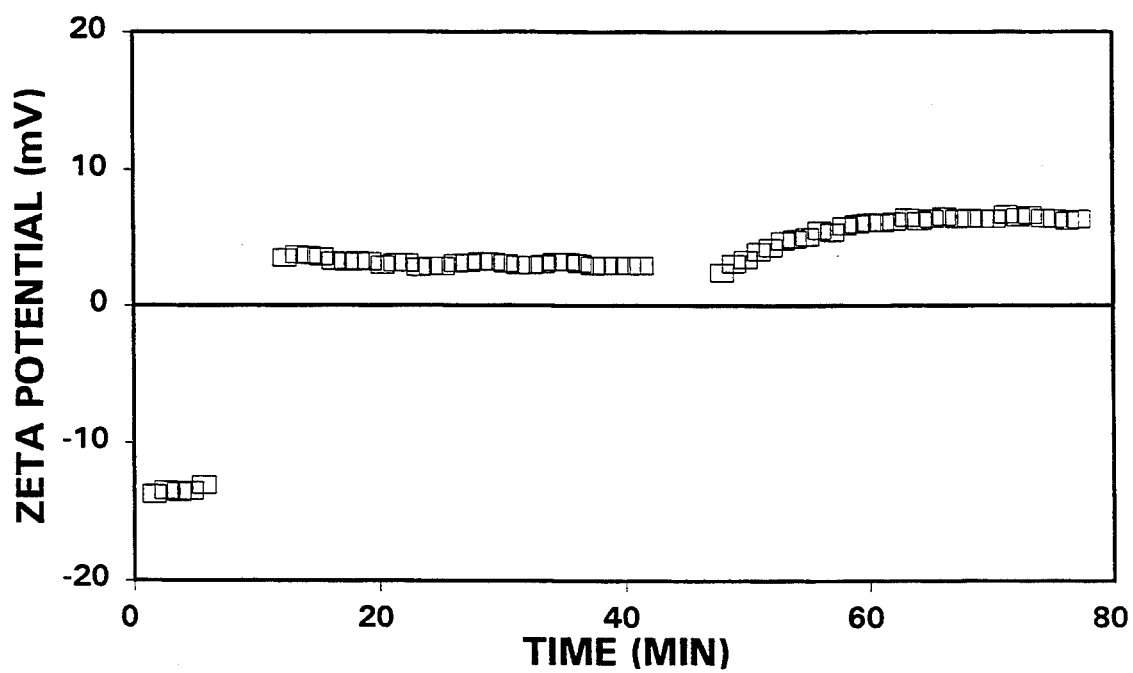
Figure 19B:
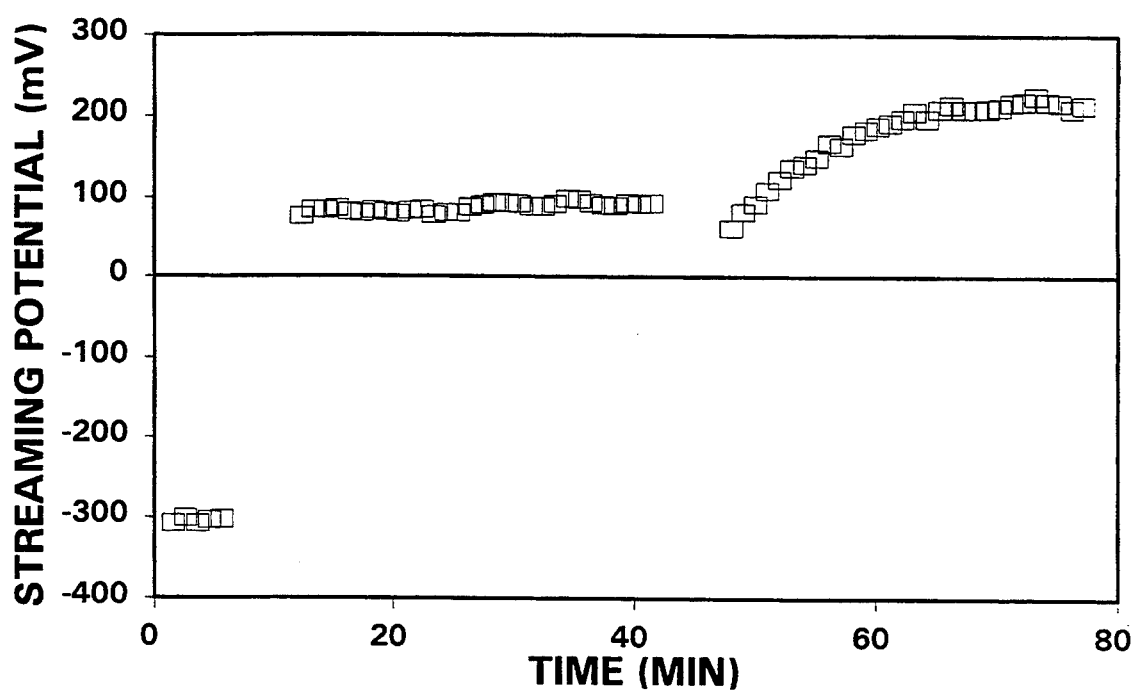
Figure 19C:
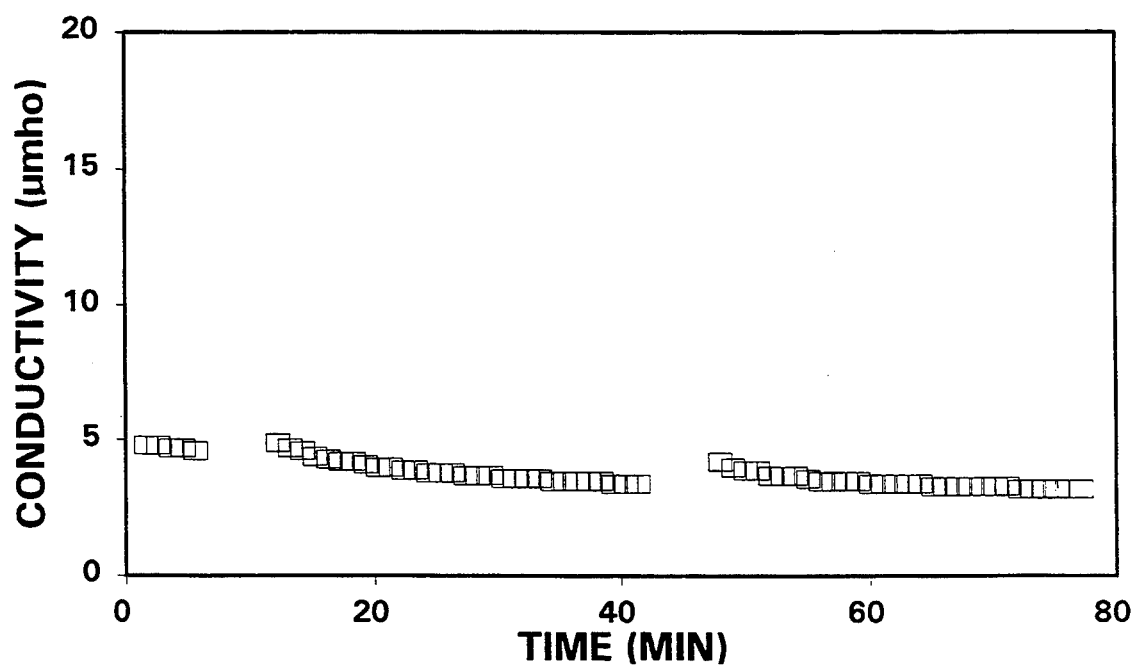
Figure 19D:
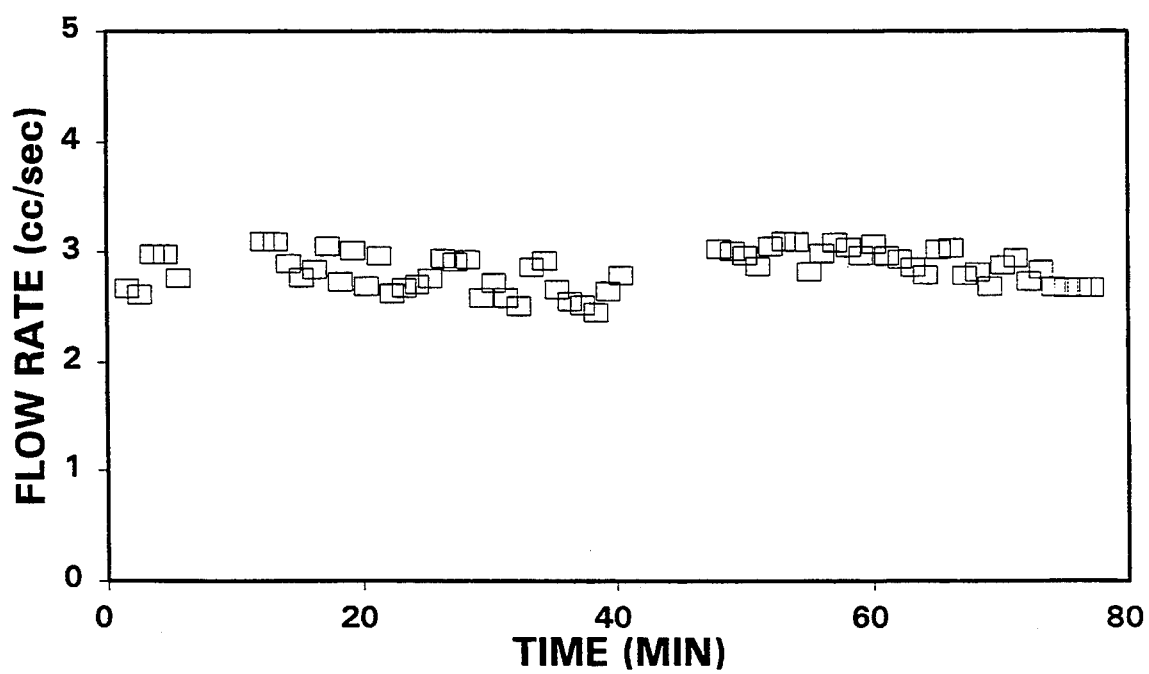
Figure 20A:
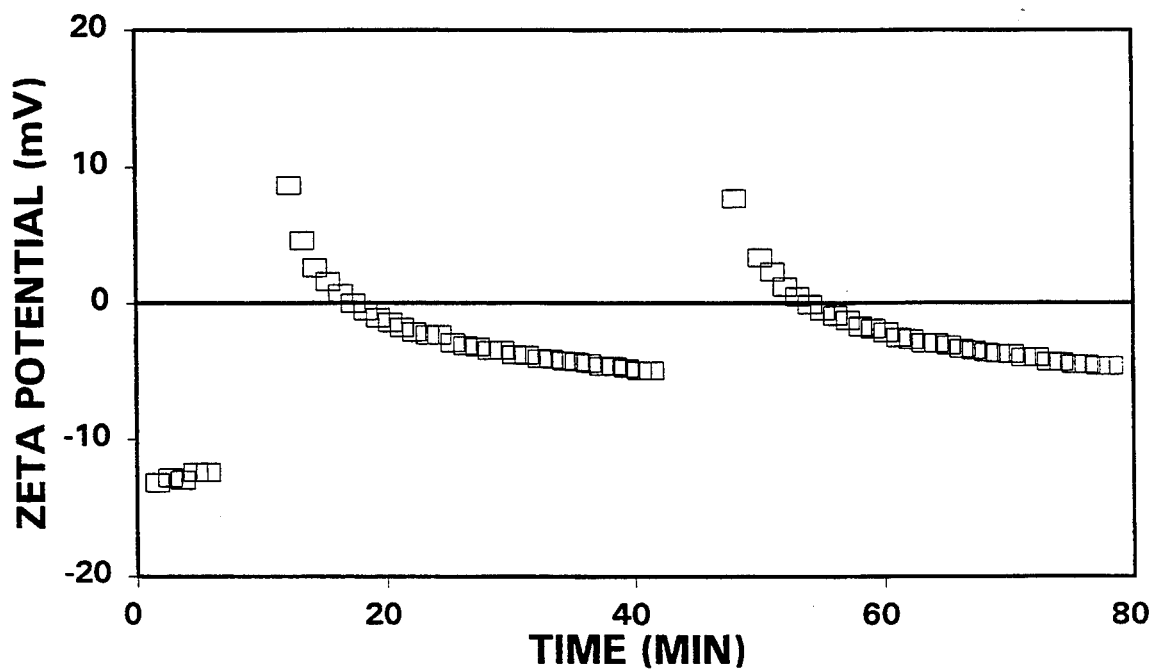
Figure 20B:
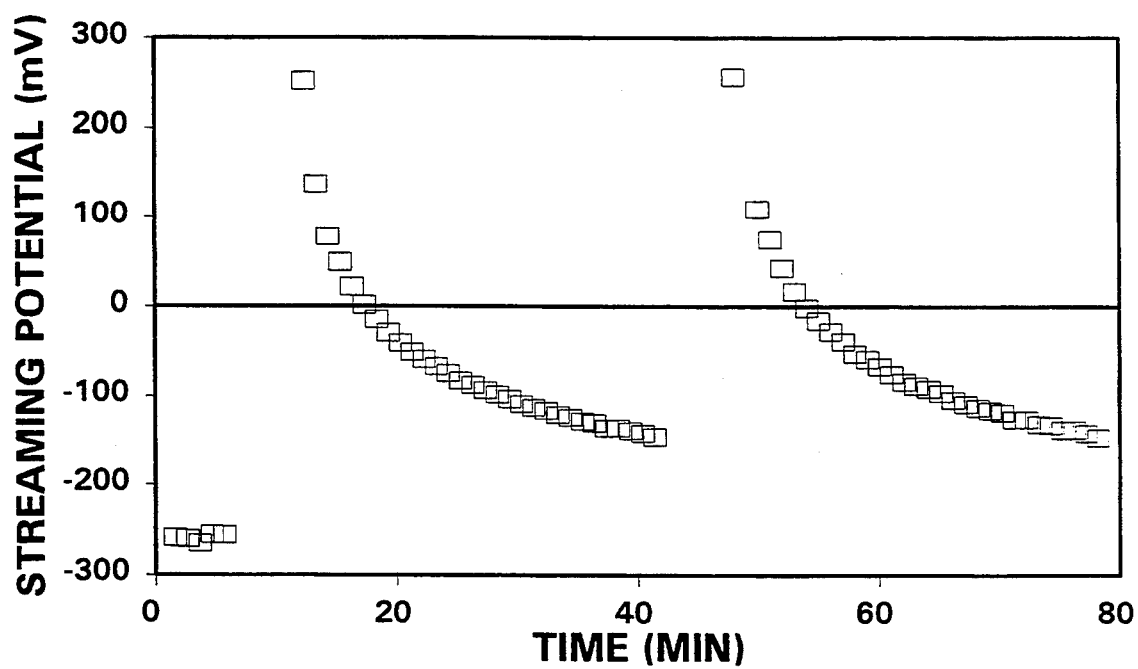
Figure 20C:
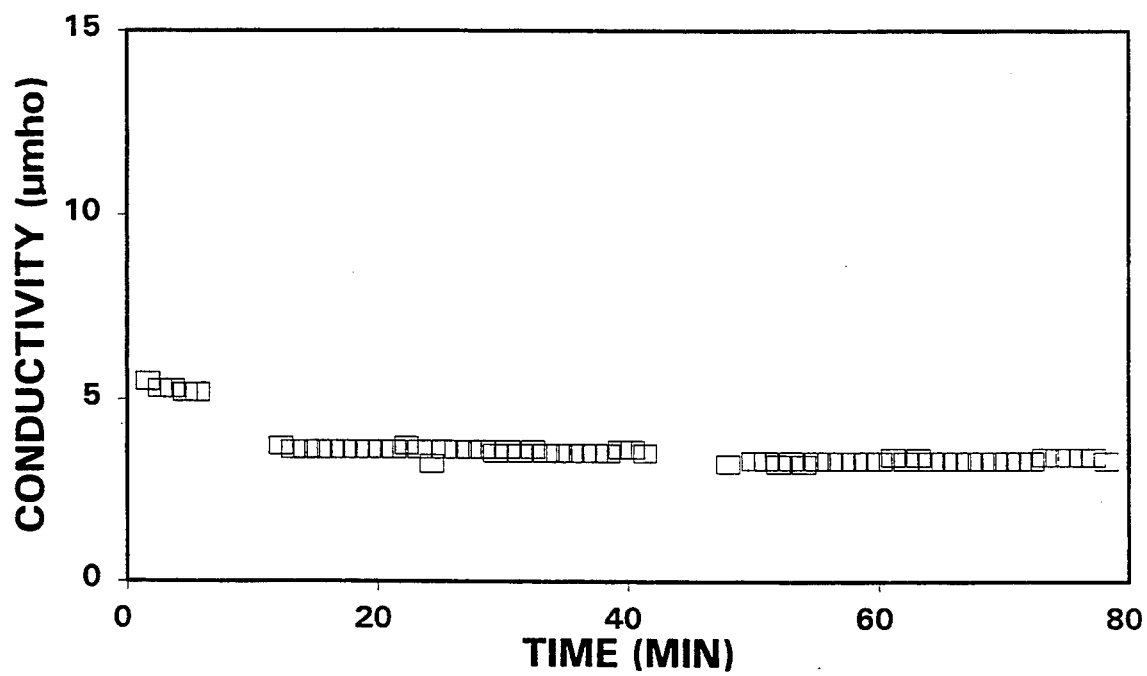
Figure 20D:
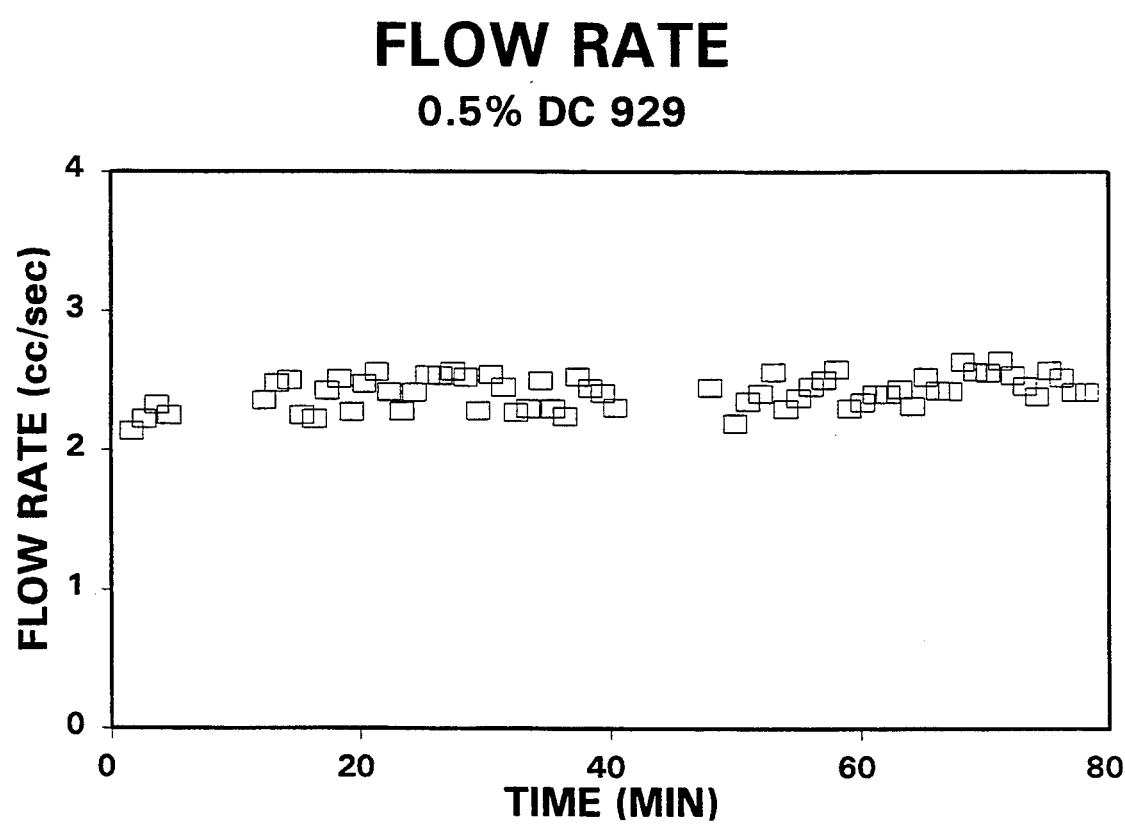
Figure 21A:
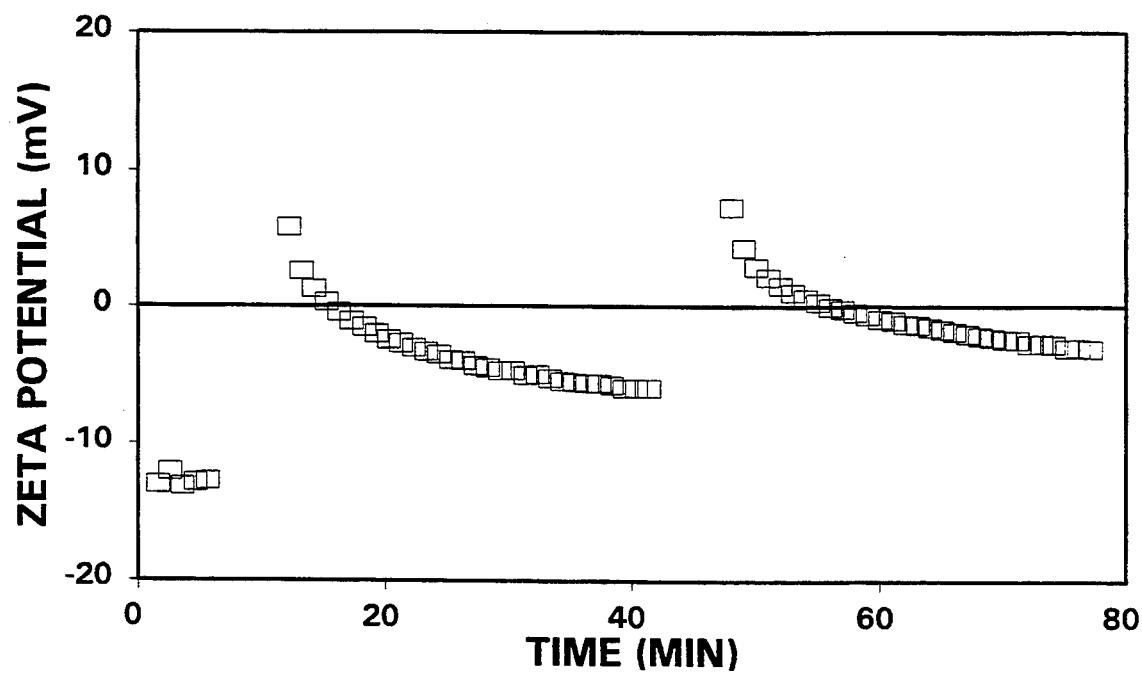
Figure 21B:
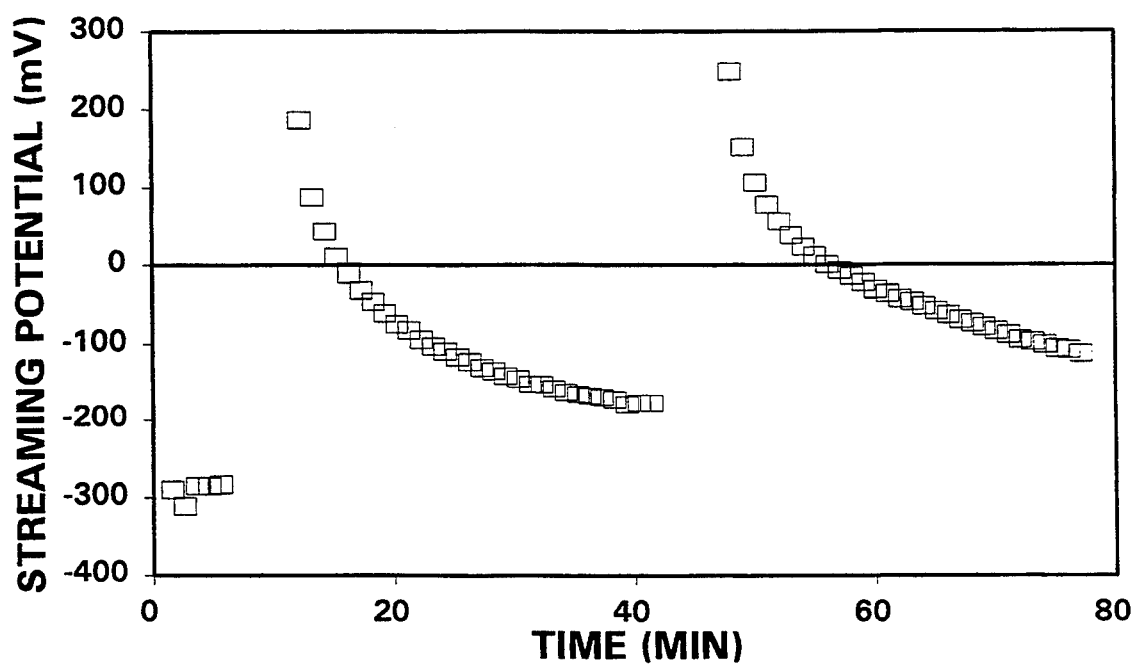
Figure 21C:
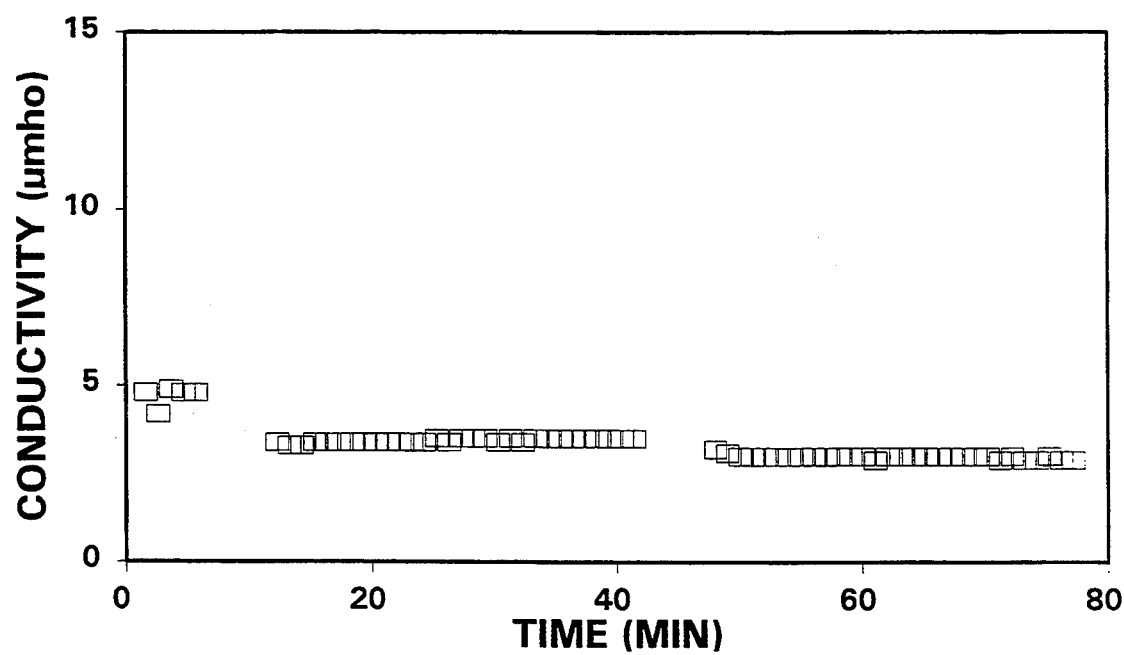
Figure 21D:
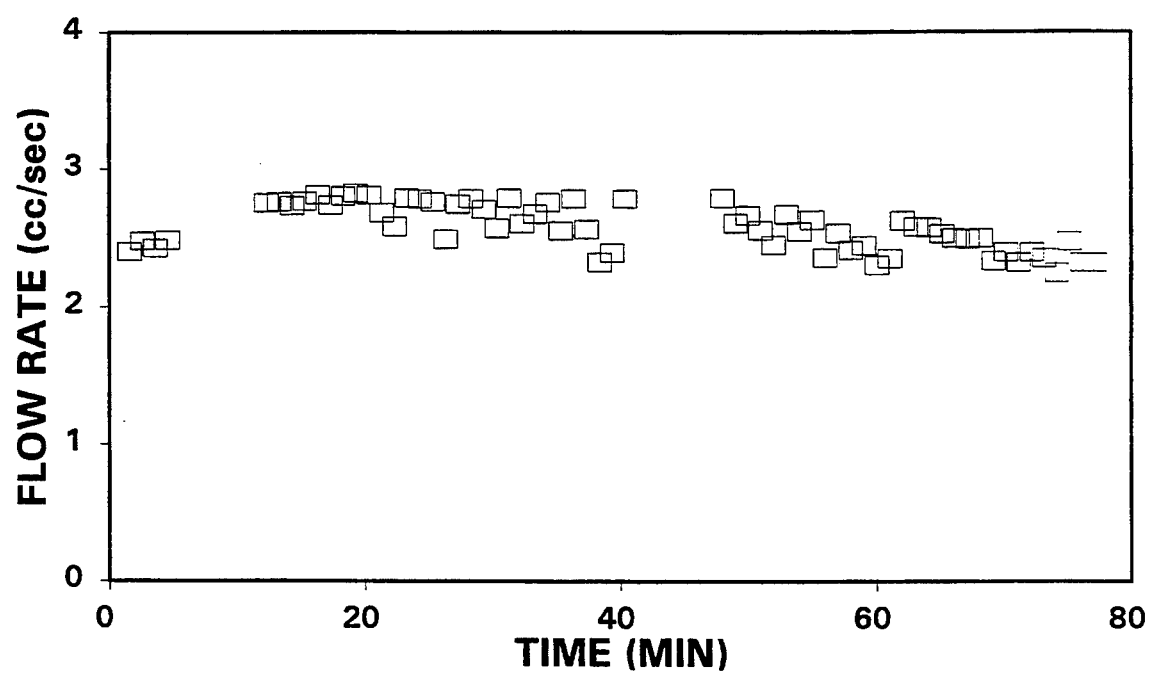
Figure 22A:
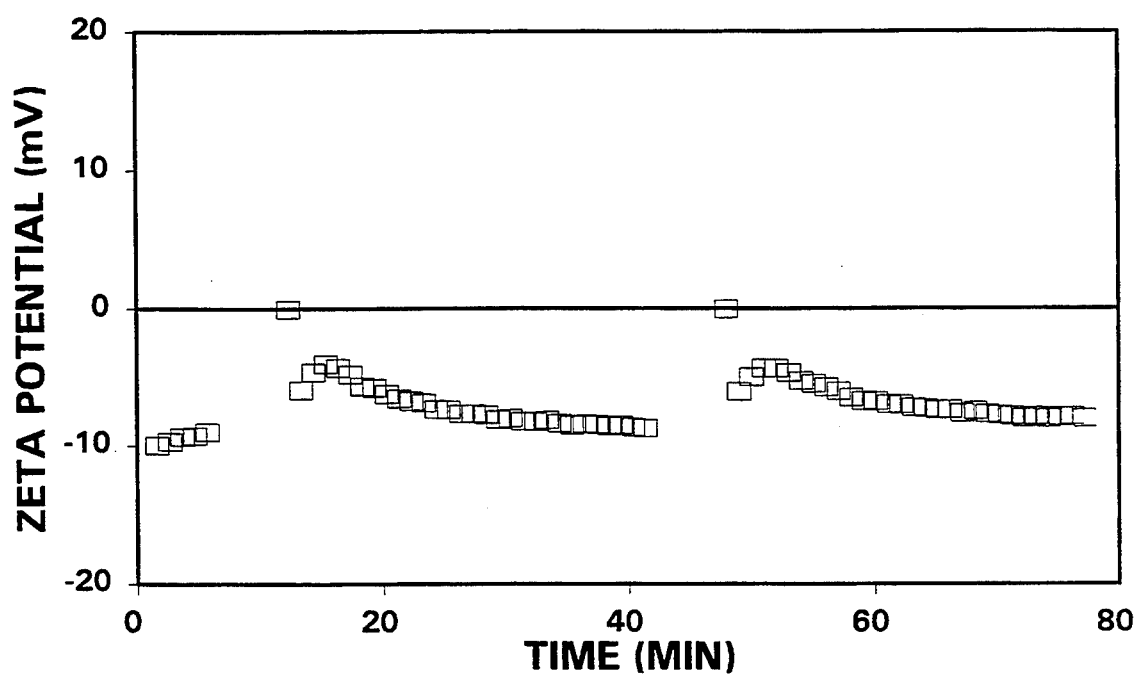
Figure 22B:
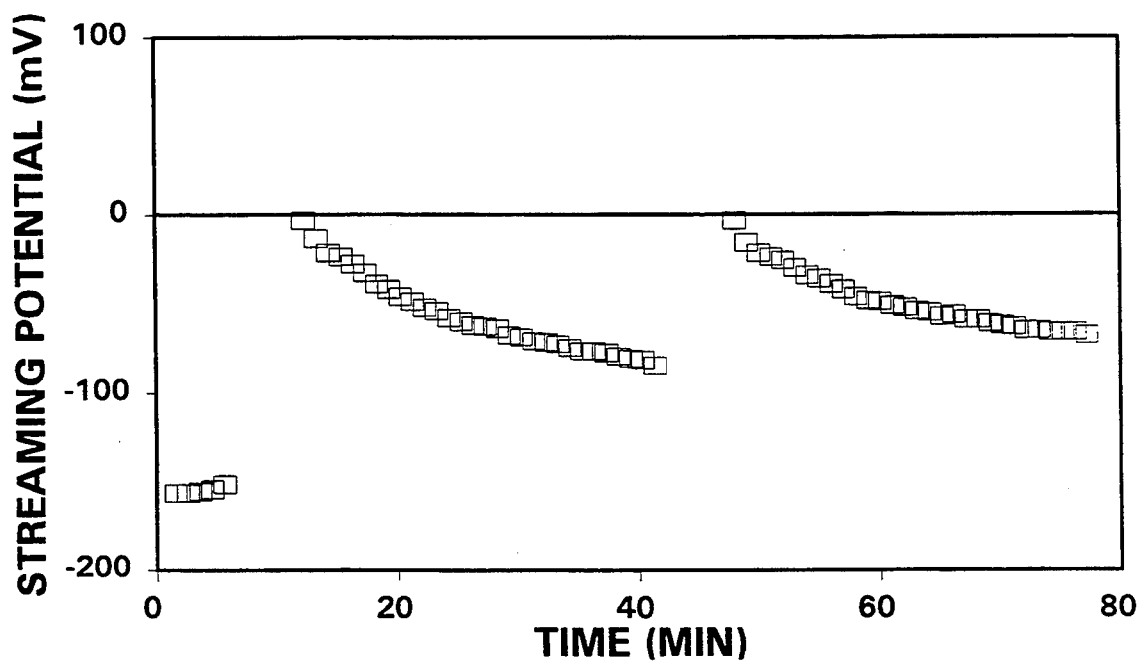
Figure 22C:
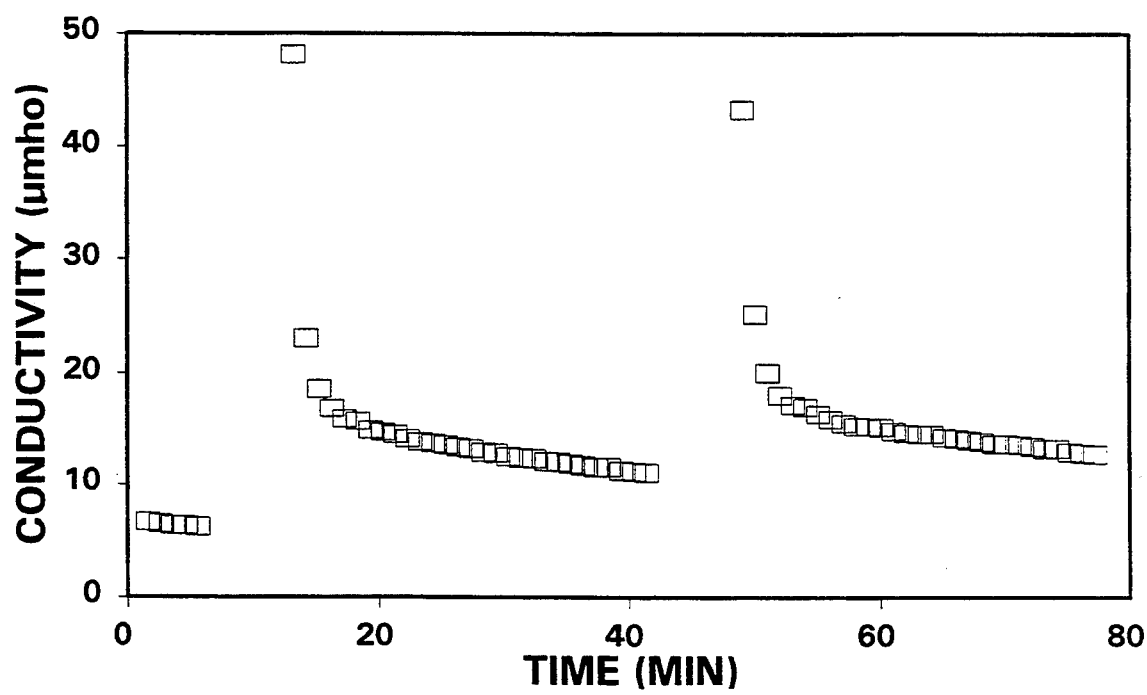
Figure 22D:
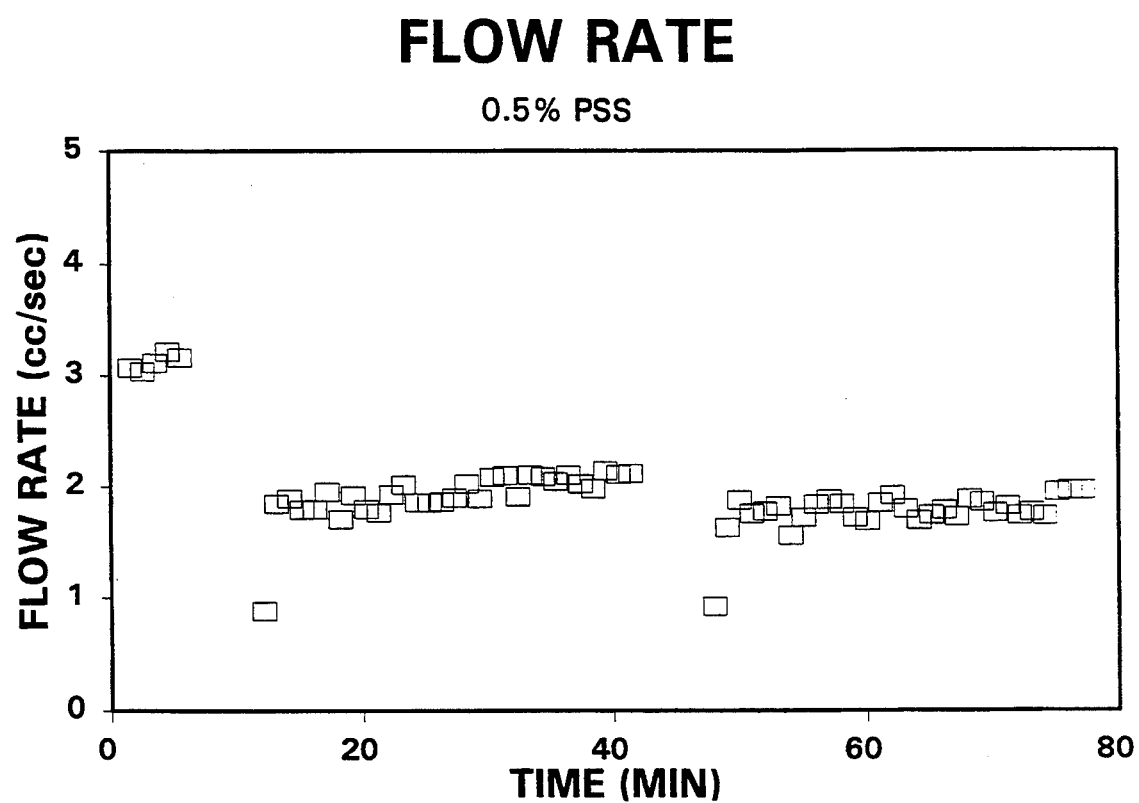
Figure 23A:
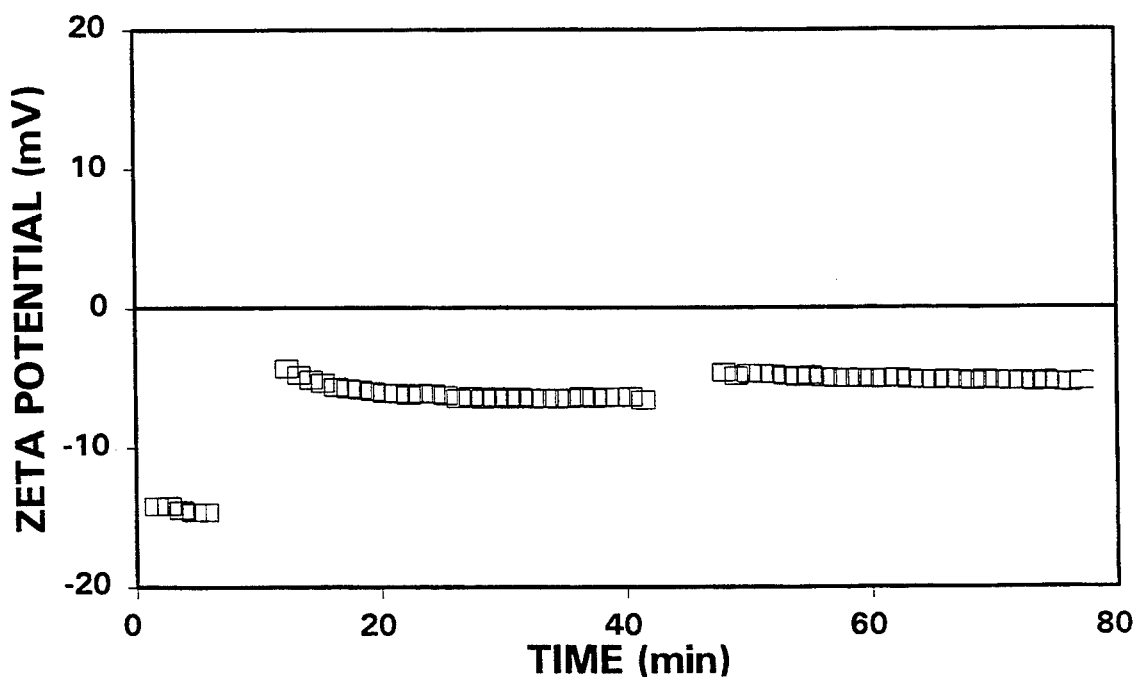
Figure 23B:
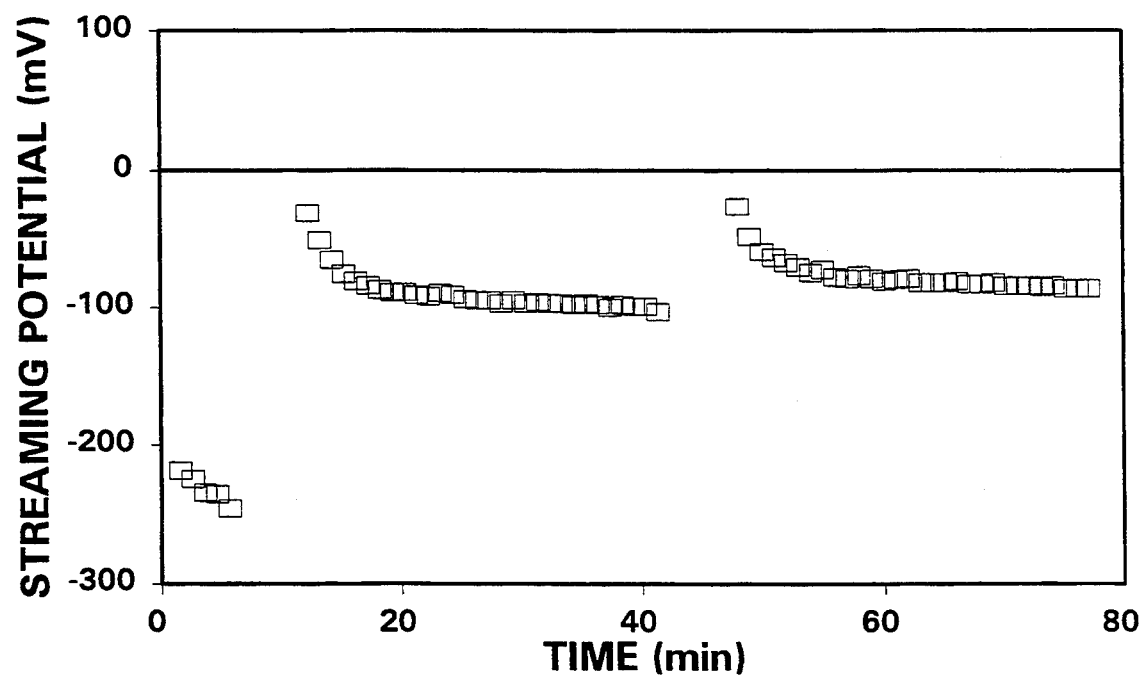
Figure 23C:
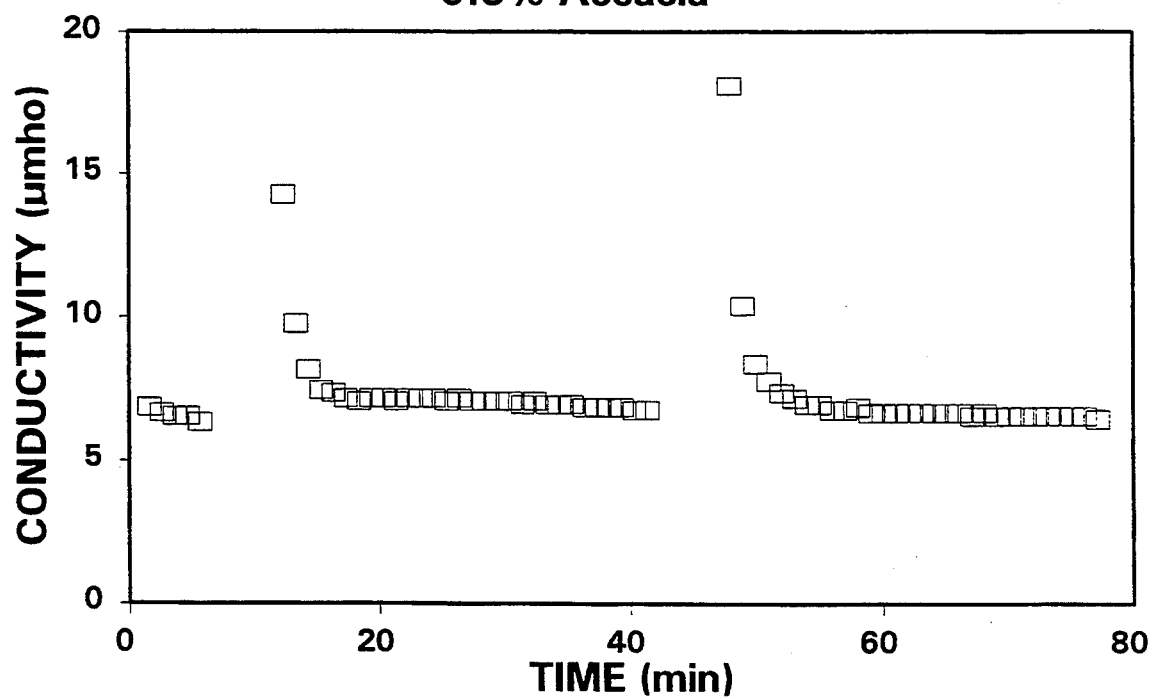
Figure 23D:
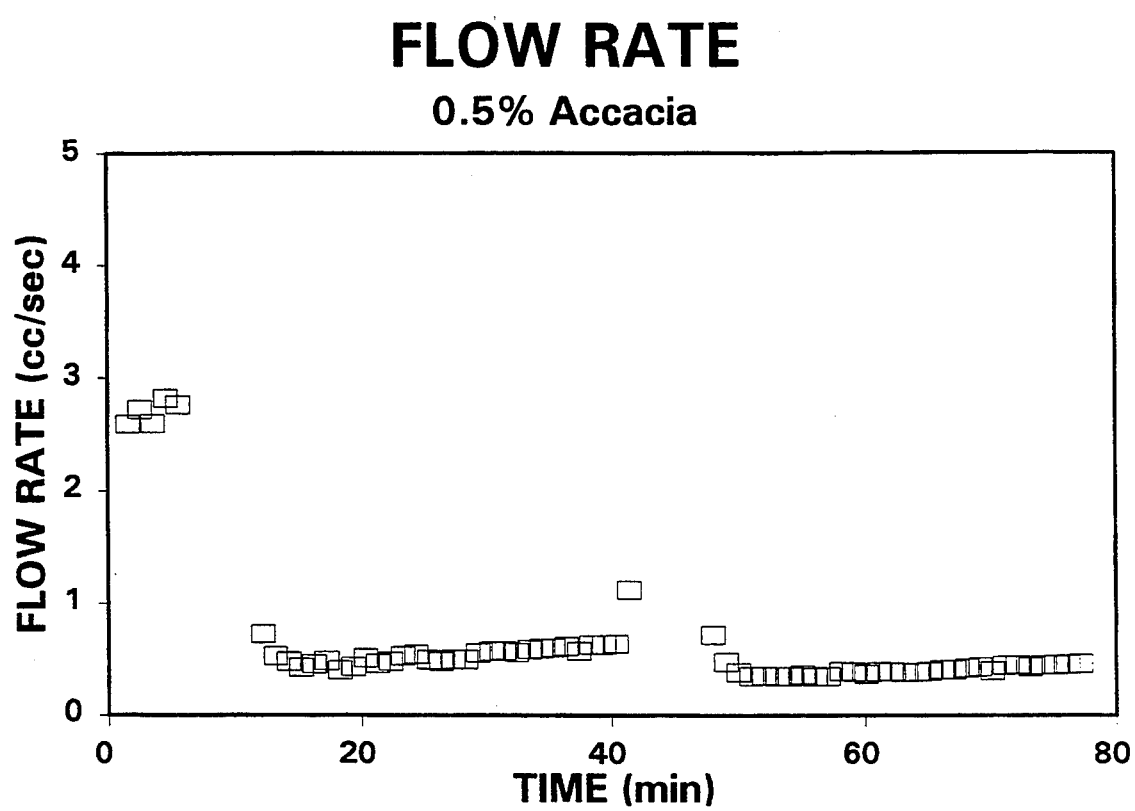
Figure 24A:
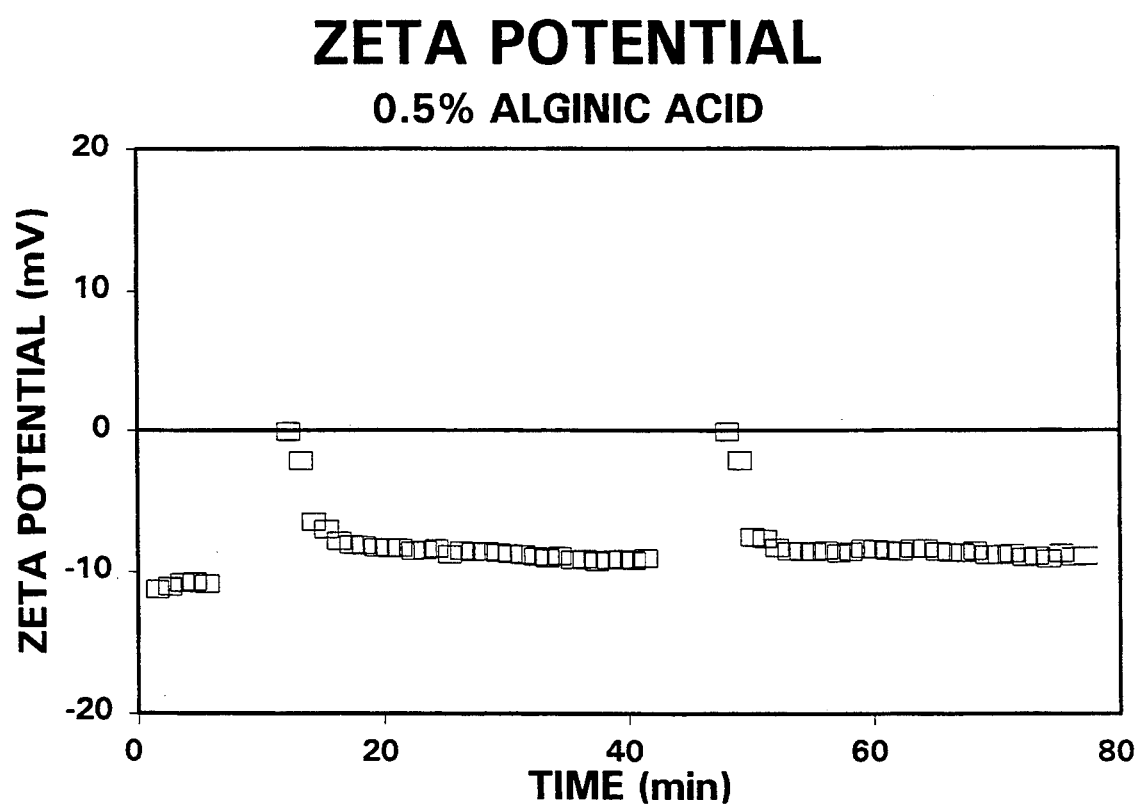
Figure 24B:
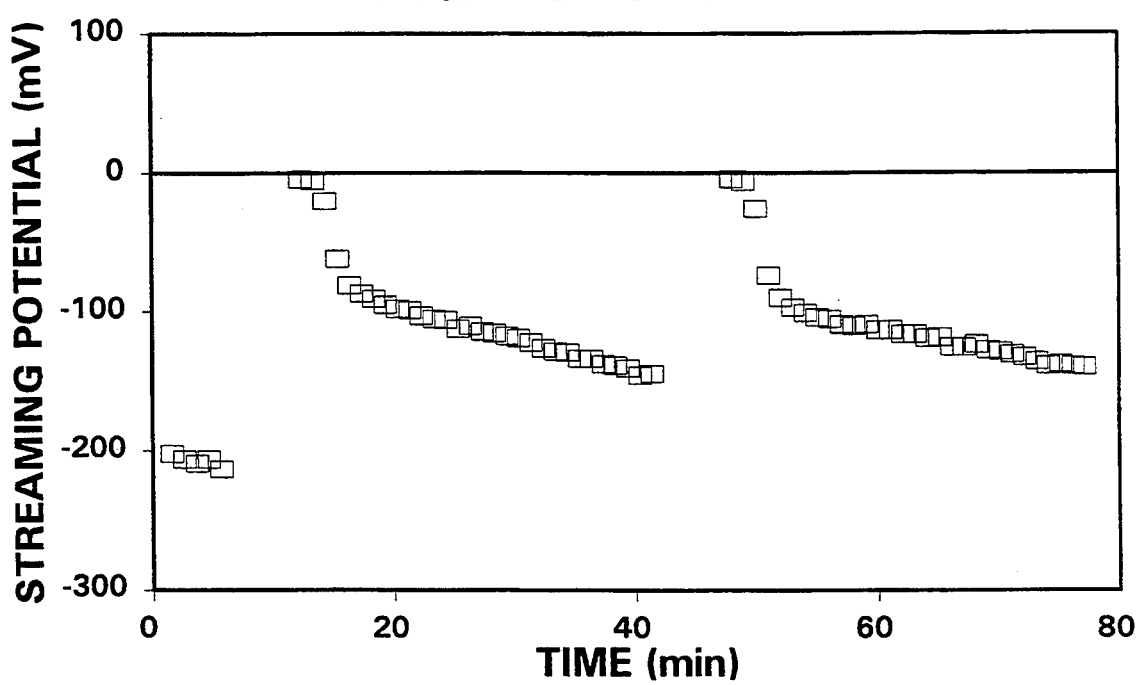
Figure 24C:
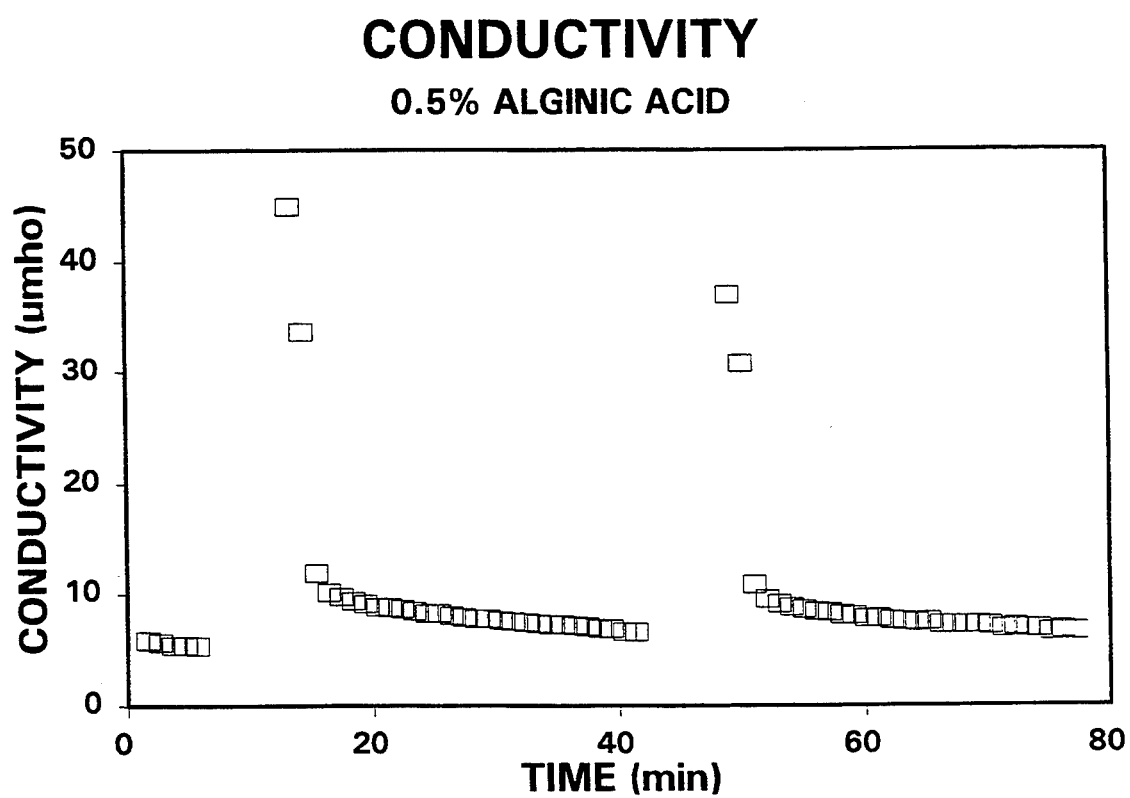
Figure 24D:
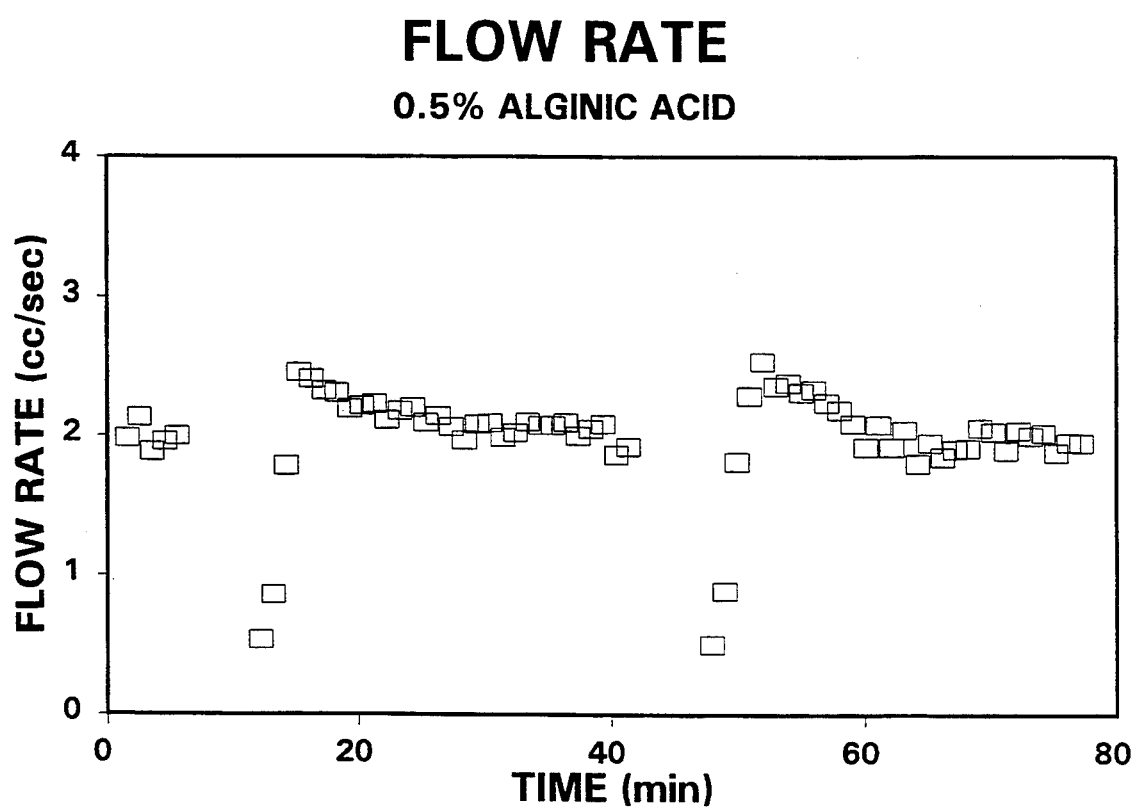
Figure 25A:
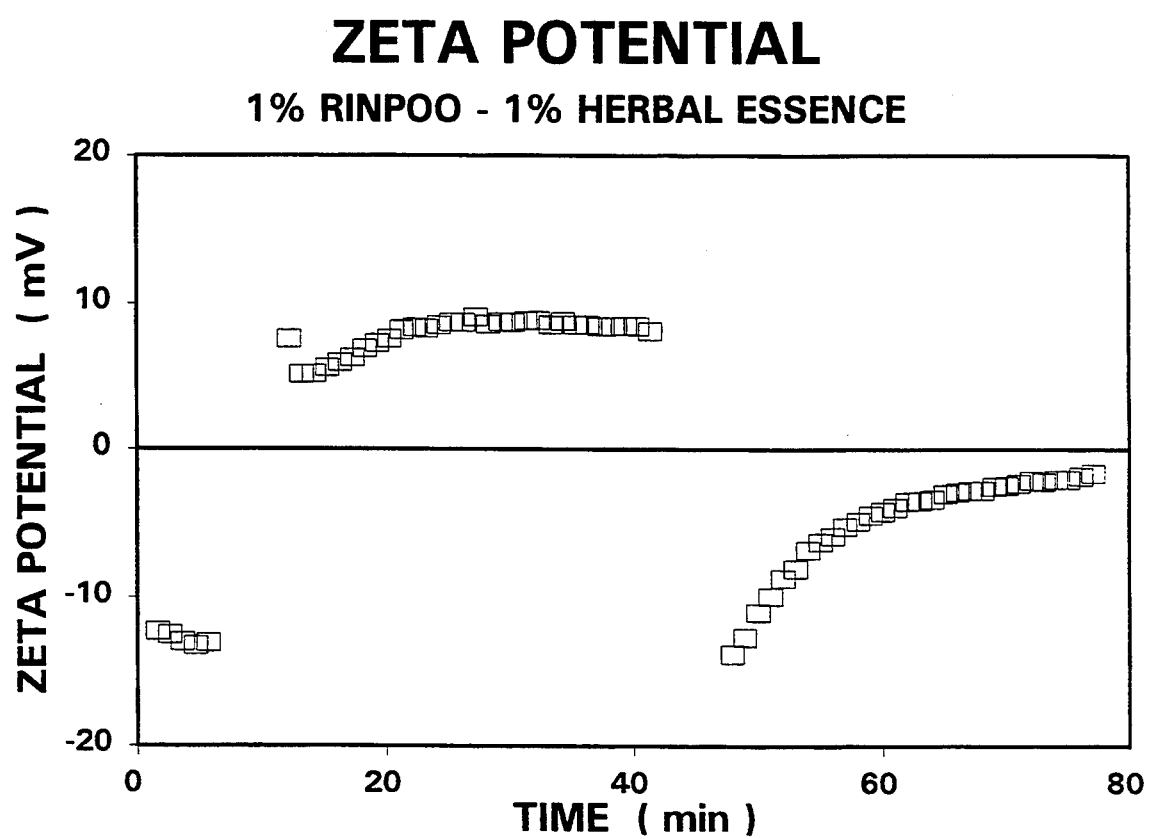
Figure 25B:
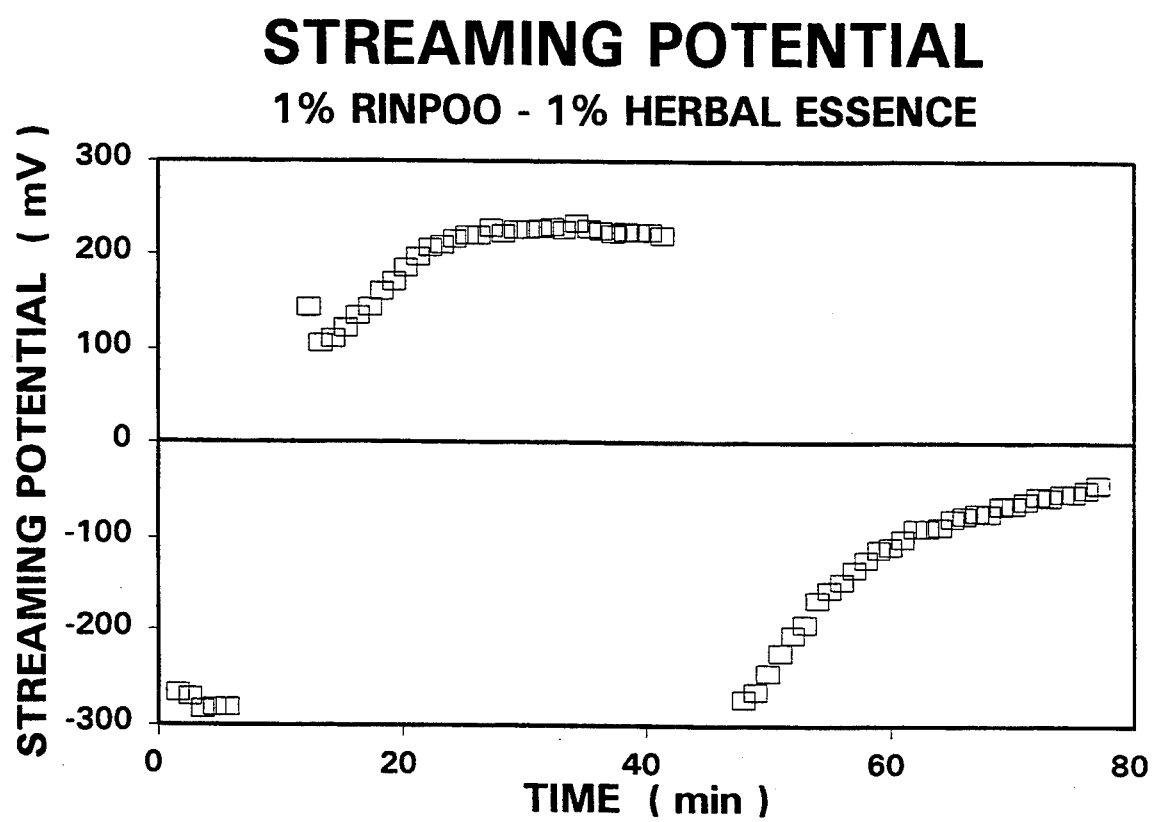
Figure 25C:
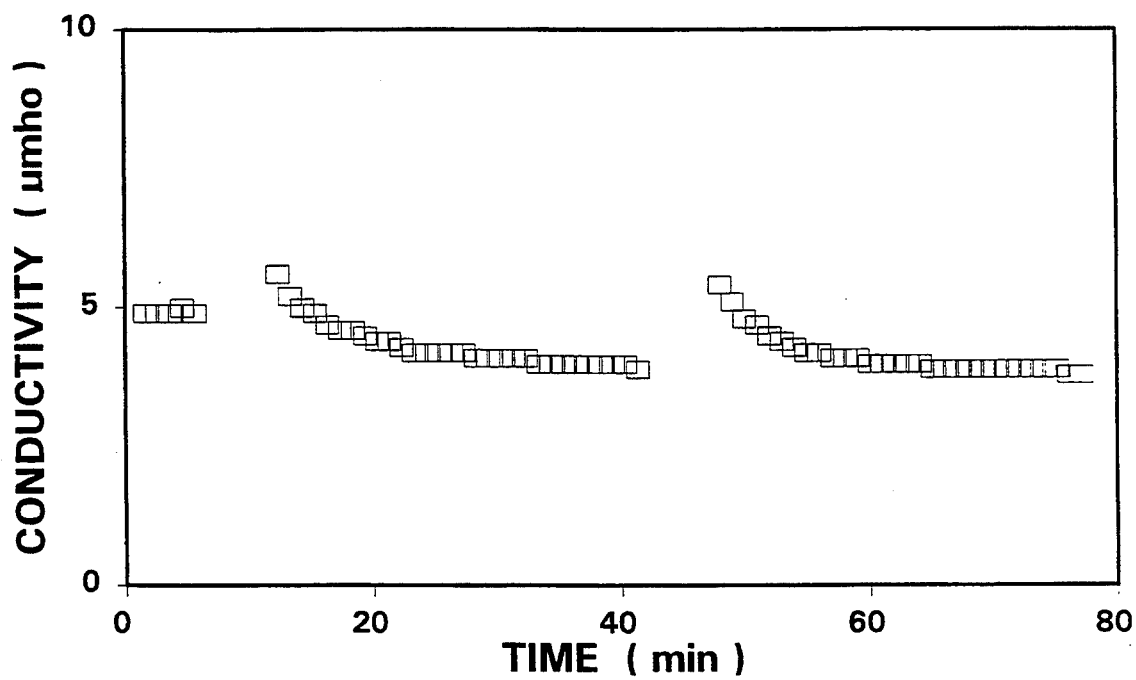
Figure 25D:
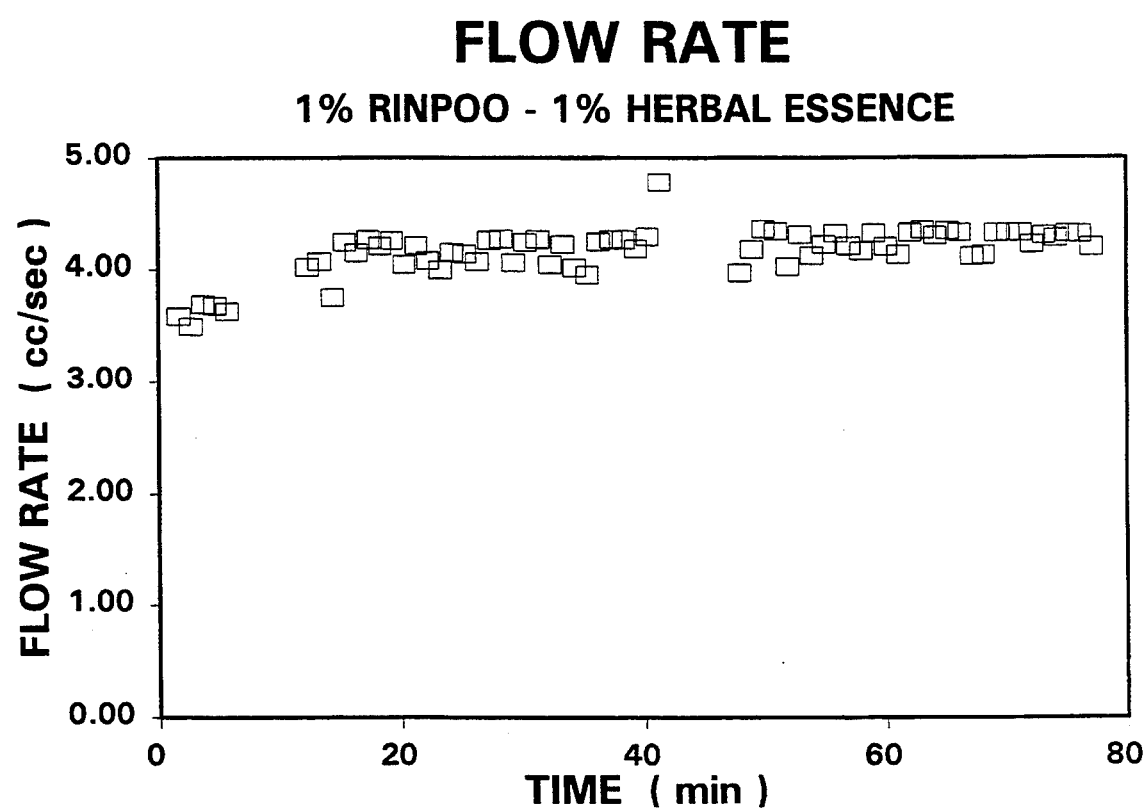
Figure 26A:
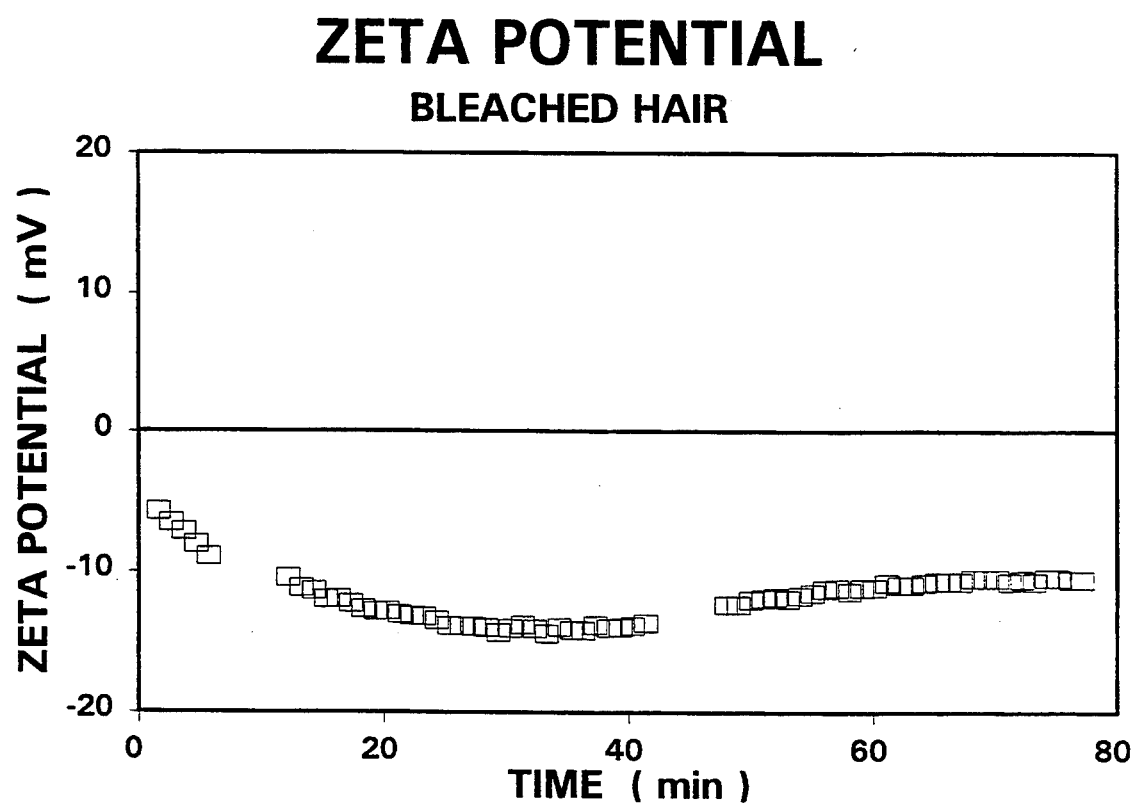
Figure 26B:
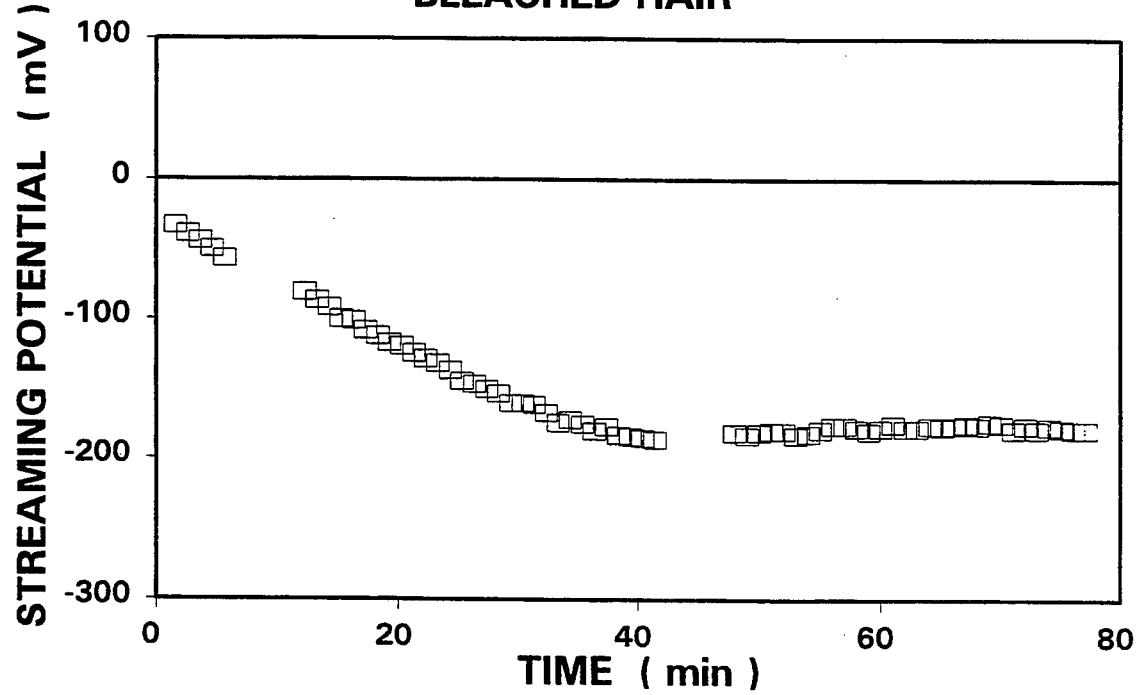
Figure 26C:
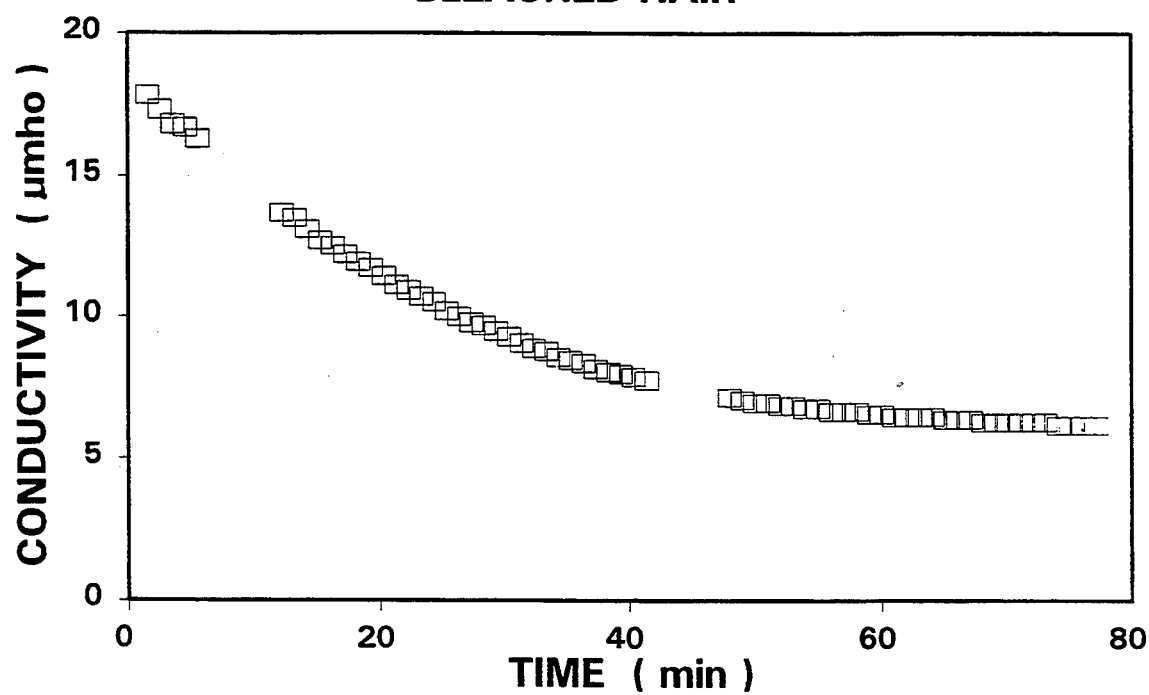
Figure 26D:
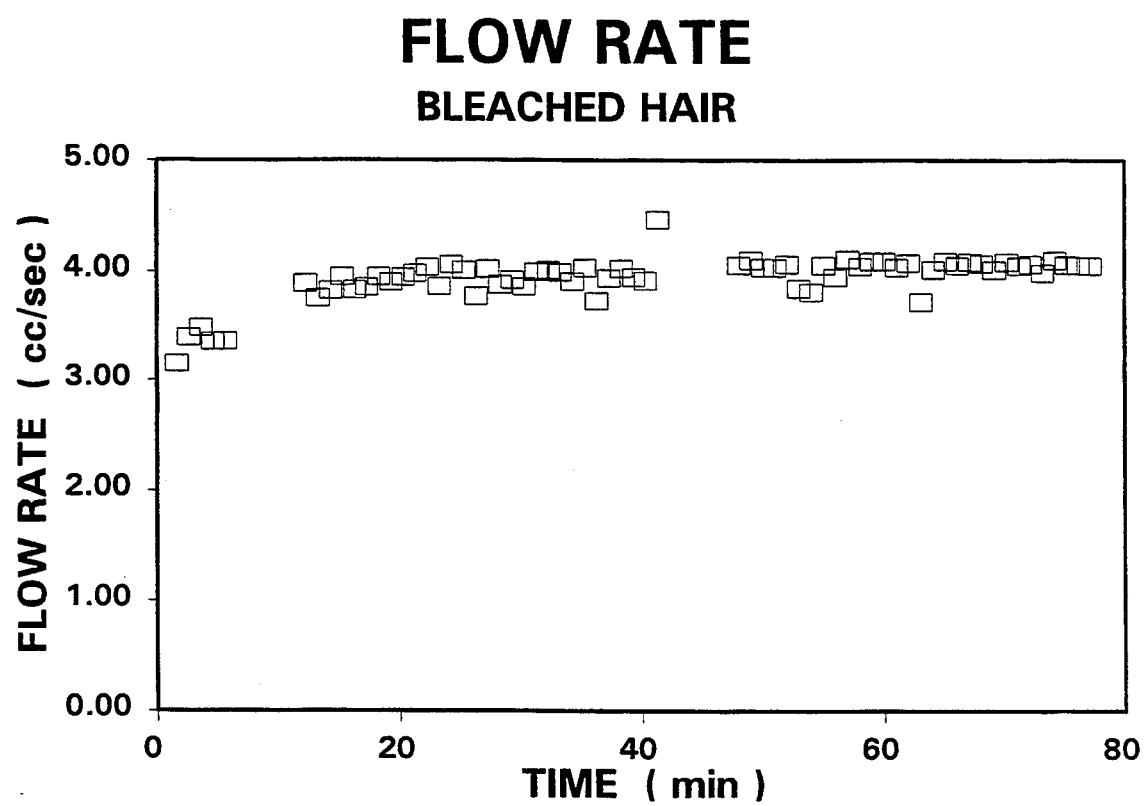
Figure 27A:
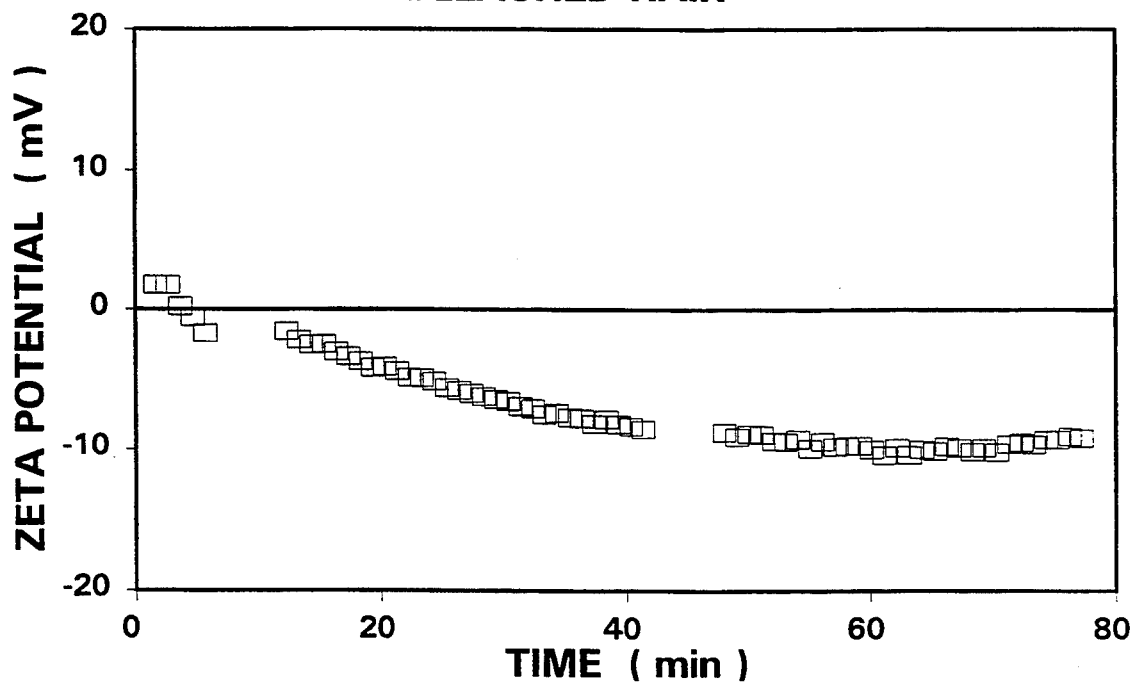
Figure 27B:
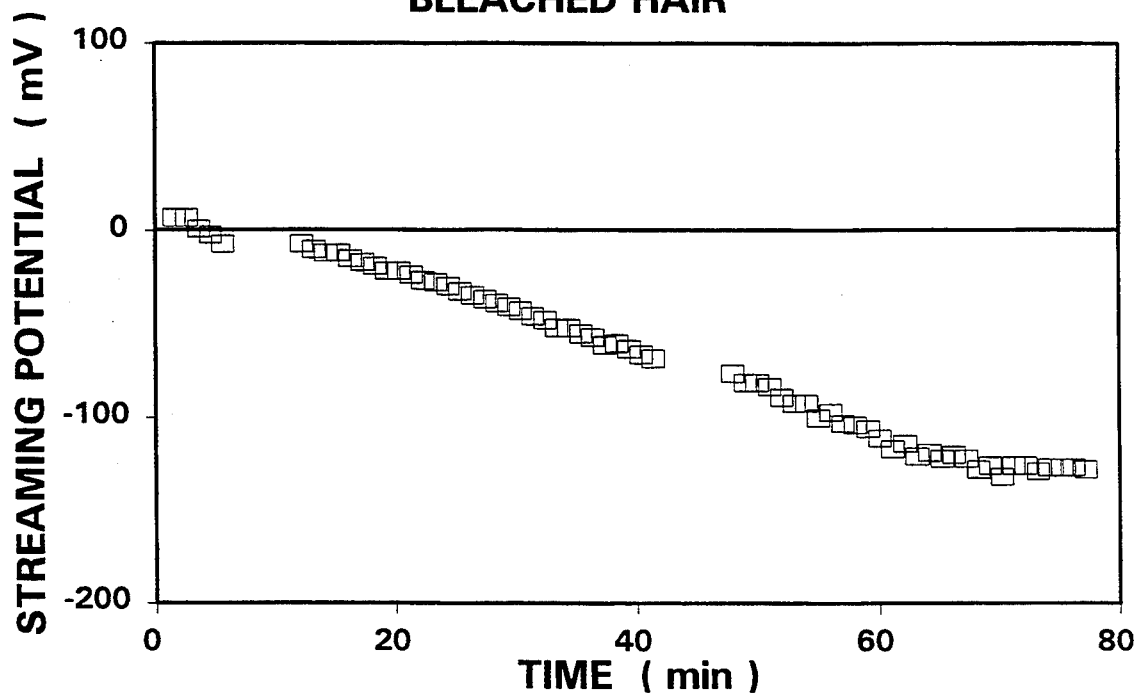
Figure 27C:
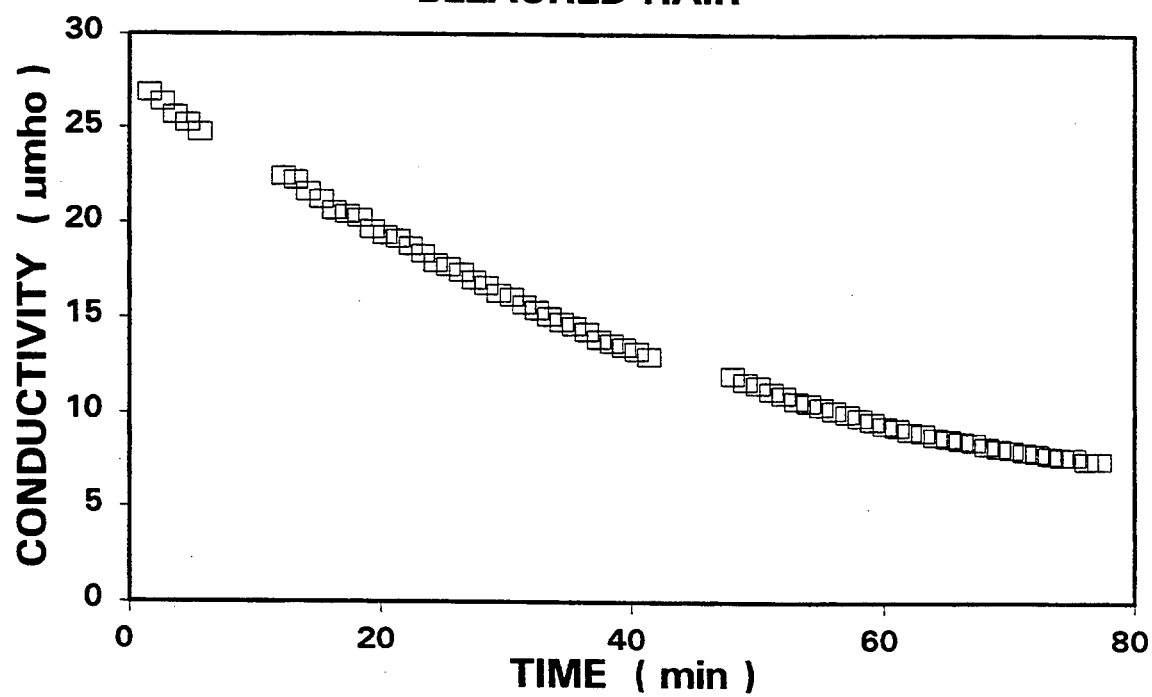
Figure 27D:
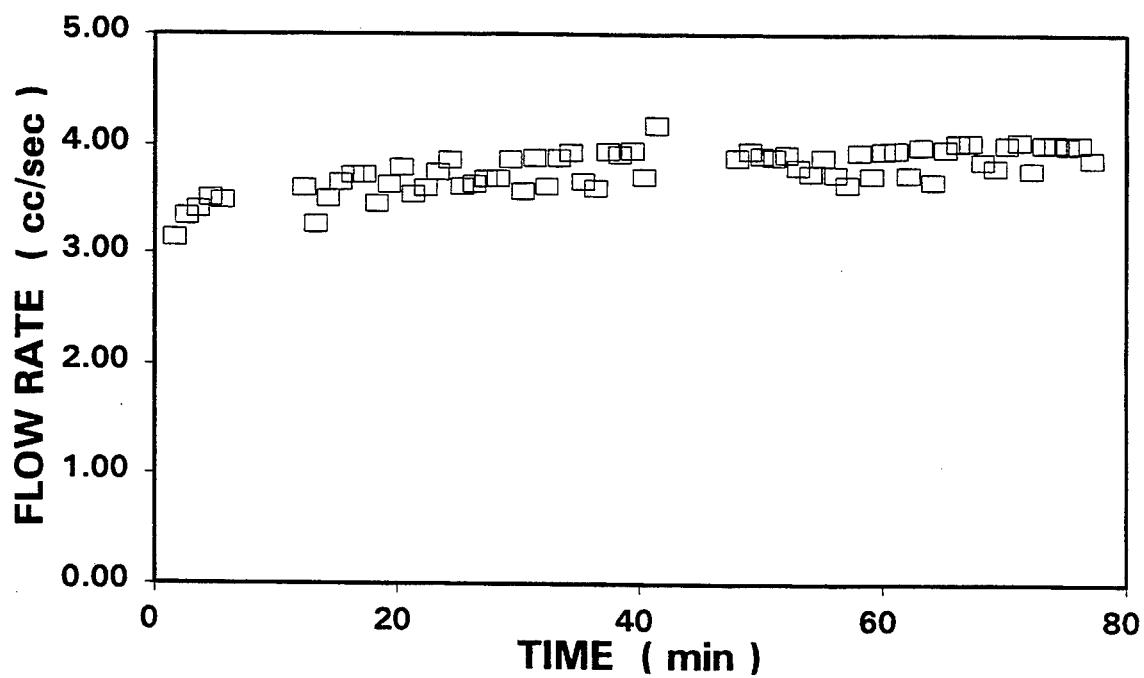

The system for flowing the various liquids through the flow cell 14 is shown in FIG. 2. It consists of a computer-controlled two-way valve 30 and an air hose leading from ballast 31 (air tank) to a source of pressurized air 32. A manometer 34 (pressure gauge) is mounted on ballast 31.

The valve 50 (flow interruptor) is controlled by computer 10, so that preferably the various liquids are supplied in pulses (spurts) to the flow cell 14. The timing may vary and depends on the air pressure used and the compression of the sample. The measurement stages may use from 5 to 100 "on" pulses (valve open) and preferably 10 to 50 pulses. The non-measurement stages (for example, treatment stage) may use 2 to 50 "on" pulses and preferably 5 to 10 pulses. The duration of the "on" pulses is 5 seconds to 5 minutes and preferably 15 seconds to 120 seconds. The duration of the "off" periods (between pulses) is from 5 seconds to 10 minutes and preferably 15 seconds to 120 seconds.

The ballast has an air hose 35 leading through manual two-way valves 36 and 37 to liquid reservoirs 38, 39 and 40. The reservoirs 38–40 are air-tight and have liquid flow output lines 41–43, respectively, which lead to manual two-way valves 44–46, respectively. The lines 41 and 42 are connected to computer controlled solenoid operated three-way valve 47 which, along with line 43, is connected to computer controlled solenoid operated three-way valve 48. The valves 47 and 48 and the other computer controlled valves are each electrically connected to, and controlled by, the solenoid and relay control 24 (FIG. 1). A pressure transducer 49 is connected to line 41 between valve 44 and valve 47. A liquid flow line leads from valve 48 through computer controlled two-way valve 50 flow interrupter to computer controlled three-way valve 51. The valve 51 is connected by a fluid flow line 52 to the computer controlled three-way valve 53 which is connected to one end of the flow cell 14 having a porous plug 54 therein. The opposite electrode disk of the flow cell 14 leads through computer controlled three-way valve 55 to a drain 56.

The following examples are illustrative of the use of the system and methods of the present invention. More specifically, the examples demonstrate:

- the resolving power of the technique which is capable of discriminating between polymers and surfactants having very small structural differences. Also, the ability to detect very small performance differences between various formulations such as shampoos and conditioners. This is achieved by the specific design of the instrument, with on-line treatment capability, as well as strict timing of the treatment and rinsing cycles;
- the importance of the simultaneous measurement of three parameters, namely, the streaming potential, conductivity and flow rate;
- the ability of the instrument to examine the effect and multiple treatments of the fibers with two different solutions; and
- the ability of the instrument to examine the rheological properties of aqueous solutions during the flow through the fiber plug modified by adsorption of polymers and surfactants.

Example 1

1. A test solution, to obtain base measurement, is poured into reservoirs 38 and 39 and consists of an aqueous solution of KCl at a concentration of 5 $10^{-5}$M. The water in these experiments is preferably highly purified by, for example, Barnstead Type D4700 NANOpure Deionization System, and characterized by specific conductivity 8–9 $10^{-7}$ mho/cm as measured by Orion Research Conductivity Meter Model 101 at 1 kHz.

2. The flow cell 14 is loaded with a plug 54 of untreated, cleaned human hair. The valves 47,48,51,53 and 55 are opened under computer control to provide 5 pulses of test solution, each pulse being a flow of 30 seconds (valve 50 open) followed by a non-flow of 30 seconds (valve 50 closed). The computer 10 obtains measurements of the background, i.e., rest potential, which it will subtract from the raw data.

3. The treatment liquid 1 from reservoir 39 (in this particular experiment a test solution of $5 \times 10^{-5}$M KCl) is then flowed through the flow cell 14 to provide a unidirectional stream, by opening of valves 47, 48, 51, 53 and 55, under computer control. The air pressure from ballast 31 is maintained at 12 cm Hg throughout the experiment. The stream of treatment liquid is pulsed, by the computer opening and closing the flow interrupter valve, in cycles of 30 seconds open and 30 seconds closed.

Measurements are automatically made, by operation of the relay 19, of the plug conductivity (by the conductivity meter 12) and voltage (by the electrometer 13). These meters provide the data from which the streaming potential and the specific plug conductivity may be derived by the computer 10. In addition, the permeability of the plug is measured by measuring the flow rate of the test solution. Five pulses of the treatment liquid 1, from reservoir 38, is flowed through the cell 14 over a 5-minute period. No data is recorded.

4. The test solution from reservoir 38 is then flowed through the flow cell 14. The flow is timed over 30 minutes so that 30 pulses occur, each of 30 seconds flow time, followed by 30 seconds of non-flow time. Data is recorded.

5. To test the effect of multiple treatments of hair, the treatment solution 1 from reservoir 39 was again flowed through the flow cell 14 for 5 minutes in five 30-second pulses.

6. The plug is remeasured by flowing the test solution from reservoir 38 through the flow cell 14, as in step 4.

FIGS. 3a–3d show the results of the measurements performed on untreated brown hair by using $5 \times 10^{-5}$M KCl in both test and treatment solutions. This control experiment demonstrates no significant change in electrokinetic parameters during rinsing with the test solution. A small increase in the plug permeability, as reflected by an increase in the flow rate, is ascribed to flow-induced rearrangement of hair in the plug.

Example 2

This example illustrates the use of the instrument for the analysis of the interactions of hair with anionic surfactants. The protocol was the same as that described for Example 1 with the exception that a surfactant solution was used as treatment liquid 1, and was placed in reservoir 39. Caucasian brown hair was used as a substrate and a fresh batch of untreated, cleaned hair was loaded into the flow cell 14 prior to each example. The first 5 data points in FIGS. 4–7 characterize the newly formed plug of untreated hair. The concentration of surfactant (treatment) solutions was 0.5%.

Investigation of the interactions of anionic detergents with hair were performed by using lauryl sulfates with various counterions such as sodium, ammonium, triethanolammonium (TEA), and magnesium. The results are presented in FIGS. 4–7. Both zeta potential and conductivity data suggest binding of sodium lauryl sulfate to hair with the possibility of deep penetration of the surfactant into the bulk of the fiber. After the treatment, the zeta potential of hair decreases due to an excess of free electrolyte in the plug, then increases to more negative values compared to the untreated hair surface, and finally decreases again after extended rinsing with the test solution. This produces a very broad peak on the curve of zeta potential as a function of time both after the first and the second treatment cycles. The variations in zeta potentials are accompanied by a slow decrease in the conductivity of the plug, suggesting continuous desorption of the surfactant from both the surface and possibly the bulk of the fiber. The sorption-desorption characteristics are essentially very similar for ammonium lauryl sulfate, the difference being that the peak in zeta potential versus time characteristics is shifted towards shorter times and the rate of the decrease in conductivity is faster. For TEA-lauryl sulfate, there is a significant lowering of zeta potential immediately after the treatment cycle, followed by a rapid removal of the surfactant from the plug. Magnesium lauryl sulfate shows virtually no binding to hair and is very rapidly rinsed out from the plug.

Example 3

This example illustrates the use of the instrument for the analysis of the interactions of hair with complete, multicomponent shampoo formulations. It demonstrates the sensitivity of the instrument and illustrates the importance of the simultaneous measurement of the plug permeability and electrokinetic parameters such as the streaming potential and conductivity. The procedure employed was the same as that described for Example 2. Caucasian brown hair was used as a substrate and a fresh batch of untreated, cleaned hair was loaded into the flow cell 14 prior to each experiment. The first five data points in FIGS. 8–10 characterize the newly formed plug of untreated hair. The concentration of the treatment solutions was 1.0% of the original formulation.

FIGS. 8a–8d presents the data obtained for the commercial product Herbal Essence ™ manufactured by Clairol. This is a simple, strong cleansing formulation based on sodium C14–16 olefin sulphonate with no conditioning agents. The zeta potential trace as well as the conductivity data suggest relatively strong binding of the anionics to hair. The flow (permeability) measurements are similar to those reported for the test solutions, suggesting that no deposition and surface modification occurs in the process of shampooing.

FIGS. 9a–9d presents the data obtained from the commercial product Condition Revitalizing Formula ™ for Normal Hair manufactured by Clairol. The formulation is based on sodium lauryl sulfate with a relatively high concentration of protein hydrolisates as conditioning agents. Amphoteric protein does not seem to have any significant effect on zeta potential. Conductivity decrease is very slow, suggesting strong binding of the anionic detergent to the hair surface. Permeability of the plug is reduced significantly after each treatment, which is probably related to deposition of the protection hydrolisate either by itself or in the form of complexes with other components of the formulation.

FIGS. 10a–10d presents the data obtained for a commercial product Flex & Go ™ manufactured by Revlon. This system is based on anionic detergents with cationic guar gum as a conditioning agent. The zeta potential trace clearly shows less anionic (less negative) nature of the hair surface as a result of the adsorption of cationic polymer. The data suggests initial deposition of guar gum—anionic detergent complex, with subsequent desorption of the surfactants during rinsing. Also, a reduction in plug permeability is evident after the first and the second treatment cycles.

Example 4

This example illustrates the use of the instrument for the analysis of the interactions of hair with cationic surfactants. The procedure was the same as that described for Example 2. Caucasian brown hair was used as a substrate and a fresh batch of untreated, cleaned hair was loaded into the flow cell 14 prior to each experiment. The first five data points in FIGS. 11-12 characterize the newly formed plug of untreated hair. The concentration of surfactant (treatment) solutions was 0.5%.

FIGS. 11a-11d show zeta potential, flow rate, conductivity and streaming potential traces obtained for stearalkonium chloride. Following the treatment with a solution of a conditioner, there is a reversal of the sign of the streaming potential as a result of the adsorption of cationics on the fiber surface. The streaming potential then decreases, because of desorption of cationic species, into the test solution during rinsing, and reaches an equilibrium value which reflects the presence of a stable layer of conditioner on the surface. The maximum value of the streaming potential is primarily determined by the initially adsorbed amount of cationic surfactant (related to the concentration of cationic species in the formulation as well as the morphology of the system), density of the bound layer, nature and the number of ionic groups in a surfactant (or oil) molecule, or the nature of the counter-ions. The equilibrium value of the streaming potential is determined by the amount of irreversibly adsorbed conditioning agent and this, in turn, is determined by the surfactant or oil type, its HLB characteristics, etc. The conductivity of the plug returned to the baseline or even smaller value within a few cycles following the treatment, indicating that the fiber does not release appreciable amounts of adsorbed surfactant into the streaming solution. The flow rate results indicate a very small reduction in the permeability of the plug after both the first and the second treatment cycles. The flow data can also be used for estimation of the hydrodynamic thickness of the adsorbed layer of surfactant.

FIGS. 12a-12d shows zeta potential, flow rate, conductivity and streaming potential traces obtained for cetyltrimethylammonium bromide. This surfactant has lower affinity to hair surface as judged from the dependence of zeta potential as a function of time. The equilibrium value of zeta potential is more negative than that determined for stearalkonium chloride suggesting a smaller concentration of cetyltrimethylamonium chloride on hair surface. Also, a decrease in the flow rate, observed immediately after the treatment cycle, is related to relatively high viscosity of cetyltrimethylammonium bromide solution.

Example 5

This example illustrates the use of the instrument for the analysis of the interactions of hair with hair conditioning formulations. It illustrates the importance of the simultaneous measurement of the plug permeability and electrokinetic parameters such as the streaming potential and conductivity. The procedure employed was the same as that described for Example 2. Caucasian brown hair was used as a substrate and a fresh batch of untreated, cleaned hair was loaded into the flow cell 14 prior to each experiment. The first five data points in FIGS. 13 and 14 characterize the newly formed plug of untreated hair. The concentration of the treatment solutions was 1% of the original formulation.

Formulation A (FIGS. 13a-13d) is a prototype conditioner based on the complex between fatty amine and fatty acid (with the excess of fatty amine) and aminofunctional silicone oil. The Zeta potential trace suggests a relatively low degree of fiber surface modification is obtained after the treatment and rinsing. On the other hand, a significant decrease in the permeability of the plug indicates deposition of a relatively thick layer of the conditioning agents on hair surfaces.

Formulation B (FIGS. 14a-14d) (maximizing) is a prototype conditioner based on cationic surfactant. The application of this product results in a relatively small increase in the cationicity of the fiber surface. This result is also supported by the measurements of permeability which also indicate a formulation of a thin modifying layer on the fiber surface.

Example 6

This example illustrates the use of the instrument for the analysis of the interactions of hair with cationic polymers. The procedure employed was the same as that described for Example 1. Caucasian brown hair was used as a substrate and a fresh batch of untreated, cleaned hair was loaded into the flow cell 14 prior to each experiment. The first five data points in FIGS. 15-17 characterize the newly formed plug of untreated hair. The concentration of polymer (treatment) solution was 0.5%.

FIGS. 15a-17d present the data obtained for three cationic polymers with the charge densities of the polymer chain decreasing in the following order: Merquat 100 (poly)dimethyl diallyl ammonium chloride))<Merquat 550 (co(acrylamidedimethyl diallyl ammonium chloride))<Merquat 280 (co(acrylic acid—dimethyl diallyl ammonium chloride). These are three different polymer solutions. Between each polymer solution the apparatus is cleaned. In all cases, following the treatment with a polymer solution, there is a reversal of the sign of the zeta potential as a result of the adsorption of cationics on the fiber surface. For Merquats 100 and 550, the zeta potential remains high throughout the rinsing cycle while the zeta potential of hair treated with Merquat 280 is decreased to low positive value by rinsing with the test solution. Adsorption of cationic polymers does not affect the permeability of a hair plug except immediately after the treatment with viscous solutions (Merquat 550 and Merquat 100). This result suggests that the adsorbed layer is relatively thin, probably below 550A. Conductivity of the plug, which increases during the treatment stage due to the presence of electrolytic species, is reduced to below baseline values within a few rinsing cycles. Hair with an adsorbed layer of cationic polymer is thus characterized by lower surface conductivity than untreated hair.

Example 7

This example illustrates the use of the instrument for the analysis of the interactions of hair with aqueous dispersions such as silicone oil emulsions. It demonstrates the usefulness of the instrument for predicting which dispersions can interact with hair, and consequently be used as hair conditioners. The procedure was the same as that described in Example 1. Caucasian brown hair was used as a substrate and a fresh batch of untreated, cleaned hair was loaded into the flow cell 14 prior to each run (each emulsion). The first five data points in FIGS. 18–21 characterize the newly formed plug of untreated hair. The concentration of emulsion (treatment) solutions was 0.5%.

FIGS. 18a–21d present the data obtained for various types of silicone emulsions: (i) neutral emulsion DC 347 (manufactured by Dow Corning) which consists of unmodified poly(dimethylsiloxane) polymer emulsified in a anionic surfactant system (FIGS. 18a–18d), (ii) cationic emulsion DC Q2-7224 (manufactured by Dow Corning) which consists of an aminofunctional silicone polymer emulsified by a nonionic surfactant system (FIGS. 19a–19d), (iii) cationic emulsion of DC 929 (manufactured by Dow Corning) which consists of an aminofunctional silicone polymer emulsified in a cationic-nonionic surfactant system (FIGS. 20a–20d), and (iv) cationic microemulsion SM 2115 (manufactured by General Electric) which consists of high-amine content aminofunctional silicone microemulsified by a nonionic surfactant system (FIGS. 21a–21d). Nonionic emulsion 347 modifies the surface only to a small extent as judged from relatively small changes in the streaming and zeta potentials. Significant binding is evident for cationic emulsion DC Q2-7224 which reverses the sign of the zeta potential of hair surface from negative to positive. Both DC 929 and SM 2115 show binding with the sign reversal immediately after the treatment cycle, the effect gradually disappearing on rinsing with the test solution. Both of these emulsions produce a significant and durable decrease in the conductivity of the plug.

Example 8

This example demonstrates the ability of the instrument to detect the adsorption of an anionic polymer, poly(styrene sulphonate) by using permeability (flow rate) measurements. This polymer has only a small influence on the zeta potential of the fiber. The procedure was the same as that described for Example 2. Caucasian brown hair was used as a substrate and a fresh batch of untreated, cleaned hair was loaded into the flow cell 14 prior to each experiment. The first five data points in FIGS. 22a–22d characterize the newly formed plug of untreated hair. The concentration of poly(styrene sulphonate) in the treatment solution was 0.5%.

Since hair surface is predominantly anionic at neutral pH, and anionic polymers are not known to significantly modify (condition) the surface properties of hair, electrokinetic and permeability analysis was not expected to show interactions between anionic polymers and hair. Surprisingly, poly(styrene sulphonate) showed substantive binding to hair as evidenced by a small reduction in zeta potential combined with a significant change in the permeability of the plug (FIGS. 22a–22d). Additionally, a slow desorption of polymer from hair is suggested by the conductivity measurements.

Example 9

This example demonstrates the ability of the instrument to detect the effect of the adsorbed polymer on the flow behavior of the aqueous solution through the fiber plug. The experimental procedure employed was the same as that described for Example 1, with the exception that the polymer solutions were used as treatment liquids 1 and were placed in reservoir 39. Caucasian brown hair was used as a substrate and a fresh batch of untreated, cleaned hair was loaded into the flow cell 14 prior to each run. The first five data points in FIGS. 23a–23d and 24a–24d characterize the newly formed plug of untreated hair. Aqueous solutions of natural polysaccharides, accacia and alginic acid were used as the treatment solutions at a concentration of 0.5%.

The permeability data obtained for acacia (FIGS. 23a–23d) and alginic acid (FIGS. 24a–24d) reveal a phenomenon of slip flow behavior in the presence of adsorbed polymer layer in equilibrium with polymer solution. It is reflected by an increased rate of flow of the test solution through the plug immediately after the treatment, as long as an adsorbed layer of polymer remains on the surface. The slip flow is transient, and disappears after the desorption of polymer from hair. It is also more clearly evident for alginic acid (the permeability of a hair plug treated with acacia is significantly reduced; a small increase in flow rate immediately after the treatment, when hair is still in contact with polymer solution suggests a slip flow phenomenon). Note that the anionic polymers of Example 8, as well as cationic polymers (Example 6) do not exhibit slip flow behavior, and no enhancement in plug permeability is observed after the treatment with these polymers.

Example 10

This example demonstrates the ability of the instrument to examine the effect of two consecutive treatments on the surface of hair. The experimental procedure employed was the same as that described for Example 1, with the exception that 1% solutions of specified formulations were used as treatment liquids 1 and 2, and were placed in reservoirs 39 and 40, respectively. Caucasian brown hair was used as a substrate and a fresh batch of untreated, cleaned hair was loaded into the flow cell 14 prior to each run. The first five data points in FIGS. 25a–25d characterize the newly formed plug of untreated hair. 1% aqueous solutions of shampoo formulations, Rinpoo TM (manufactured by Shiseido) and Herbal Essence TM (manufactured by Clairol, Inc.) were used as the treatment solutions.

FIGS. 25a–25d present the results obtained when hair was first treated with a conditioning shampoo Rinpoo TM followed by a cleansing (nonconditioning) shampoo Herbal Essence TM. The objective was to find out to what extent a cleansing shampoo can remove the surface deposits left by the treatment with a conditioning shampoo. Rinpoo TM formulations are based on amphoteric surfactants with anionic surfactant—cationic surfactant complex as a conditioning agent. The hair surface modification after the treatment with Rinpoo TM is significant, as can be judged by the reversal of the sign of zeta potential from negative to positive values. Subsequently treatment of hair with Herbal Essence TM shampoo) partially removes the cationic surfactant complex from hair.

Example 11

This example demonstrates the ability of the instrument to distinguish between hair damaged to different extents by reactive chemical treatment, such as bleaching. The protocol employed was the same as that described for Example 1 (control experiment; test solution poured into reservoir 38, and used as a treatment solution). Two samples of bleached hair, with various degrees of damage characterized by alkaline solubility test, were used as substrates, and were loaded into the flow cell 14 prior to each run.

FIGS. 26a–26d and 27a–27d present the data obtained for hair samples bleached by experimental compositions containing hydrogen peroxide, ammonium hydroxide, sodium persulfate and ammonium persulfate, respectively. Two samples of hair were bleached to produce different degrees of fiber damage, 16% (formulation A, FIGS. 26a–26d) and 23% (formulation B, FIGS. 27a–27d) as determined by the alkaline solubility test. The electrokinetic and conductivity data presented in FIGS. 26a–27d show that the streaming potential, zeta potential, and conductivity change during rinsing with the test solution, probably as a result of the fibers leaching out electrolytic species such as ammonium hydroxide, sodium persulfate, and ammonium persulfate absorbed during the treatment. The conductivity of the plug gradually decreases as the electrolytes diffuse out of the fiber structure and are washed off the plug by fresh portions of the streaming solution. The initial conductivity of hair, characterized by higher alkaline solubility (23%), is higher than that found for less damaged hair (alkaline solubility 16%, FIGS. 26). Also, the conductivity of less damaged hair reaches a constant value within the time frame of the experiment (75 minutes rinsing, FIGS. 26a–26d). Hair damaged to a greater extent shows a considerable rate of conductivity which decreases after 75 minutes rinsing with the best solution. For both samples of damaged hair, a decrease in conductivity is accompanied by a decrease in zeta potential. On the other hand, bleaching did not have a detectable effect on the permeability of the fiber plugs.

We claim:

1. A system for the measurement of streaming potential by flow of a liquid through a permeable sample to provide information concerning adsorption/desorption of colloids on fibers of the permeable sample, the system including:
   (a) a flow cell adapted to removably hold the permeable sample, said permeable sample being used to conduct a series of measurements while being continuously retained within the flow cell, said flow cell having first and second orifices and a body portion adapted to permit the flow of liquid from the first orifice through the cell body portion and permeable sample to the second orifice;
   (b) a programmable electronic computer system means to provide a program of electric control signals to control the flow of liquids through the flow cell;
   (c) at least first and second air-tight liquid reservoirs, the first reservoir containing a first liquid which is a test solution comprising a dilute solution of an electrolyte to provide a set of base measurements and the second reservoir containing a second liquid whose effect on the permeable sample is to be tested;
   (d) a series of liquid flow lines leading from the first and second reservoirs to at least one of said flow cell orifices;
   (e) a supply of pressurized air connected to the first and second reservoirs to apply pressure to the liquids therein so that said liquids may flow through said liquid flow lines;
   (f) a pair of electrodes within the flow cell adapted to be positioned at opposite ends of the permeable sample therein;
   (g) an electrometer electrically connected to the electrodes and to the computer system means to measure electrical potential across the electrodes;
   (h) a set of operable valves in the liquid flow lines, the valves being electrically connected to and controlled by the computer system means; and
   (i) program means to program the computer system means to operate the computer system means in a dynamic mode in which the first liquid test solution is flowed through the flow cell and then, without removal of the permeable sample from the flow cell, the second liquid is flowed through the flow cell.

2. A system for the measurement of streaming potential as in claim 1 and further including means to measure the rate of the flow through the sample.

3. A system for the measurement of streaming potential as in claim 2 wherein the means to measure the flow rate is an electronic balance.

4. A system for the measurement of streaming potential as in claim 1 wherein said system further includes a conductivity meter connectable to the electrodes and connected to the computer system means and switch means to switch the electrodes between the electrometer and the conductivity meter, said switch means being connected to and controlled by the computer system means.

5. A system for the measurement of streaming potential as in claim 1 wherein said electrometer has an analog output and said computer system means includes an analog-to-digital converter.

6. A system for the measurement of streaming potential as in claim 1 and further including a liquid pressure transducer connected to said flow lines to measure the pressure therein, said liquid pressure transducer being connected to said computer system means.

7. A system for the measurement of streaming potential as in claim 1 and further including a third air-tight liquid reservoir connected to the liquid flow lines and the source of air pressure, the third reservoir adapted to contain a liquid whose effect on the sample is to be tested.

8. A system for the measurement of streaming potential as in claim 1 wherein at least one of the valves is a spurt valve means which is rapidly operable to open and close in less than 60 seconds and which is connected to the flow line leading to the orifice of the flow cell to provide spurts of the liquids to the flow cell.

9. A system for the measurement of streaming potential and conductivity by flow of a liquid through a permeable sample to determine zeta potential, the system including:
   (a) a flow cell adapted to removably hold the permeable sample, said permeable sample being used to conduct series of measurements while being held continually within the flow cell, said flow cell having first and second orifices and a body portion adapted to permit the flow of liquid from the first orifice through the cell body portion and permeable sample to the second orifice;
   (b) a programmable electronic computer system means to provide a program of electric control signals to control the flow of liquids through the flow cell;
   (c) at least first and second air-tight liquid reservoirs, the first reservoir containing a first liquid which is a test solution comprising a dilute solution of an electrolyte which provides a set of base measurements and the second reservoir containing a second liquid whose effect on the permeable sample is to be tested;
   (d) a supply of pressurized air connected to the first and second reservoirs to apply pressure to the liquids therein;

(e) a series of liquid flow lines leading from the first and second reservoirs to at least one of said flow cell orifices;
(f) a pair of electrodes within the flow cell adapted to be positioned at opposite ends of the permeable sample therein;
(g) an electrometer electrically connected to the electrodes and to the computer system means to measure electrical potential across the electrodes;
(h) a conductivity meter connectable to the electrodes and connected to the computer system means;
(i) a set of operable valves in the liquid flow lines, the valves being electrically connected to and controlled by the computer system means;
wherein at least one of the valves is a spurt valve means which is rapidly operable to open and close in less than 60 seconds and which is connected to the flow line leading to the orifice of the flow cell to provide spurts of the first and second liquids to the flow cell; and
(j) program means to program the computer system means to operate the computer system means in a dynamic mode in which the first liquid test solution is flowed through the flow cell and then, without removal of the permeable sample from the flow cell, the second liquid is flowed through the flow cell.

10. A system as in claim 9 and further including switch means to switch the electrodes between the electrometer and the conductivity meter, said switch means being connected to and controlled by said computer system means.

11. A system as in claim 9 wherein said electrometer has an analog output and said computer system means includes an analog-to-digital converter.

12. A system as in claim 9 and further including a liquid pressure transducer connected to said flow lines to measure the pressure therein, said liquid pressure transducer being connected to said computer system means.

13. A system as in claim 9 and further including a third air-tight liquid reservoir connected to the liquid flow lines and the source of air pressure and adapted to contain a liquid whose effect on the sample is to be tested.

14. A method for the measurement of streaming potential by the flow of a liquid through a permeable sample, the method including the steps of:
(a) placing a permeable sample in a flow cell having first and second orifices and a body portion adapted to permit the flow of liquid from the first orifice through the cell body portion to the second orifice;
(b) generating a program of electric control signals from programmable computer system means to control the flow of liquids through the flow cell;
(c) flowing liquids through the flow cell from at least first and second air-tight liquid reservoirs, the first reservoir containing a first liquid which is a test solution to provide a set of base measurements and the second reservoir containing a second liquid whose effect on the sample is to be tested;
(d) applying pressurized air to the first and second reservoirs to apply pressure to the liquids therein;
(e) measuring the electrical potential across a pair of electrodes within the flow cell positioned at opposite ends of the sample therein, using an electrometer electrically connected to the electrodes and the computer;
(f) operating the computer means in a dynamic mode to control a set of electric operable valves in which the first liquid test solution is flowed through the flow cell and then, without removal of the sample from the flow cell, the second liquid is flowed through the flow cell.

15. A method for the measurement of streaming potential as in claim 14 and including measuring the conductivity of the sample during the liquid flows using a conductivity meter connectable to the electrodes and connected to the computer system means.

16. A method for the measurement of streaming potential as in claim 14 and including measuring the flow rate of the sample through the flow cell using a flow rate measurement.

17. A method for the measurement of streaming potential as in claim 14 and further measuring the pressure of the liquids using a liquid pressure transducer connected to flow lines from the reservoirs to the flow cell, said liquid pressure transducer being connected to said computer system means.

18. A method for the measurement of streaming potential as in claim 14 and further including filling an air-tight liquid reservoir with a third liquid whose effect on the permeable sample is to be tested and then, without removal of the permeable sample from the flow cell, flowing the third liquid through the flow cell.

19. A method for the measurement of streaming potential and conductivity by the flow of a liquid through a permeable sample to determine zeta potential, the method including the steps of:
(a) placing a permeable sample in a flow cell having first and second orifices and a body portion adapted to permit the flow of liquid from the first orifice through the cell body portion to the second orifice;
(b) generating a program of electric control signals from programmable computer system means to control the flow of liquids;
(c) flowing liquids through the flow cell from at least first and second air-tight liquid reservoirs, the first reservoir containing a first liquid which is a test solution to provide a set of base measurements and the second reservoir containing a second liquid whose effect on the sample is to be tested;
(d) applying pressurized air to the first and second reservoirs to apply pressure to the liquids therein;
(e) measuring the electrical potential and conductivity across a pair of electrodes within the flow cell positioned at opposite ends of the sample therein, using an electrometer and a conductivity meter each electrically connected to the electrodes and to the computer;
(f) operating the computer means in a dynamic mode to control a set of electric operable valves in which the first liquid test solution is flowed through the flow cell in a series of spurts, each spurt being in the range of 15 seconds to 120 seconds, and then, without removal of the sample from the flow cell, the second liquid is flowed through the flow cell in a series of spurts, each spurt being in the range of 15 seconds to 120 seconds.

20. A method for the measurement of streaming potential and conductivity as in claim 19 and further measuring the pressure of the liquids using a liquid pressure transducer connected to flow lines from the reservoirs to the flow cell, said liquid pressure transducer being connected to said computer system means.

21. A method for the measurement of streaming potential as in claim 19 and further including filling a third air-tight liquid reservoir with a third liquid whose effect on the permeable sample is to be tested and then, without removal of the permeable sample from the flow cell, flowing the third liquid through the flow cell.

* * * * *